United States Patent
Michelson

(10) Patent No.: US 7,608,107 B2
(45) Date of Patent: Oct. 27, 2009

(54) EXPANDABLE IMPLANT WITH INTERLOCKING WALLS AND METHOD FOR USE THEREOF

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 595 days.

(21) Appl. No.: 10/973,974

(22) Filed: Oct. 26, 2004

(65) Prior Publication Data

US 2005/0060037 A1 Mar. 17, 2005

Related U.S. Application Data

(63) Continuation of application No. 09/900,305, filed on Jul. 6, 2001, now Pat. No. 6,808,537.

(60) Provisional application No. 60/216,785, filed on Jul. 7, 2000.

(30) Foreign Application Priority Data

Feb. 5, 2001 (WO) ..................... PCT/US01/03657
Feb. 5, 2001 (WO) ..................... PCT/US01/03658

(51) Int. Cl.
*A61F 2/44* (2006.01)
(52) U.S. Cl. ................................ 623/17.15; 623/17.11
(58) Field of Classification Search .... 623/17.11–17.16
See application file for complete search history.

(56) References Cited

U.S. PATENT DOCUMENTS

| 3,875,595 A | 4/1975 | Froning |
| 4,309,777 A | 1/1982 | Patil |
| 4,349,921 A | 9/1982 | Kuntz |
| 4,401,112 A | 8/1983 | Rezaian |

(Continued)

FOREIGN PATENT DOCUMENTS

DE 44 16 605 C1 6/1995

(Continued)

*Primary Examiner*—Pedro Philogene
(74) *Attorney, Agent, or Firm*—Martin & Ferraro, LLP

(57) ABSTRACT

An interbody spinal fusion implant for insertion across a disc space between two vertebrae includes a mid-longitudinal axis, upper and lower members each having portions adapted for placement in contact with one of the two vertebrae, and corresponding proximal and distal ends with a length therebetween. The upper and lower members articulate therebetween adjacent either the proximal or distal ends allowing for expansion of the implant from a collapsed height to an increased height. The upper and lower members include side walls adapted to cooperatively engage one another alone a portion of the length of the side walls to hold a portion of the upper and lower members apart so as to maintain the increased height. One of the side walls may have a first load bearing surface with a longitudinal axis that is non-perpendicular to the mid-longitudinal axis of the implant and another side wall may have a second load bearing surface for contacting said first load bearing surface. The side walls may also have interior and exterior surfaces, where one of the interior surfaces of one of the upper or lower members contacts one of the exterior surfaces of the other of the upper and lower members to form a generally coplanar transition between the upper and lower members.

159 Claims, 48 Drawing Sheets

U.S. PATENT DOCUMENTS

| | | | |
|---|---|---|---|
| 4,501,269 A | 2/1985 | Bagby | |
| 4,553,273 A | 11/1985 | Wu | |
| 4,554,914 A | 11/1985 | Kapp et al. | |
| 4,636,217 A | 1/1987 | Ogilvie et al. | |
| 4,657,550 A | 4/1987 | Daher | |
| 4,714,469 A | 12/1987 | Kenna | |
| 4,759,769 A | 7/1988 | Hedman et al. | |
| 4,863,476 A | 9/1989 | Shepperd | |
| 4,932,975 A | 6/1990 | Main et al. | |
| 4,961,740 A | 10/1990 | Ray et al. | |
| 5,015,247 A | 5/1991 | Michelson | |
| 5,055,104 A | 10/1991 | Ray | |
| 5,059,193 A | 10/1991 | Kuslich | |
| 5,062,850 A | 11/1991 | MacMillan et al. | |
| 5,123,926 A | 6/1992 | Pisharodi | |
| 5,147,402 A | 9/1992 | Bohler et al. | |
| 5,171,278 A | 12/1992 | Pisharodi | |
| 5,192,327 A | 3/1993 | Brantigan | |
| 5,236,460 A | 8/1993 | Barber | |
| 5,258,031 A | 11/1993 | Salib et al. | |
| 5,263,953 A | 11/1993 | Bagby | |
| 5,290,312 A | 3/1994 | Kojimoto et al. | |
| 5,306,310 A | 4/1994 | Siebels | |
| 5,314,477 A | 5/1994 | Marnay | |
| 5,336,223 A | 8/1994 | Rogers | |
| 5,390,683 A | 2/1995 | Pisharodi | |
| 5,397,364 A | 3/1995 | Kozak et al. | |
| 5,439,684 A | 8/1995 | Prewett et al. | |
| 5,455,231 A | 10/1995 | Constantz et al. | |
| 5,464,439 A | 11/1995 | Gendler | |
| 5,507,813 A | 4/1996 | Dowd et al. | |
| 5,507,816 A | 4/1996 | Bullivant | |
| 5,522,899 A | 6/1996 | Michelson | |
| 5,549,679 A | 8/1996 | Kuslich | |
| 5,554,191 A | 9/1996 | Lahille et al. | |
| 5,593,409 A | 1/1997 | Michelson | |
| 5,609,635 A | 3/1997 | Michelson | |
| 5,653,763 A | 8/1997 | Errico et al. | |
| 5,665,122 A | 9/1997 | Kambin | |
| 5,693,100 A | 12/1997 | Pisharodi | |
| 5,702,391 A | 12/1997 | Lin | |
| 5,702,455 A | 12/1997 | Saggar | |
| 5,713,904 A | 2/1998 | Errico et al. | |
| 5,749,916 A | 5/1998 | Richelsoph | |
| 5,776,199 A | 7/1998 | Michelson | |
| 5,782,832 A | 7/1998 | Larsen et al. | |
| 5,785,710 A | 7/1998 | Michelson | |
| 5,800,550 A | 9/1998 | Sertich | |
| 5,827,328 A * | 10/1998 | Buttermann | 623/17.13 |
| 5,865,848 A | 2/1999 | Baker | |
| 5,885,982 A | 3/1999 | Dolynchuk et al. | |
| 5,888,224 A | 3/1999 | Beckers et al. | |
| 5,928,284 A | 7/1999 | Mehdizadeh | |
| 5,980,522 A | 11/1999 | Koros et al. | |
| 5,989,290 A | 11/1999 | Biedermann et al. | |
| 6,015,436 A | 1/2000 | Schonhoffer | |
| 6,019,792 A | 2/2000 | Cauthen | |
| 6,039,761 A | 3/2000 | Li et al. | |
| 6,045,579 A | 4/2000 | Hochshuler et al. | |
| 6,059,829 A | 5/2000 | Schlapfer et al. | |
| 6,080,193 A | 6/2000 | Hochshuler et al. | |
| 6,087,555 A | 7/2000 | Dunstan et al. | |
| 6,093,207 A | 7/2000 | Pisharodi | |
| 6,102,950 A | 8/2000 | Vaccaro | |
| 6,106,558 A * | 8/2000 | Picha | 623/23.74 |
| 6,117,174 A | 9/2000 | Nolan | |
| 6,126,689 A | 10/2000 | Brett | |
| 6,129,763 A | 10/2000 | Chauvin et al. | |
| 6,143,031 A | 11/2000 | Knothe et al. | |
| 6,159,244 A * | 12/2000 | Suddaby | 623/17.11 |
| 6,174,334 B1 * | 1/2001 | Suddaby | 623/17.11 |
| 6,176,882 B1 | 1/2001 | Biedermann et al. | |
| 6,183,517 B1 * | 2/2001 | Suddaby | 623/17.16 |
| 6,190,414 B1 | 2/2001 | Young et al. | |
| 6,190,880 B1 | 2/2001 | Israel et al. | |
| 6,193,757 B1 * | 2/2001 | Foley et al. | 623/17.16 |
| 6,201,039 B1 | 3/2001 | Brown et al. | |
| 6,217,579 B1 | 4/2001 | Koros | |
| 6,332,895 B1 * | 12/2001 | Suddaby | 623/17.11 |
| 6,375,683 B1 | 4/2002 | Crozet et al. | |
| 6,419,705 B1 | 7/2002 | Erickson | |
| 6,454,806 B1 | 9/2002 | Cohen et al. | |
| 6,562,074 B2 * | 5/2003 | Gerbec et al. | 623/17.15 |
| 6,582,431 B1 | 6/2003 | Ray | |
| 6,706,070 B1 | 3/2004 | Wagner et al. | |
| 6,743,255 B2 * | 6/2004 | Ferree | 623/17.11 |
| 6,821,298 B1 | 11/2004 | Jackson | |
| 6,905,512 B2 | 6/2005 | Paes et al. | |

FOREIGN PATENT DOCUMENTS

| | | |
|---|---|---|
| FR | 2 717 068 | 9/1995 |
| SU | 1225561 A | 4/1986 |
| SU | 1424826 A1 | 9/1988 |
| WO | WO 97/00054 | 12/1997 |
| WO | WO 99/26562 | 6/1999 |
| WO | WO 99/42062 | 8/1999 |
| WO | WO 00/12033 | 3/2000 |
| WO | WO 00/25706 | 5/2000 |
| WO | WO 00/35389 | 6/2000 |
| WO | WO 00/66045 | 11/2000 |
| WO | WO 00/74605 | 12/2000 |
| WO | WO 00/78253 | 12/2000 |

* cited by examiner

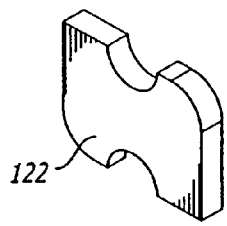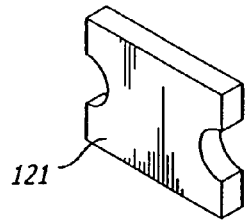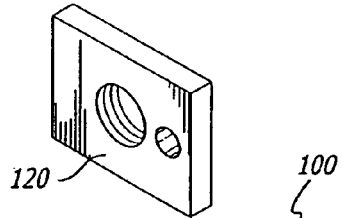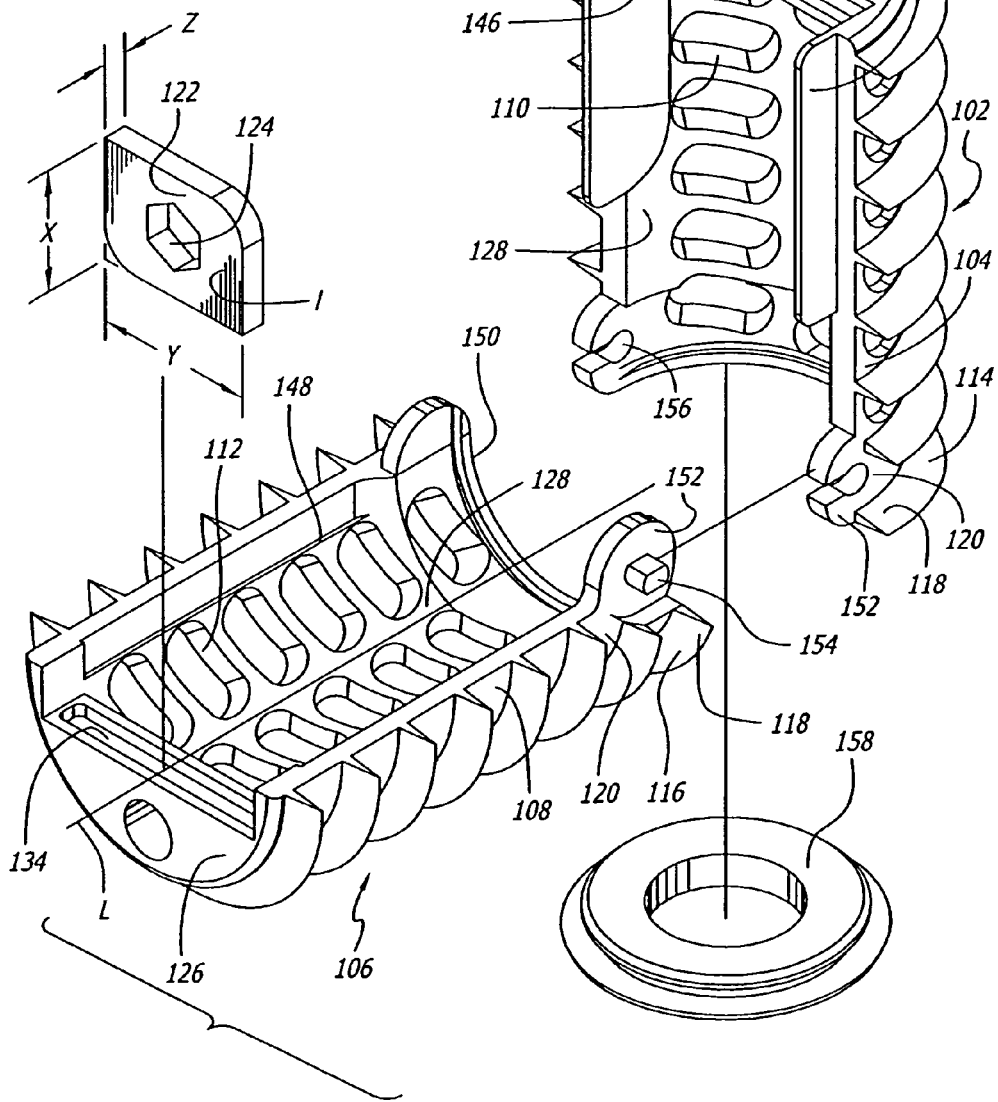

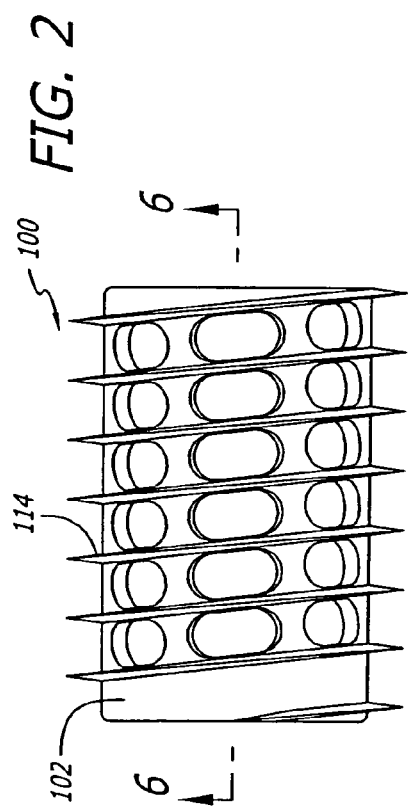
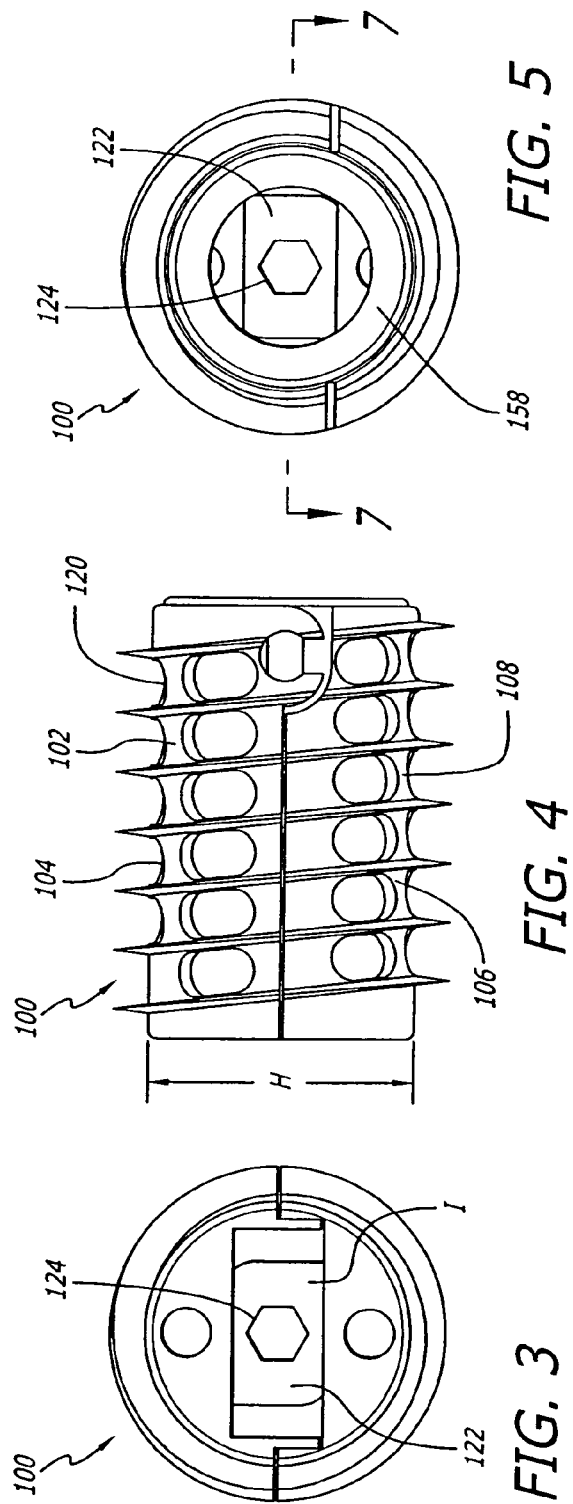

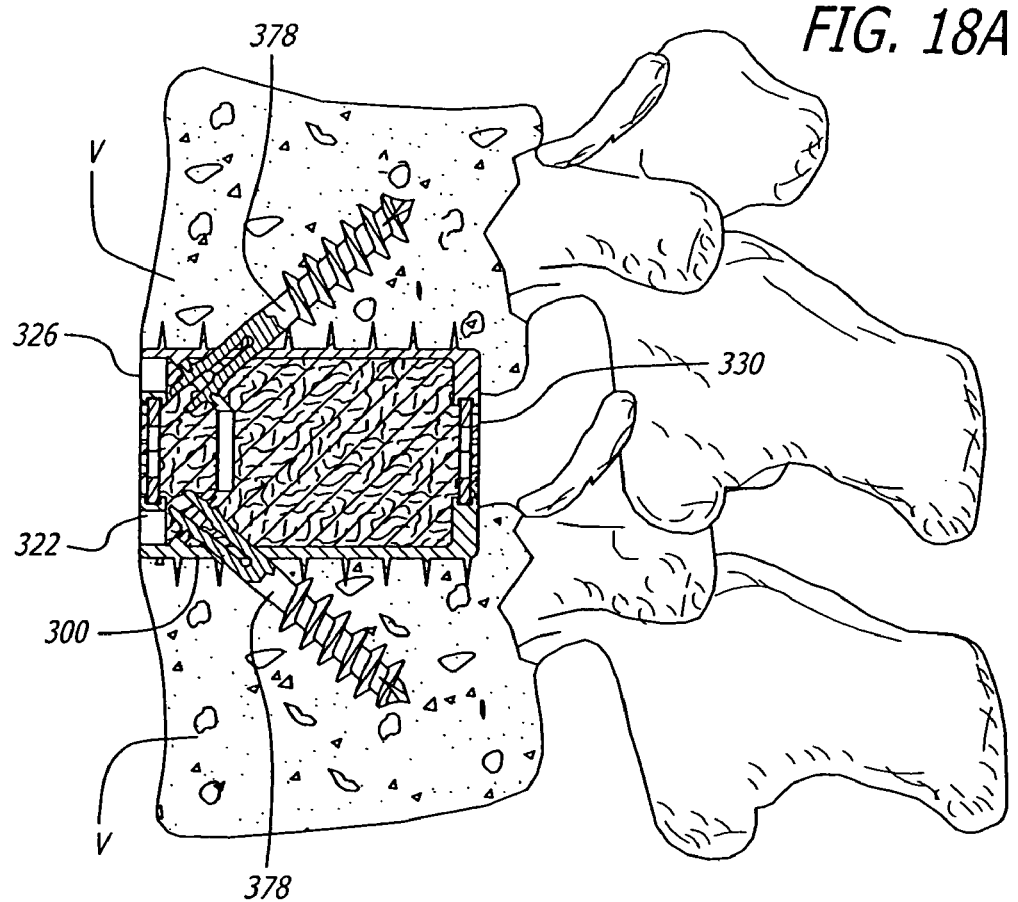
FIG. 18A
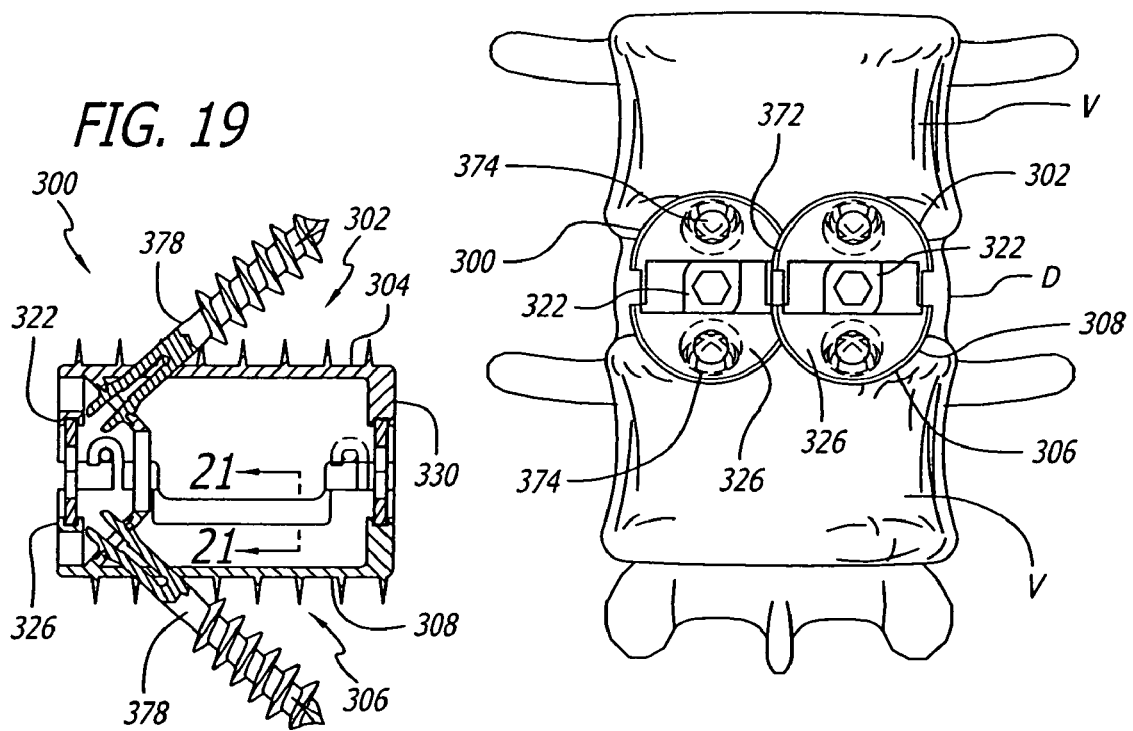
FIG. 19
FIG. 18B

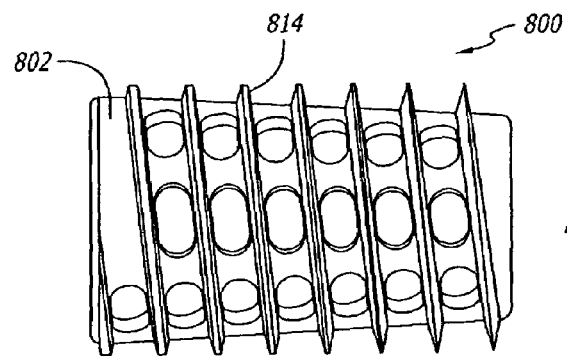
FIG. 34
FIG. 35
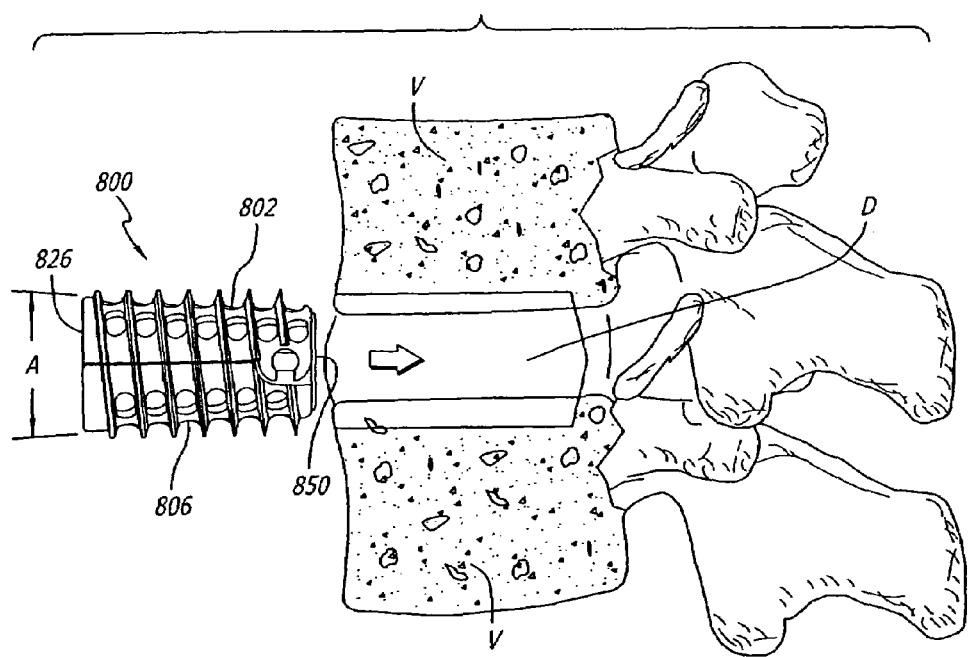

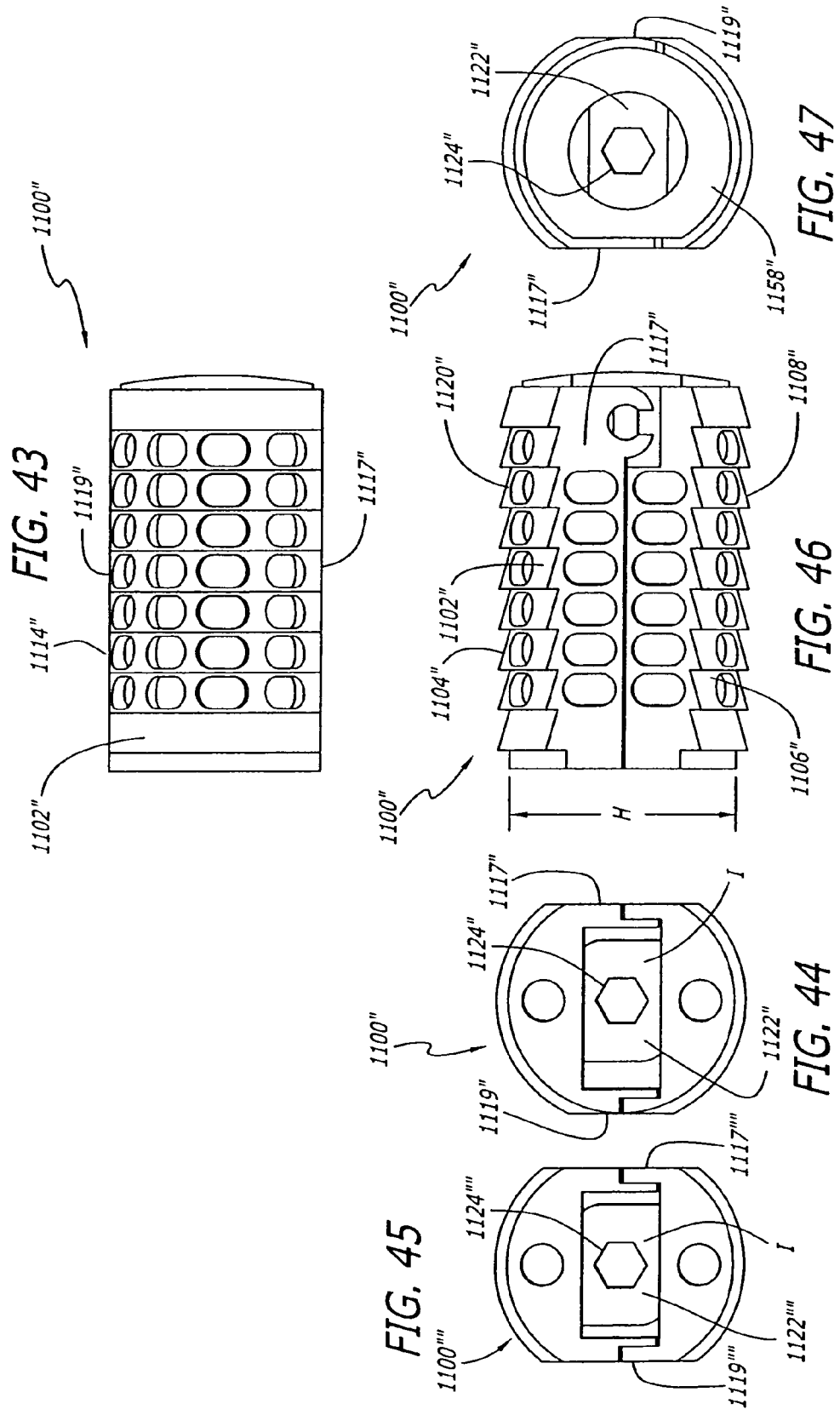

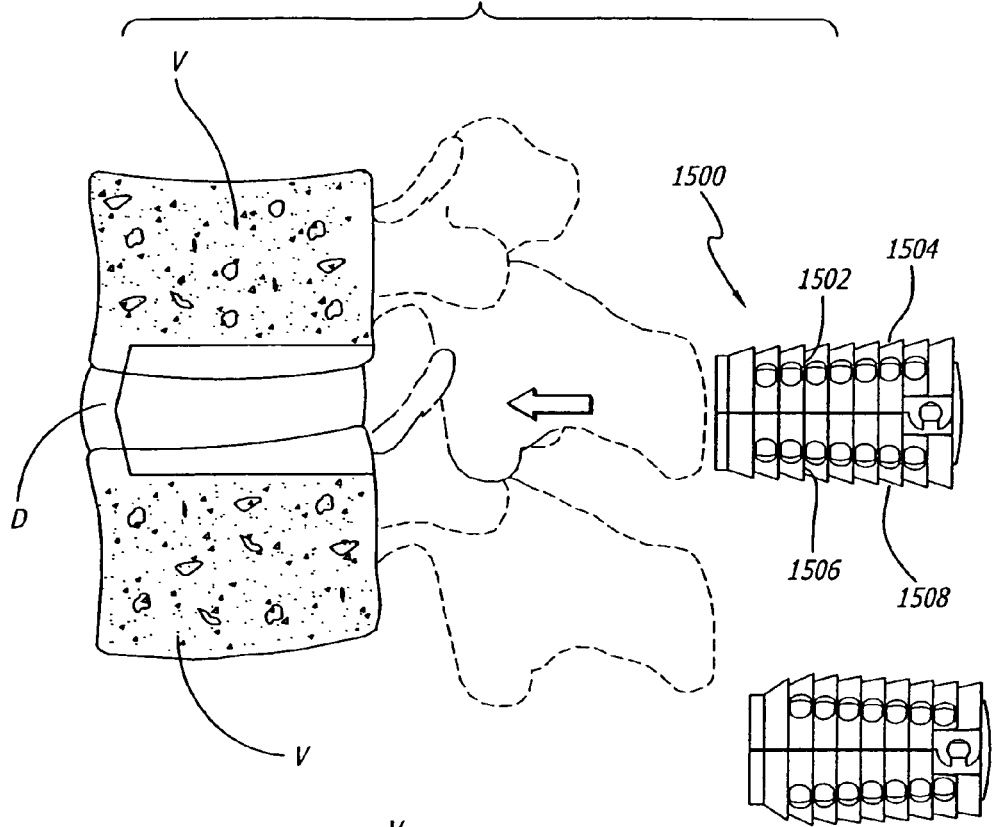
FIG. 58
FIG. 59
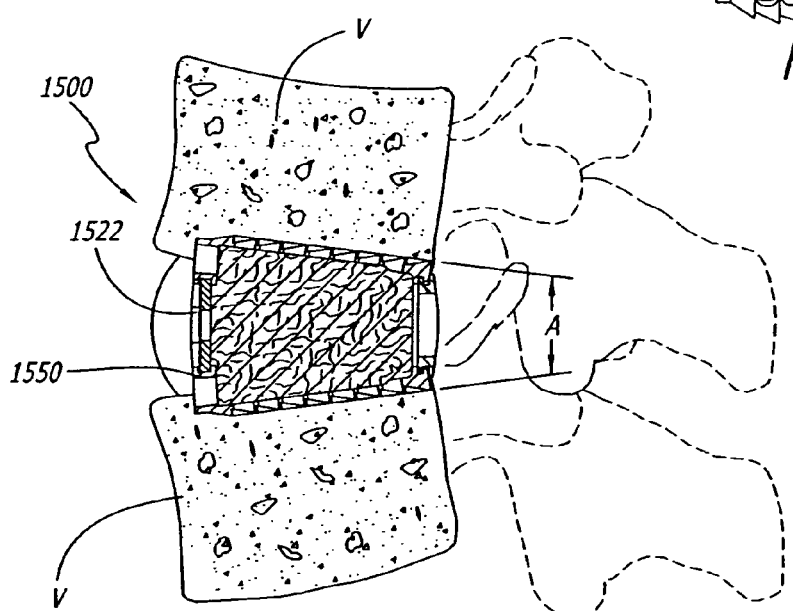
FIG. 60

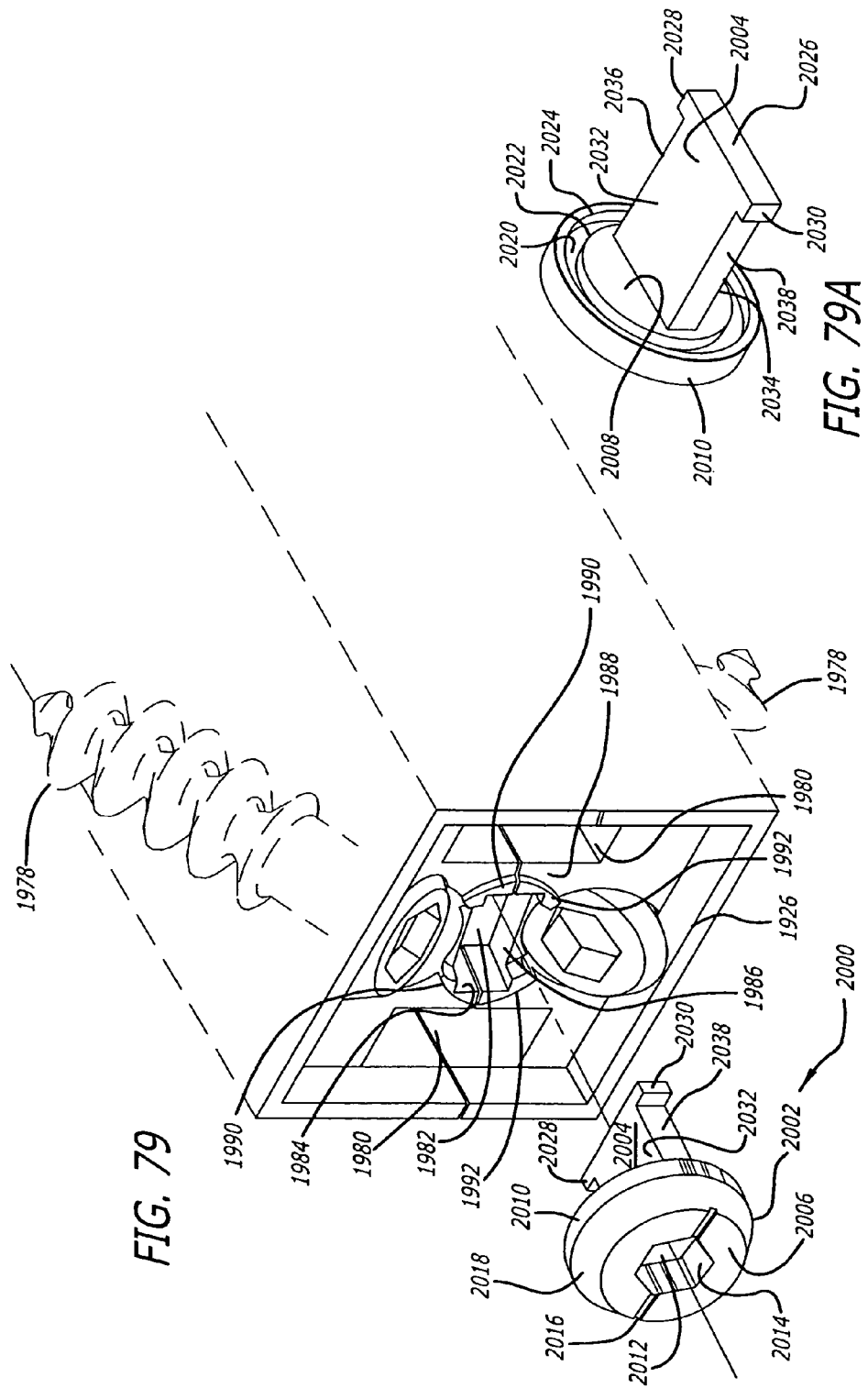

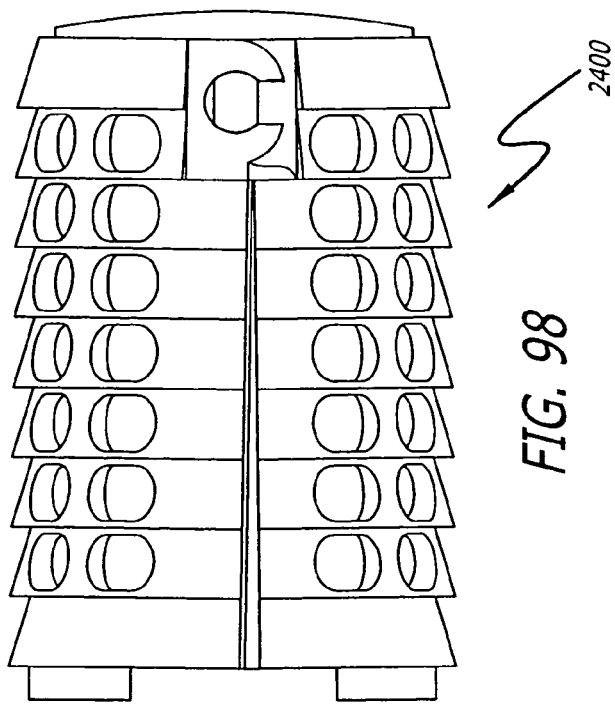
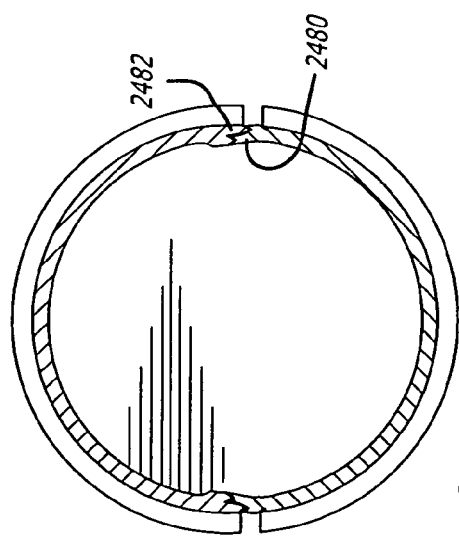
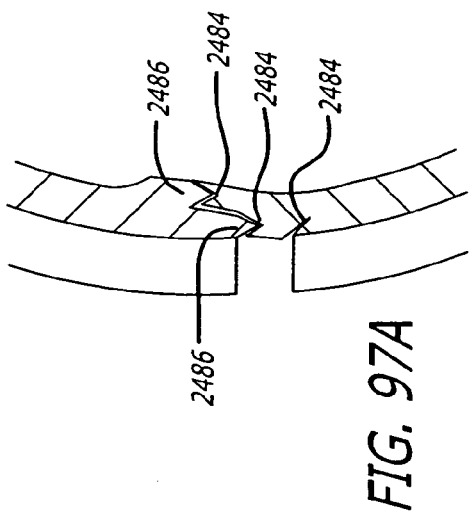
FIG. 98
FIG. 97
FIG. 97A

EXPANDABLE IMPLANT WITH INTERLOCKING WALLS AND METHOD FOR USE THEREOF

This application is a continuation of U.S. patent application Ser. No. 09/900,305, filed Jul. 6, 2001, now U.S. Pat. No. 6,808,537; which claims the benefit of U.S. Provisional Application No. 60/216,785, filed Jul. 7, 2000; International Application No. PCT/US01/03657, filed Feb. 5, 2001; and International Application No. PCT/US01/03658, filed Feb. 5, 2001; all of which are incorporated by reference herein.

BACKGROUND OF THE INVENTION

1. Field of the Invention

The present invention relates generally to an improved interbody (for placement at least in part between adjacent vertebral bodies in the space previously occupied by disc material) spinal fusion implant for the immobilization of vertebrae. In particular, the invention relates to a spinal fusion implant that is selectively directionally expandable and which specifically has height raising capabilities that are utilized once the implant is initially positioned. Such height raising capability may be utilized within the spine anteriorly, posteriorly, or both and to various extents, respectively so as to raise the front, back, or both of the implant by the same or various amounts. More particularly, the invention relates to an implant having portions of upper and lower members that have a first, collapsed position relative to one another during insertion and a second, expanded position relative to one another allowing for an increased height. Further, the invention relates to cooperatively configured interlocking side walls of the upper and lower members that are adapted to hold the implant in an expanded position when moved from the collapsed position.

2. Description of the Related Art

Threaded and push-in spinal fusion implants having upper and lower portions adapted for placement in contact with adjacent vertebral bodies are known in the related art. The first artificial threaded spinal fusion implant was invented by Michelson and is disclosed in U.S. Pat. No. 5,015,247, filed Jun. 13, 1988, which is hereby incorporated by reference. Various push-in spinal fusion implants have been invented by Michelson and are disclosed in U.S. Pat. No. 5,593,409, filed Feb. 17, 1995 and U.S. Pat. No. 5,776,199, filed Jun. 28, 1988, which are hereby incorporated by reference.

Lordotic, frusto-conical, or tapered, threaded and push-in spinal fusion implants are also known in the art. By way of example, Michelson has invented such implants as disclosed in U.S. application Ser. No. 08/480,904 and EP 96917996.9, and U.S. Pat. No. 5,609,635, filed Jun. 7, 1995, which are hereby incorporated by reference.

Expandable fusion implants are known in the related art. The first expandable spinal fusion (allowing for the growth of bone from vertebral body to vertebral body through the implant) implant was invented by Michelson and is disclosed in U.S. Pat. No. 5,776,199, filed Jun. 28, 1988, previously incorporated by reference herein.

Lordotic, frusto-conical, or tapered, spinal fusion implants have the advantage of restoring or enhancing spinal lordosis. Threaded and push-in spinal fusion implants offer the advantage of being easily positioned in the implantation space and of having excellent fastening or holding features. Expandable fusion implants offer the advantage of allowing for the placement of a potentially larger implant through a smaller opening in a patient's body. Selective expansion along a single direction, (e.g. vertically only when correctly installed) offers the advantage of increasing the height of the implant and therefore the distraction of the disc space, but without a concomitant increase in the width of the implant.

There exists a need for an artificial interbody spinal fusion implant providing for all of the aforementioned advantages in combination.

SUMMARY OF THE INVENTION

In accordance with the present invention, as embodied and broadly described herein, there is provided an expandable artificial interbody spinal fusion implant for insertion across a disc space between two adjacent vertebral bodies of a human spine. The implant of the present invention includes an upper member having a portion adapted for placement toward and into contact with or at least in part within one of the adjacent vertebral bodies and a lower member having a portion adapted for placement toward and into contact with or at least in part within the other of the adjacent vertebral bodies. The portions of the upper and lower members have at least one opening in communication with one another for permitting for the growth of bone from a vertebral body to an adjacent vertebral body through the implant. The upper and lower members are articulated therebetween, preferably proximate one of the proximal ends and the distal ends of the upper and lower members and preferably allow for divergence between the articulating members at the end opposite the articulating end of the implant. The upper and lower members have a first position relative to one another that allows for a collapsed implant height and a second position relative to one another that allows for an increased height. The portions of the upper and lower members in the first position of the present invention may be parallel or angled to one another. Preferably, at least a portion of a bone-engaging projection, such as a helical thread, ratchet, or knurling, is on the exterior of each of the opposed portions of the upper and lower members for engaging the adjacent vertebral bodies. The upper and lower members have a leading or distal end, an opposite trailing or proximal end, and a length therebetween. A cooperatively configured interlocking side wall of the upper and lower members is adapted to hold at least a portion of the upper and lower members apart so as to maintain the increased height of the implant and resist the collapse of the implant to the collapsed implant height. Expansion of the implant preferably increases the implant height only, that is in a plane preferably passing through the mid-longitudinal axis of the implant and the upper and lower members.

Each of the upper and lower members of at least one embodiment of the present invention have side walls adapted to cooperatively engage one another along at least a portion of the length of the side walls to hold at least a portion of the upper and lower members apart so as to maintain the increased height of the implant and resist the collapse of the implant to the collapsed implant height when the implant is in a final deployed position. Preferably the side walls of at least one, and if desired both, of the upper and lower members flex when the implant is moved from the first position to the second position. In particular, when the implant is moved from the first position to the second position certain of the side walls may spring from a position closer to the mid-longitudinal axis of the implant to a position further away from the mid-longitudinal axis or may spring from a position further from the mid-longitudinal axis of the implant to a position closer to the mid-longitudinal axis. This movement of at least one of the side walls may include rotating at least a portion of the side wall along an arc around an axis that is parallel to the mid-longitudinal axis of the implant when the implant is moved from the first position to the second position. These rotational, flexing, or springing forces acting to engage the cooperatively configured side walls of the upper and lower members together add lateral stability to the implant while maintaining the increased height of the implant.

Preferably, the side walls of the upper and lower members have cooperatively engaging stepped surfaces. Preferred stepped surfaces of one embodiment of the present invention include interdigitating projections and detents. The side walls having detents preferably have more detents than the cooperatively engaging side walls having projections have projections to permit the implant to move from the first position to the second position. During movement of the implant from the first position to the second position the side walls having detents in one embodiment have at least one detent that narrows during movement of the side wall having detents. This movement moves the side wall having detents into alignment and engagement with the projections of the wall having projections to increase the height of the implant. One particular preferred embodiment of the present invention includes side walls with two projections adapted to cooperatively engage side walls with three detents. Moving the two projections from the lower two of the three indentations to the higher two of the three indentations results in an increase to the maximum height of the implant.

The implant in one embodiment may be expanded with an extrinsic tool and then the expanded portions held apart in the second position by the interlocking side walls of the upper and lower members. The present invention includes expanding the implant with a tool, such as a spreader or a distractor, but is not limited to a scissors type, a rack and gear type, a threaded member type or any other type of particular external expander tool mechanism. Each tool nevertheless preferably engages the upper and the lower implant members to urge the implant apart. Then the interlocking side walls of the upper and lower members maintain the implant at an expanded height. The amount of the increase in the height of the implant may vary depending upon the amount of distraction of the implant desired by the physician.

Preferred forms of interbody spinal fusion implants have a substantial hollow portion. Certain expandable interbody spinal fusion implants that increase in height only of the related art contain an expansion mechanism passing longitudinally therethrough or an expansion mechanism that is configured for movement of the expansion mechanism from proximate one end of the hollow portion to proximate the other end of the hollow portion, thus requiring the expander to pass through the length of the hollow portion. A preferred embodiment of the present invention overcomes these limitations.

The portions of the upper and lower members are moved from a parallel orientation to an angled orientation; or a parallel orientation to an increased height parallel orientation; or an angled orientation to a parallel orientation; or an angled orientation to an increased height angled orientation that may be the same or a different angle relative to one another; or from a first height at each end to a second and greater height at at least one and possibly both ends. Each of the upper and lower members structurally cooperates with one another via the interlocking side walls so as to keep the implant in its expanded position.

The implant is preferably packed full of bone or other fusion-promoting substances prior to expansion of the implant. Expansion of the implant results in a space being formed in the implant interior into which additional fusion promoting substances such as bone may preferably be packed.

When installing a preferred implant from the posterior approach to the spine, the implant is driven from the trailing end and the leading end at the anterior aspect of the spine is raised or expanded. When expanded, the implant installed from the posterior aspect leaves a void at the leading end of the implant near the anterior aspect of the spine because the leading end of the implant has been made taller, the void preferably being packed with bone after expansion of the implant. Additionally, any path left behind in the bone filled interior of the implant by any tool passing through the bone filled interior is preferably packed with bone as well.

The implant may have an overlapping step-cut wall junction between the upper and lower members, which offers as some of its advantages: increasing the lateral rigidity of the implant, holding the implant in the closed first position until expanded, and to the extent desired retaining the fusion-promoting materials within the implant. The wall junction may be either solid or perforated.

One of the upper and lower members preferably has an interior wall extending toward the other of the upper and lower members and, more preferably, has two interior walls extending from each side thereof. The interior walls may be aligned parallel with the longitudinal axis of the implant. The other one of the upper and lower members preferably has an interior-contacting surface adapted to contact or receive the interior longitudinal wall.

By way of example, one of the upper and lower members may have a longitudinally extending interior wall, which is preferably unexposed, extending toward the other of the upper and lower members when the implant is in an initial insertion position. When the implant is in the final expanded or deployed position the implant has a preferred shape such that each of the portions of the upper and lower members are separated by at least a portion of interior wall, which in this position preferably has an exposed side.

The upper and lower members in certain embodiments are articulated to one another so one of the respective ends of the upper and lower members remain articulated while the other of the respective ends of the upper and lower members are free to move away from one another. In a preferred embodiment, the articulating means is achieved without a third member, such as an axle shaft, for example, passing through the implant. The articulating means preferably is formed into the implant walls themselves, and in a further preference in such a way that the two-implant halves may be articulated when at 90 degrees to each other. The halves then are moved, much like a book closing, toward each other prior to insertion into the implantation space in the spine. Once the upper and lower members are closed from the approximately 90 degrees articulating position, much like closing the leaves of a book, the upper and lower members of the implant are locked together at the articulation so that the members will not disarticulate when in use. Other types of articulation as would be known to one of ordinary skill in the art are within the scope of the present invention.

By way of example, the upper and lower members preferably have a cooperating rotational articulation or pivot point between a proximate one of the proximal end and the distal end of the upper and lower members. The cooperating rotational articulation preferably is proximate one of the proximal end and the distal end of the upper and lower members at an end opposite to the end to be expanded. A preferred rotational articulation configuration includes cooperating brackets and projections configured such that articulation therebetween occurs when the upper and lower members are substantially perpendicular to one another. Such a configuration offers the advantage that the brackets and the projections will not disengage one another when articulated for use such as insertion into the spine and subsequent expansion within a range of movement of the upper and lower members resulting from expanding the implant.

When the implant is in the final or expanded position the implant in one of the referred embodiments may take the general form of a cylinder or frusto-conical shape split along a horizontal plane through its mid-longitudinal axis wedged upper half from lower half by an inclined plane.

At least one and preferably both of the upper and lower members may have a screw hole passing through the trailing end, which preferably is adapted to receive a screw passing through the end of the upper and lower members and from the interior of the implant into each of the adjacent vertebral bodies to anchor the implant, further stabilize those vertebral bodies relative to each other, prevent undesirable motion at the vertebral body implant interfaces, increase the compressive load at the implant trailing end, prevent rocking; and thus mitigate against excessive peak loads and more uniformly distribute loads imparted to the implant over the length of the implant to the adjacent vertebral bodies. The implant may have a side configured, when in the expanded position, to cooperate with another interbody spinal fusion implant so as to allow the pair of implants to have a reduced combined width.

The trailing end of the implant preferably has a tool-engaging portion, but the implant may be adapted to cooperatively engage a driver at another location or by any means as would be known to one of ordinary skill in the art. This tool-engaging portion is adapted to engage an insertion tool that holds the implant during insertion in the spine. The configuration of the tool-engaging portion may be an opening, and more particularly an opening that is along the longitudinal axis of the implant. It is appreciated that the tool-engaging portion need not be an opening. A hole or a blind hole, threaded or otherwise, is preferred in another embodiment. In another preferred embodiment the opening preferably is a threaded slot that functions to cooperatively engage and disengage a tool for use in inserting the implant. In specific embodiments, the leading or trailing end may have wall portions, and/or be adapted to cooperatively engage a cap. Either the end wall portions or a cap may have an opening or openings that may function to hold fusion-promoting materials within the implant and/or, permit vascular access and bone growth therethrough.

By way of example, an implant configured for insertion from an anterior approach may be initially packed from the distal or leading end of the implant. The implant is then driven into position. Once the implant is expanded into the final position and any associated tool for expanding the implant is withdrawn from the implant, any void in the bone packed into the implant interior may be filled.

The accompanying drawings, which are incorporated in and constitute a part of this specification, are by way of example only and not limitation, and illustrate several embodiments of the invention, which together with the description, serve to explain the principles of the invention. The scope of the invention is limited only by the scope of the claims as from the present teachings other embodiments of the present invention shall be apparent to those skilled in the art.

BRIEF DESCRIPTION OF THE DRAWINGS

FIG. 1 is an exploded perspective view of a spinal fusion implant of one embodiment of the present invention;

FIG. 1A is a perspective view of an alternative embodiment of a blocker in the form of an expander for use with the implant of FIG. 1;

FIG. 1B is a perspective view of another alternative embodiment of a blocker for use with the implant of FIG. 1;

FIG. 1C is a perspective view of yet another alternative embodiment of a blocker for use with the implant of FIG. 1;

FIG. 2 is a top plan view of the implant of FIG. 1;

FIG. 3 is a trailing end view of the implant of FIG. 1;

FIG. 4 is a side elevation view of the implant of FIG. 1;

FIG. 5 is a leading end view of the implant with the end cap there attached of FIG. 1;

FIG. 18A is a cross-sectional side view of the implantation site formed across the space between two adjacent vertebral bodies and one of the implants of FIG. 17 installed into the implantation space;

FIG. 18B is a trailing end view of the anterior aspect of two adjacent vertebral bodies and the implant of FIG. 17 implanted therebetween in an expanded position as well as another embodiment designed to be used as a side-by-side pair;

FIG. 19 is a cross-sectional side view of the implant of FIG. 18A without bone or other fusion-promoting substances shown therein for the purpose of illustrating a preferred configuration for articulating the upper and lower members together with a hook and peg configuration that prevents the implant from over expanding and with an alternative second hook and peg shown on the right hand side of the figure in dashed lines;

FIG. 34 is a top plan view of another alternative embodiment of an implant of the present invention;

FIG. 35 is a side view of the implant of FIG. 34 being inserted from a generally anterior approach to the spine into an implantation site formed across a disc space and two adjacent vertebral bodies of the spine shown in partial cross-section;

FIG. 43 is a top plan view of an alternative embodiment of the implant of present invention;

FIG. 44 is a trailing end view of the implant of FIG. 43;

FIG. 45 is a trailing end view of yet another alternative embodiment of the implant of the present invention;

FIG. 46 is a side elevation view of an alternative embodiment of the implant of FIG. 43;

FIG. 47 is a leading end view of the implant of FIG. 43 with an end cap attached;

FIG. 58 is a cross-sectional side view of an implantation site formed posteriorly across the disc space between two adjacent vertebral bodies and a second embodiment of an implant of the present invention for posterior insertion being installed into the implantation site;

FIG. 59 is a side view of an alternative variation of a second embodiment of the implant of FIG. 58 for posterior insertion;

FIG. 60 is a cross-sectional side view of the implantation site formed across the space between two adjacent vertebral bodies and the implant of FIG. 58 installed into the implantation space;

FIG. 79 is a partial fragmentary exploded front perspective view of an expandable interbody spinal fusion implant with expanding and locking end cap in accordance with a preferred embodiment of the present invention;

FIG. 79A is a rear perspective view of the end cap of FIG. 79;

FIG. 97 is a trailing end view of the implant of FIG. 98;

FIG. 97A is an enlarged portion of the trailing end view of the implant of FIG. 97 showing the interlocking side walls of the implant when the implant is in the second or expanded position; and FIG. 98 is a side view of the implant of FIG. 93 in the second or expanded position.

DESCRIPTION OF THE PREFERRED EMBODIMENTS

Figure 6:
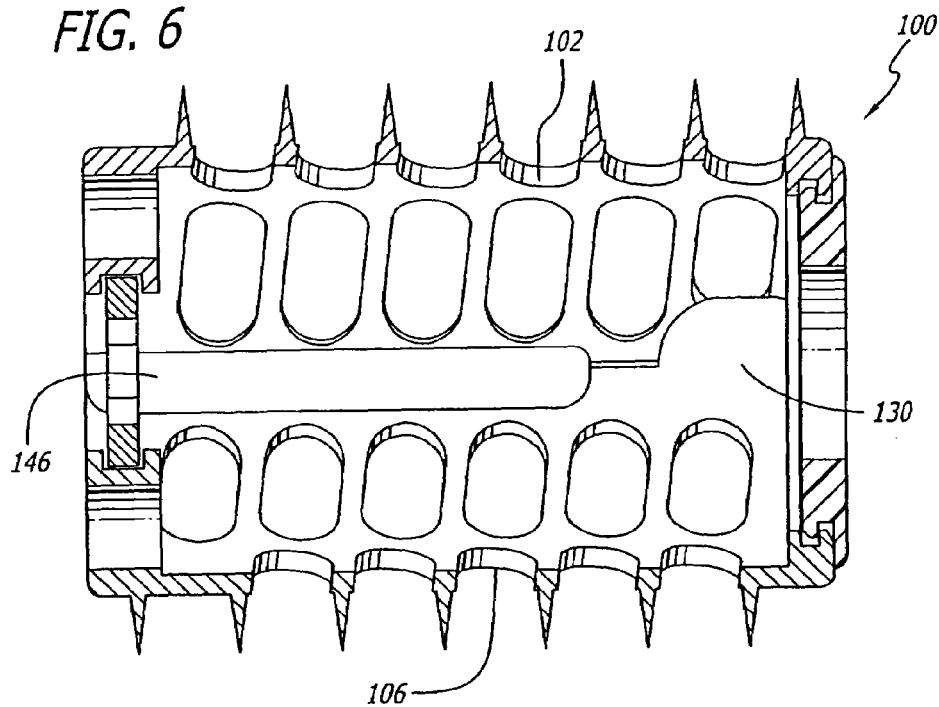
FIG. 6 is a cross-sectional view along line 6-6 of FIG. 2.
Figure 7:
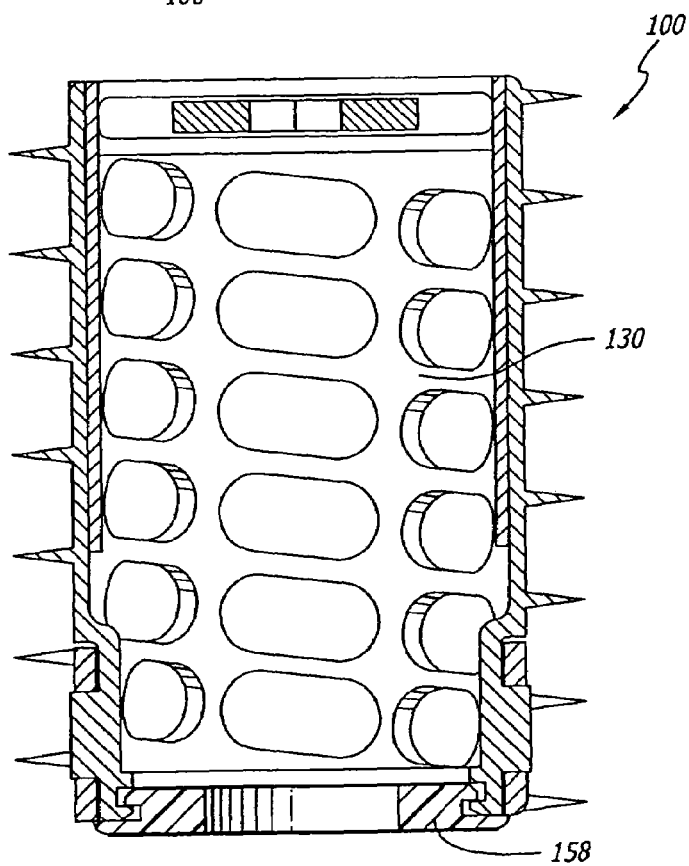
FIG. 7 is a cross-sectional view along line 7-7 of FIG. 5.

The following description is intended to be representative only and not limiting and many variations can be anticipated according to these teachings, which are included within the scope of this inventive teaching. Reference will now be made in detail to the preferred embodiments of this invention, examples of which are illustrated in the accompanying drawings.

Shown in FIGS. 1-7 and 10-13, in accordance with the present invention, as embodied and broadly described herein, is one embodiment of an expandable artificial interbody spinal fusion implant 100 for anterior insertion across a disc space D between two adjacent vertebral bodies V of a human spine. Implant 100 of the present invention includes an upper member 102 having an arcuate portion 104 adapted for placement toward and at least in part within the upper of the adjacent vertebral bodies V and a lower member 106 having an arcuate portion 108 adapted for placement toward and at least in part within the lower of the adjacent vertebral bodies V. Arcuate portions 104, 108 of upper and lower members 102, 106 have at least one opening 110, 112 in communication with one another for permitting for the growth of bone from vertebral body V to adjacent vertebral body V through implant 100. Upper and lower members 102, 106 are articulated therebetween at an adjacent one of the proximal ends and the distal ends of upper and lower members 102, 106 and allow for rotation between the articulating members at the end opposite the articulating end of implant 100. Upper and lower members 102, 106 have a first position relative to one another that allows for a collapsed implant height and a second position relative to one another that allows for an increased height. Arcuate portions 104, 108 of upper and lower members 102, 106 in the first position of the present invention are parallel to one another and form at least a portion of a cylinder along the length of implant 100. A bone-engaging projection 114, 116 in the form of a portion of at least one thread 118 is on an exterior 120 of each of opposed arcuate portions 104, 108 of upper and lower members 102, 106 for engaging adjacent vertebral bodies V.

While a specialized form of a blocker 121 is described in significant detail below with reference to expander 122, blocker 121 need not be in contact with upper and lower members 102, 106 when implant 100 is initially inserted into the implantation space. Blocker 121 may be a block or any type of spacer that is inserted between the articulated upper and lower members 102, 106 after implant 100 is positioned so as to hold portions of the upper and lower members 102, 106 spaced apart the optimal height and angulation relative to one another. That is the implant may be expanded with an extrinsic tool and then the expanded portions held apart in the second position by a third body blocker placed therebetween. Alternatively, as will be described below in detail with particular reference to FIGS. 93-98, the implant also may have cooperatively configured interlocking side walls of the upper and lower members in addition to or instead of the blocker or expander described herein. Further, a physician may be able to select from a series of blockers having different heights usable with the same implant. The present invention includes expanding the implant with a tool, such as a spreader or a distractor but is not limited to a scissors type, a rack and gear type, a threaded member type or any other specific type of movement mechanism. Each tool nevertheless preferably engages upper and lower implant members 102, 106 to urge them apart. Blocker 121 is then inserted into contact with upper and lower members 102, 106 to maintain implant 100 at an expanded height. The height of the gap created by expanding implant 100 may be measured so that the appropriately sized blocker 121 or specialized blocker, expander 122, may be inserted in implant 100 depending upon the amount of distraction of implant 100 desired by the surgeon.

Blocker 121 that is preferably in the form of expander 122 is located proximate at least one of the ends of the implant upper and lower members 102, 106 and holds at least a portion of upper and lower members 102, 106 apart so as to maintain the increased height of implant 100 and resist the collapse of implant 100 to the collapsed implant height. Expander 122 in the present embodiment increases the implant height as measured in a plane passing through the mid-longitudinal axis of implant 100 and upper and lower members 102, 106 during positioning of expander 122 and as may be desirable is capable of selectively increasing the height of the implant only.

Figure 10:
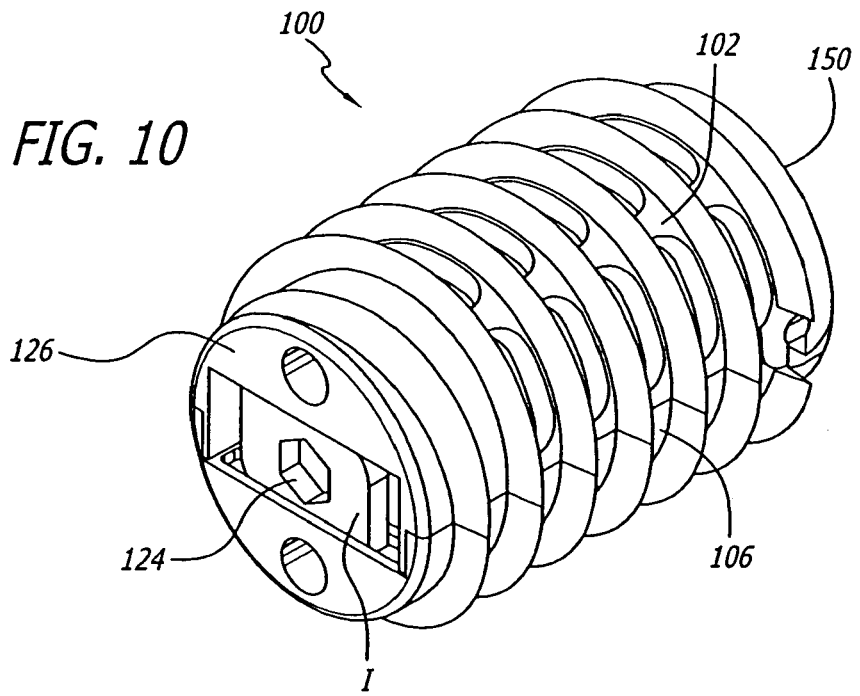
FIG. 10 is a trailing end perspective view of the implant of FIG. 1.
Figure 13:
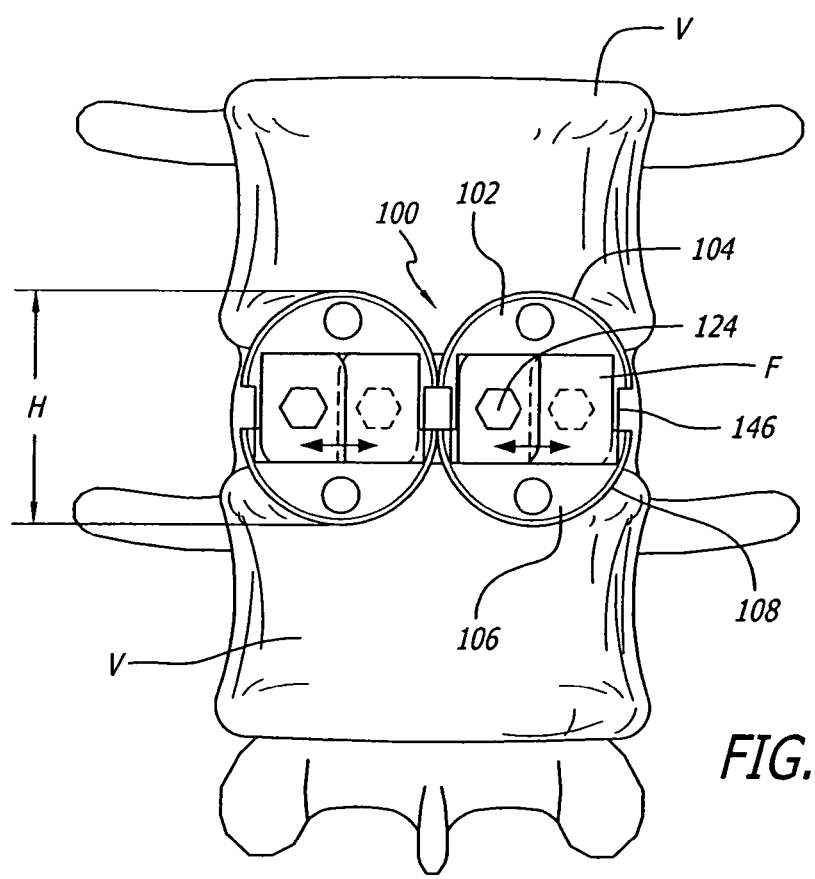
FIG. 13 is a trailing end view of the anterior aspect of two adjacent vertebral bodies and two implants of FIG. 1 implanted therebetween in a final position.

Expander 122 in the present embodiment is adapted to rotate in a single direction approximately 90 degrees to move from an initial (first) insertion position I, as best shown in FIGS. 1, 3 and 10, to a final (second) deployed or expanded position F, as best shown in FIG. 13, to increase the maximum height H of implant 100. Expander 122 preferably rotates in a plane perpendicular to the longitudinal axis L of implant 100 to increase the maximum height H of implant 100. During rotation, expander 122 remains in the same perpendicular plane relative to the longitudinal axis L of the implant. It is appreciated that an expander within the scope of the present invention may be designed to: rotate in either direction or both directions; rotate more than 40 degrees and less than 140 degrees; rotate more or less than 90 degrees; or rotate in a plane other than perpendicular.

Expander 122 has an opening 124 adapted to cooperatively engage a tool (not shown) used to rotate expander 122 to increase height H of implant 100. Opening 124 is adapted to cooperatively engage a tool that preferably rotates about an axis parallel to the longitudinal axis L of implant 100 to rotate expander 122 to increase height H of implant 100. Opening 124 also may be used as a passageway to pass fusion-promoting substances through expander 122 and into implant 100. It is appreciated that the expander may also include a projection, a detent, or any other configuration in place of or in addition to an opening so as to cooperatively engage a tool to move the expander.

In an alternative embodiment, expander 122 could have cutouts along any portion of its perimeter not involved in the actual rotation as shown in FIG. 1A. In another alternative embodiment, a blocker 121 having cutouts along a portion of its perimeter can be positioned into the implant as shown in FIG. 1B. The cutouts can be used to engage a raised area within the implant to lock blocker 121 or expander 122 into position or be used by the surgeon to grasp blocker 121 with a tool that cooperatively engages the cutouts to facilitate inserting blocker 121 into the implant. Rather then having an opening, a projection, a detent, or a central aperture, blocker 121 alternatively could have two or more recesses or holes placed on or through the proximal face to engage a tool as shown in FIG. 1C.

Figure 14:
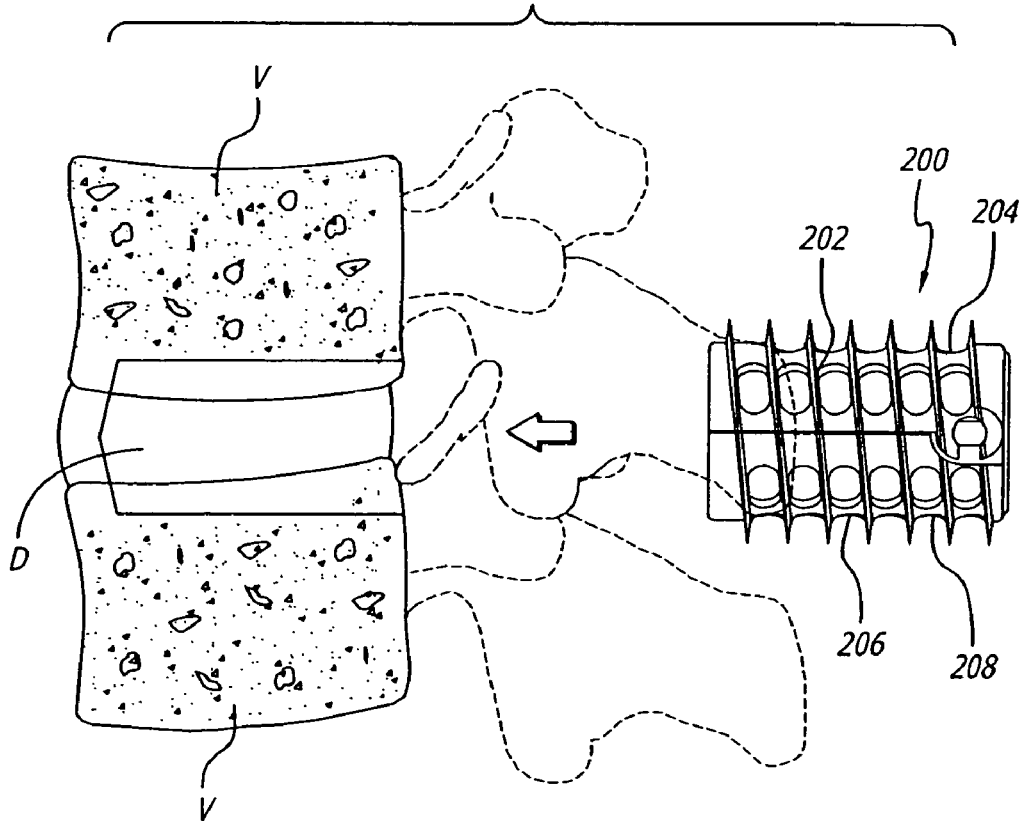
FIG. 14 is a cross-sectional side view of an implantation site formed posteriorly across the disc space between two adjacent vertebral bodies and a second embodiment of an implant of the present invention for posterior insertion being installed into the implantation site.
Figure 15:
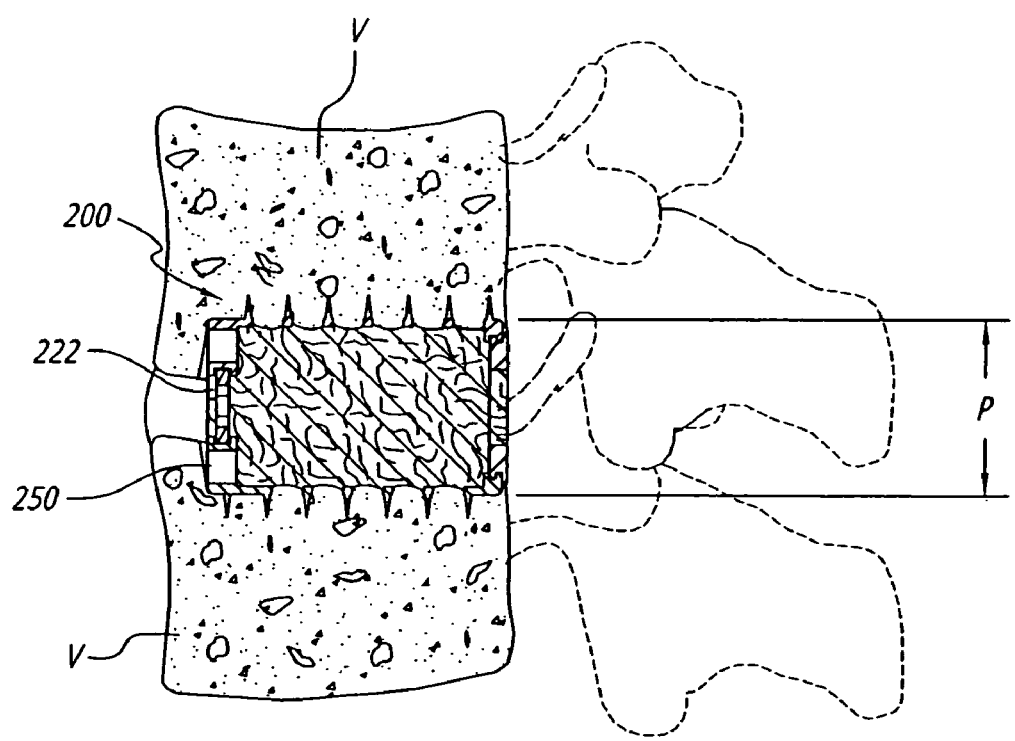
FIG. 15 is a cross-sectional side view of the implantation site formed across the space between two adjacent vertebral bodies and the implant of FIG. 14 installed into the implantation space.
Figure 16:
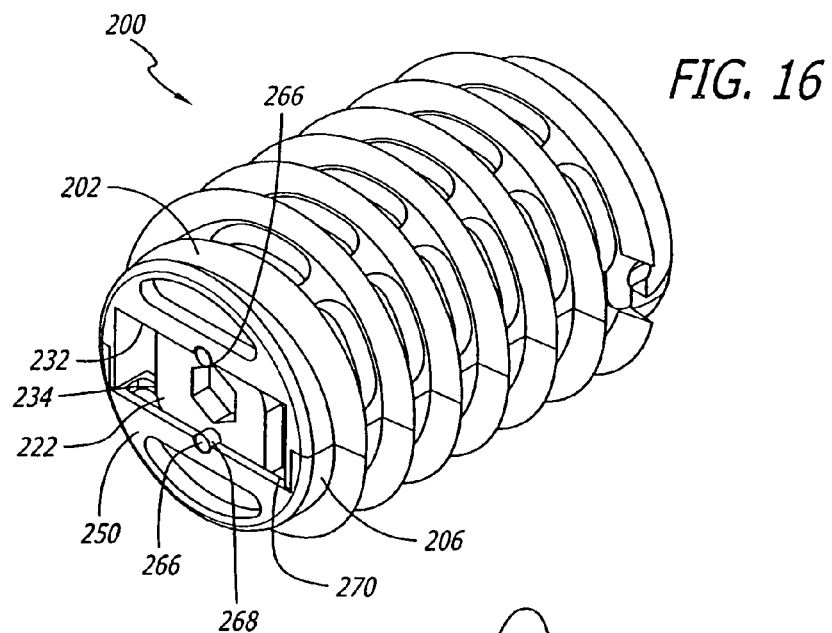
FIG. 16 is a leading end perspective view of the implant of FIG. 14.

As shown in FIGS. 1, 6, 7, 10, 12A-12C, and 13, in one preferred embodiment of the present invention for anterior insertion, expander 122 is located proximate the trailing end 126 of upper and lower members 102, 106. While in a second embodiment as shown in FIGS. 14-16 for posterior insertion expander 222 is located proximate the leading end 250. As shown if FIGS. 17-19, in third and fourth embodiments of the present invention for anterior insertion and possible use together, expanders 322 are located proximate each of leading and trailing ends 350, 326 of implants 300.

Implant 100 preferably has an interior surface 128 and a hollow 130 defined therein. Expander 122 of the present embodiment is located proximate interior surface 128 and more particularly proximate interior surface 128 at trailing end 126 of upper and lower members 102, 106. As is preferred, hollow 130 between the ends is unobstructed by expander 122 so as to allow for the unimpeded loading of the interior of the implant with the desired fusion-promoting substances; thus, loading the implant is easy. Further, this preferred configuration of implant 100 makes available all of the volume of the hollow to contain fusion-promoting substances and so as to permit for the growth of bone directly through the hollow unobstructed by the expander to adjacent vertebral bodies V. Unobstructed hollow 130 further allows for packing implant 100 with fusion-promoting substances. It is appreciated that depending on the intended results, the expander also may be located at distal end 126 or leading end 150 of upper and lower members 102, 106 or anywhere else within the implant. The unobstructed hollow preferably has no mechanism extending along the longitudinal axis of the implant when finally deployed and the mechanism that moves the implant from a first position to a second position preferably does not move expander 122 longitudinally through the hollow portion. The expander may work by pivoting on a surface in contact with an interior wall portion of at least one of the upper and lower members 102, 106. Moreover, multiple expanders may be used in contact with upper and lower members 102, 106 at any location within the implant.

An alternative embodiment of an expander used with the present invention includes an expander having an external thread that cooperates with converging threaded portions of the upper and lower members 102, 106 to expand the implant as the expander is rotated into position. Another alternative embodiment of an expander includes an expander having a cam configuration to expand the implant upon rotation.

The mechanism or tool used to move the expander is not part of the implant itself as the mechanism or tool is removed from the implant upon moving the expander, for example, such as to rotate it into place and thus expand the implant to the final expanded position.

Figure 11:
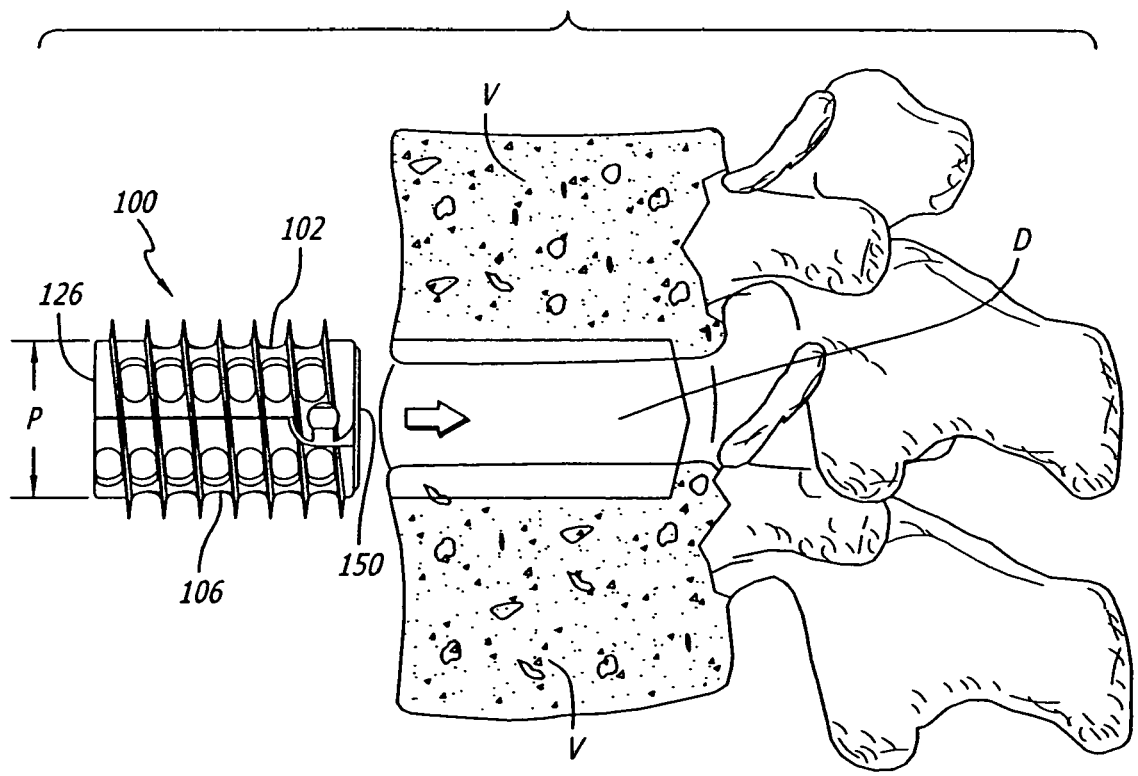
FIG. 11 is a side view of the implant of FIG. 10 being inserted from a generally anterior approach to the spine into an implantation site formed across a disc space and two adjacent vertebral bodies of the spine shown in partial cross-section.
Figure 12A:
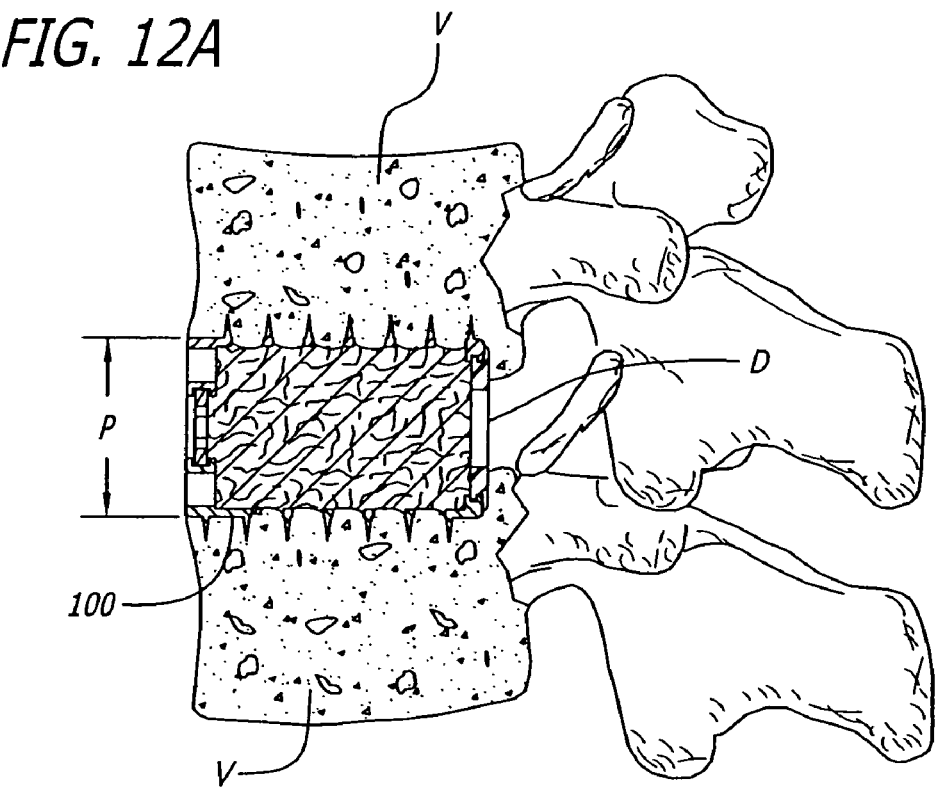
FIG. 12A is a cross-sectional view of the implant of FIG. 1 inserted in an implantation site formed across the disc space and two adjacent vertebral bodies of the spine.
Figure 12B:
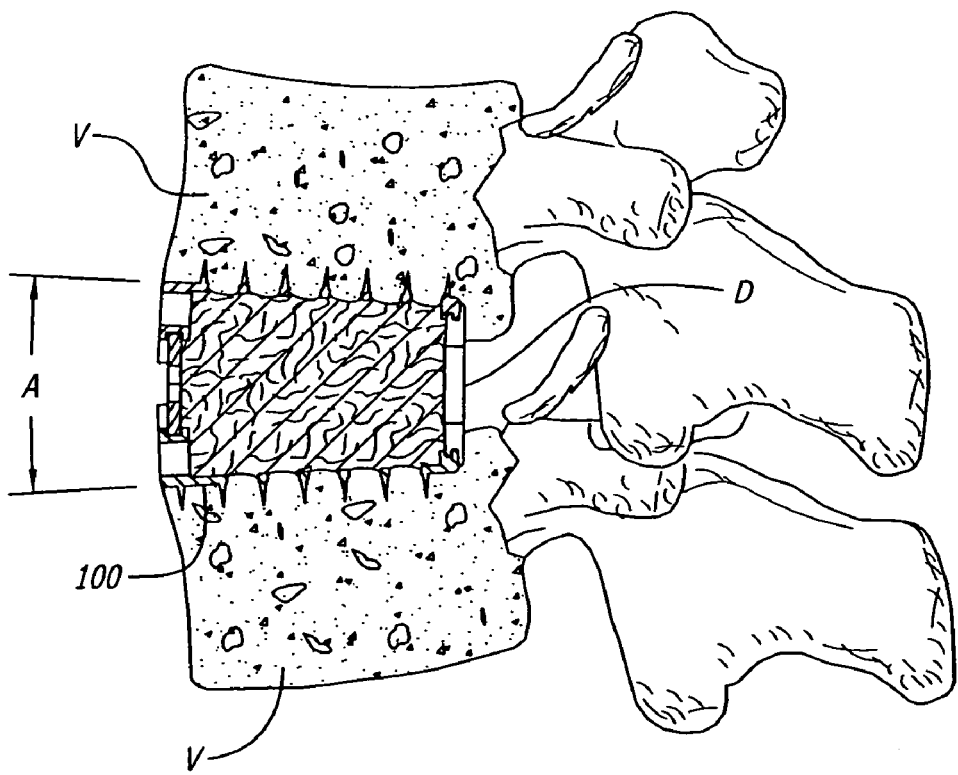
FIG. 12B is a cross-sectional view of the implant of FIG. 1 inserted in an implantation site of FIG. 12A and expanded to place the adjacent vertebral bodies in proper lordosis.

Expander 122 of the present embodiment moves arcuate portions 104, 108 of upper and lower members 102, 106 from a parallel orientation P, as shown in FIGS. 1 and 11 where implant 100 has a generally circular cross section in a first position at trailing end 126, to an angled orientation A, as shown in FIG. 12B where implant 100 has a generally oblong cross section at trailing end 126, in a second position. The implant need not be a true cylinder as a cross section need not form a complete circle having portions of the perimeter absent, less round, flattered, or other. It is appreciated that the expander also may move the arcuate portions of the upper and lower members from a first height at each end to a second and greater height at each end.

In this embodiment, each of upper and lower members 102, 106 structurally cooperate with expander 122 so as to keep it located so as to function for its intended purpose. Each of upper and lower members 102, 106 of the implant of FIG. 1 has a track 132, 134 within which expander 122 rotates. As best shown in FIGS. 1 and 13, track 132, 134 is configured to permit expander 122 to rotate therein and then to move from side to side within track 132, 134. Track 132 of upper member 102 and track 134 of lower member 106 are in the same plane and the plane is perpendicular to the longitudinal axis of implant 100. It is appreciated that the track of the upper and lower members may be in different planes. Such a track design may be used with an expander with a step in it or with offset tabs to engage tracks in different planes than one another. As with the expander, the tracks also may be at various angles to the longitudinal axis of the implant including parallel with the longitudinal axis of the implant. Other means for respectively engaging the implants and the expander position thereof are anticipated and within the scope of the present invention.

Figure 9:
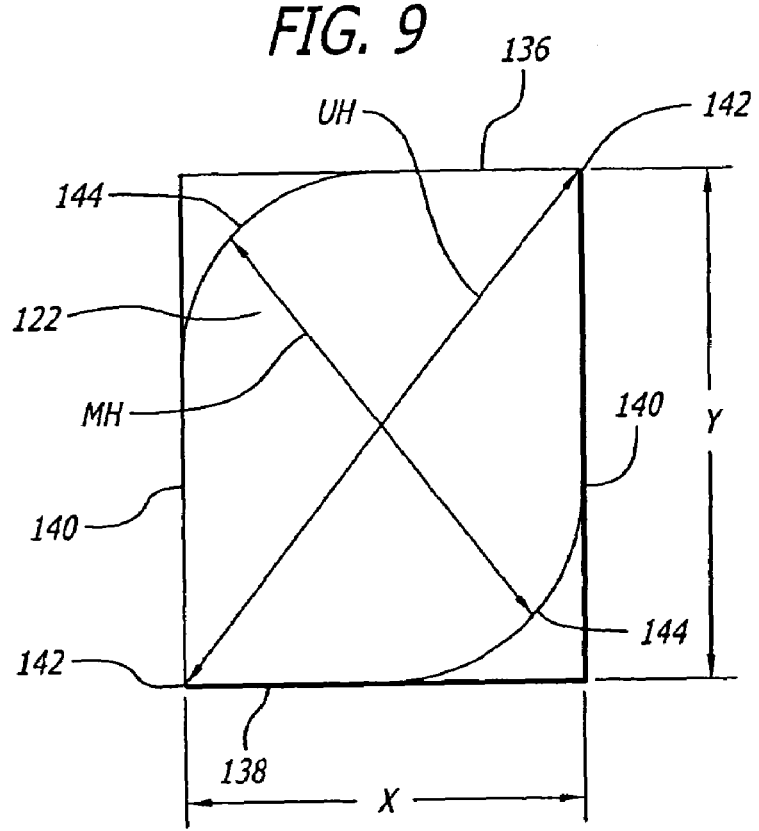
FIG. 9 is a schematic representation of a geometric configuration of a cross-section of an expander in accordance with one embodiment of the present invention.

In rotating the expander, the longer dimension of the expander is substituted for the lesser dimension of the expander thus correspondingly increasing the maximum height of the implant from the first to the second position. As best shown in FIG. 9, the schematic representation of a geometric configuration of a cross-section of an expander 122 in accordance with one embodiment of the present invention, includes: a first dimension X corresponding to the height of expander 122 when implant 100 is initially inserted into the spine and to the width of expander 122 when expander 122 is rotated to increase height H of implant 100; and a second dimension Y corresponding to the width of expander 122 when implant 100 is initially inserted into the spine and to the height of expander 122 when expander 122 is rotated to increase height H of implant 100. Second dimension Y is greater than first dimension X. Expander 122 has an upper surface 136, a lower surface 138, and side surfaces 140 as defined when expander 122 is positioned after rotation to increase height H of implant 100. As used herein, the term "side surfaces" refers to those portions of expander 122 that extend from upper member 102 to lower members 106 after expander 122 has been rotated into its final deployed, or second position to increase the height H of implant 100. The "upper" and "lower" surfaces refer to those portions of expander 122 that are in contact with upper and lower members 102, 106 when implant 100 is in its second position and configuration and is fully expanded.

A preferred expander 122 is in the form of a modified rectangle or rhomboid. The expander generally has a longer dimension Y and a shorter dimension X. When the expander is inserted into a first position, the short dimension X spans the distance between upper to the lower members 102, 106 and when expander 122 is in the second position, the longer dimension Y of expander 122 spans the distance between upper and lower members 102, 106.

Expander 122 in one embodiment of the present embodiment has a cross-section with side surfaces 140 interesting upper and lower surfaces 136, 138 at two junctions which may be diametrically opposed corners 142 and two diametrically opposed arcs 144. Arcs 144 are preferably each of the same radius and the modified hypotenuse MH between opposed arcs 144 generally approximates the distance between upper and lower surfaces 136, 138 such that, when expander 122 is rotated from an initial insertion position toward a final deployed position, no substantial over-distraction occurs between adjacent vertebral bodies V.

The modified hypotenuse MH of this embodiment of the present invention may be equal, slightly less than, or slightly greater than dimension Y of expander 122. Having the modified hypotenuse MH be slightly greater than the dimension Y offers the advantage of having expander 122 stabilized by an over-center position, such that more energy would be required to derotate the expander than for it to remain in the deployed or second position. By "without substantial over-distraction" what is meant is that the modified hypotenuse MH length is closer to the expander dimension Y than to the unmodified hypotenuse UH; and is selected to allow the implant to preferably operate in the range of elastic deformation of the tissues about the operated disc space. Corners 142 may form, but not necessarily, a 90-degree angle and have an unmodified hypotenuse dimension UH.

By way of example, consider one embodiment of expandable implant 100 of the present invention having an optimum expanded height of 18 mm for a given implantation space. Any implant bigger than 18 mm should not be used in this implantation space because during expansion of the implant, its height would move through the range of elastic deformation of the surrounding tissues and after that the implant would crush the vertebral bone or tear ligaments. Inserting an expander such that when the implant is fully expanded allows the implant to be 18 mm would be ideal. It may be that an implant having a 17.5 mm expanded height for this implantation space is nearly as good, but a 16 mm expanded height may be too short to fit tightly within the implantation space.

Using a preferred rectangular expander without any modification to the hypotenuse that is adapted to expand the implant to the optimum 18 mm final height would require the expander to have a hypotenuse causing the implant to exceed the 18 mm expanded height temporarily during rotation of the expander. So turning the expander without a modified hypotenuse would break the vertebrae or tear the ligaments. In reverse, if one could not expand the implant to more than 18 mm without causing damage to the spine, then an implant selected to have an expander having a full unmodified hypotenuse so as to upon rotation temporarily cause the implant height to be 18 mm would in the finally expanded position allow the implant height to collapse such that there would be insufficient height for the implant to adequately distract the implantation space. Generally, the modified hypotenuse of the expander is closer in length to dimension Y of the expander than to the unmodified hypotenuse.

As best shown in FIG. 1 in this particular embodiment, expander 122 has a depth dimension Z that is less than that of first and second dimensions Y, X. Expander 122 of the present embodiment has a fixed shape during movement from initial insertion position I to final deployed position F within implant 100.

Figure 22A:
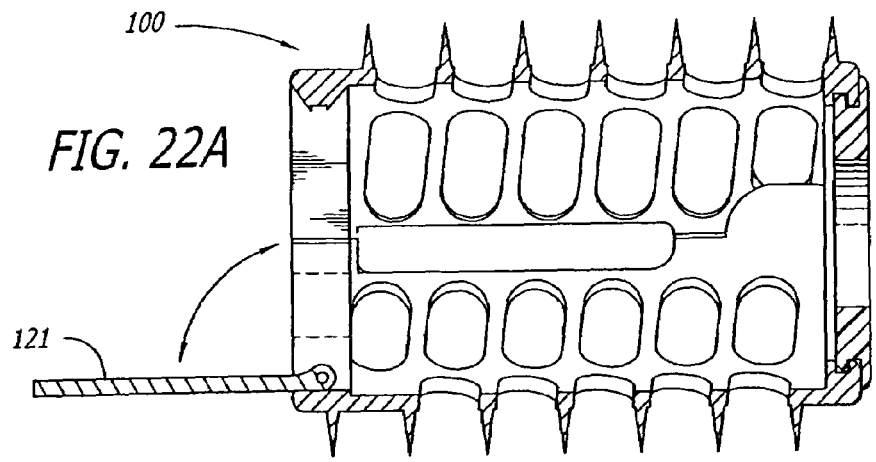
FIG. 22A is a cross-sectional side view of an alternative embodiment of an implant of the present invention with a pivoting trailing end that is also a blocker in the trailing end opening position.
Figure 22B:
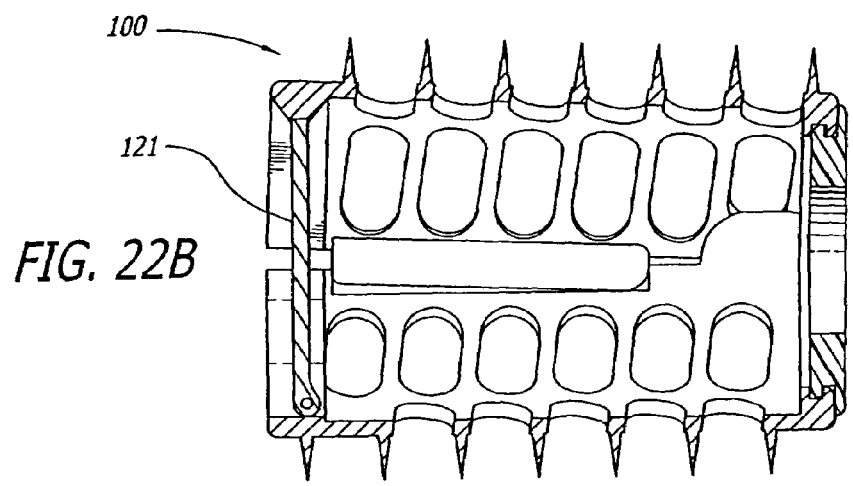
FIG. 22B is a cross-sectional side view of an alternative embodiment of an implant of the present invention with a pivoting trailing end that is also a blocker with the trailing end in the closed position.
Figure 23:
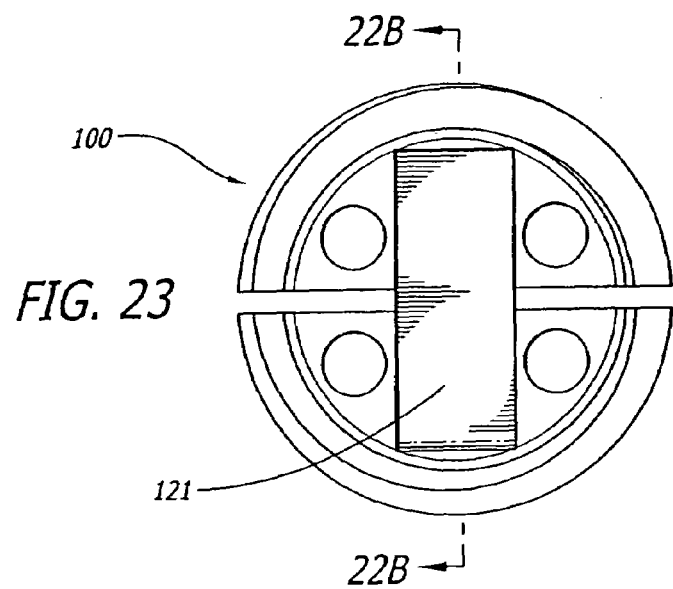
FIG. 23 is a trailing end perspective view of the implant of FIG. 22B.

As shown in FIGS. 22A, 22B, and 23, blocker 121 may also take the form of a trailing wall that articulates or hinges to the inside of implant 100. The trailing wall may be left open during insertion of implant 100 so as to trail behind the upper and lower members. The trailing wall does not protrude outside of a projection rearward of the circumference of implant 100. Once implant 100 is implanted into position, the trailing wall is rotated about one of its ends and pushed into position and locked into place. This may occur by having the trailing wall contact an inclined plane that leads up to a notch into which the trailing wall locks into place. The trailing wall itself may also have at least one opening in it to permit the further loading of fusion-promoting materials into implant 100.

While modified hypotenuse MH is illustrated as being between arcs 144 in this preferred embodiment, the configuration of expander 122 to form modified hypotenuse MH can take many forms, such that those junctions are relieved so as to have the desired lesser dimension therebetween, including arcs, chamfers, a series of angled surfaces, or any other shape so long as the modified hypotenuse MH is sufficiently reduced in dimension to function for the intended purpose according to the present teaching.

An embodiment of the present invention where modified hypotenuse MH is slightly greater than height Y offers the advantage of an over-center effect that locks expander 122 into place. In this instance, once expander 122 rotates past the diagonal of the modified hypotenuse MH, more force would be required to rotate it back from the final deployed position to its insertion position than in an embodiment where modified hypotenuse MH is equal to or less than height Y. Preferably, expander 122 offers a surgeon multiple sensory advantages including: the tactile feel of expander 122 going over center and locking into place; the visual of the handle of a tool rotating expander 122 such that the tool handle goes from perpendicular to parallel, the reverse, or other, to the disc space into place; and auditory from the sound of expander 122 snapping into place.

Each of upper and lower surfaces 136, 138 of expander 122 of the present embodiment lie generally in a plane and are generally parallel to one another. For any implant it is anticipated that a physician may be able to select from a series of blockers or expanders allowing for varying the increase in the implant height. Side surfaces 140 and upper and lower surfaces 136, 138 are oriented so as to substantially form a parallelogram. Any of a number of configurations for the expander for increasing the height of the implant is possible, based on the teachings of the present application and such configurations as would be known to one of skill in the art are anticipated within the scope of the present invention.

The implant may preferably have an overlapping step-cut wall junction between upper and power members 102, 106 which offers the advantage of increasing the lateral rigidity of implant 100 holding the implant in the closed first position until expanded, and to the extent desired retaining the fusion-promoting materials within. The wall junction may be either solid or perforated. As best shown in FIG. 1, upper member 102 in one embodiment of the preferred invention has interior walls 146 extending from each side of arcuate portion 104 toward lower member 106. Interior wall 146 is aligned parallel to longitudinal axis L of implant 100. Lower member 106 has an interior-contacting surface 148 adapted to contact or receive interior wall 146.

In a preferred embodiment, upper and lower members 102, 106 are articulated to one another so one of the respective ends of upper and lower members 102, 106 remain articulated while the other of the respective ends of upper and lower members 102, 106 are free to move away from one another. In a preferred embodiment the articulating means is achieved without a third member such as an axle shaft passing through the implant. The articulating means preferably is formed into the implant walls themselves in such a way that the two implant halves may be articulated when the halves are at 90 degrees to each other and there the halves are moved toward each other for insertion into the implantation space in the spine. The two halves are closed much like the cover of a book. The halves are locked together such that disarticulation will not occur when the implant is assembled for use. Any of a number of ways of articulating or joining upper and lower members 102, 106 is possible.

As best shown in FIG. 1 in this embodiment, upper and lower members 102, 106 of the present embodiment have a pivot point between adjacent distal ends 126 or leading ends 150 of upper and lower members 102, 106. The pivot point in the present embodiment is at the end of implant 100 opposite expander 122. The pivot point of the present embodiment operates as a hinge or axle 152 but is formed out of the walls themselves so as to preferably not intrude into the implant interior or hollow or to block access thereto. Hinge 152 includes a projection 154 extending radially from each side of arcuate portion 108 of lower member 106 and a slotted bracket 156 extending from each side of arcuate portion 104 of upper member 102 for engaging projection 154. Brackets 156 and projections 154 are configured such that engagement occurs when upper and lower members 102, 106 are substantially perpendicular to one another. Brackets 156 and projections 154 are configured so as not to disengage within a range of movement of upper and lower members 102, 106 that would occur when the implant is in use either during insertion or resulting from the expansion in height of implant 100.

Figure 12C:
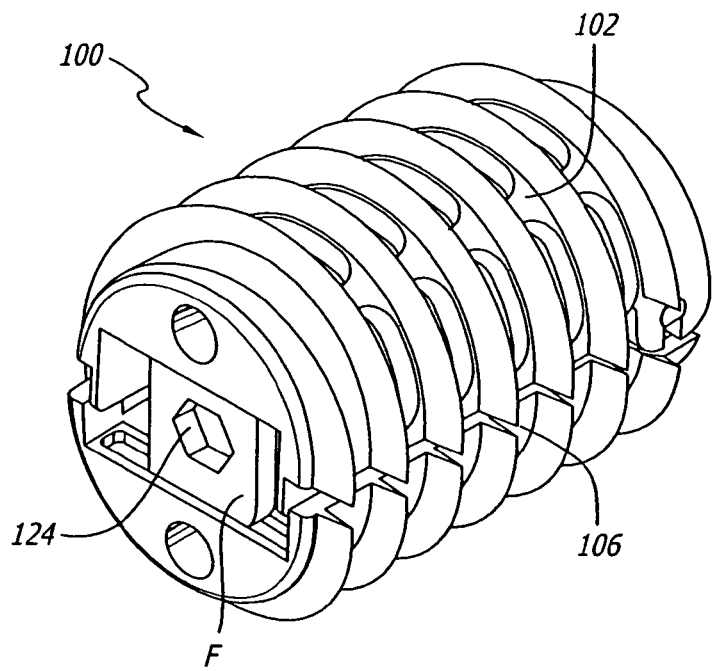
FIG. 12C is a trailing end perspective view of the implant of FIG. 1 with the implant in an expanded position.

As best shown in FIG. 11, interior wall 146 of upper member 102 of the present embodiment is unexposed when implant 100 is in initial insertion position I. As shown in FIG. 12C, when implant 100 is in the expanded position F, implant 100 has a shape such that each of arcuate portions 104, 108 of upper and lower members 102, 106 are separated by at least a portion of interior wall 146, which in this position has an exposed side. The exposed side of the present embodiment is smooth and flat.

Figure 8:
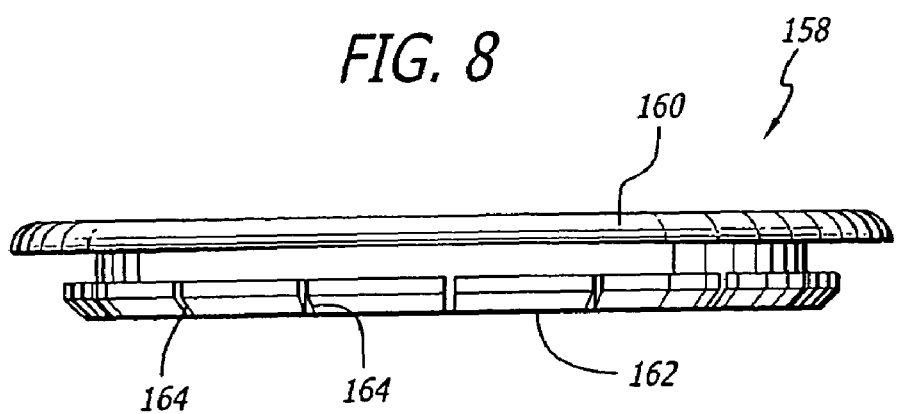
FIG. 8 is a side elevation view of an end cap for use with the implant of FIG. 1.

As best shown in FIG. 8, a cap 158 having an exterior surface 160 and an interior surface 162 is used to close leading end 150 of implant 100. Interior surface 162 of cap 158 has spaced slots 164 about its circumference to facilitate a snap fit between cap 158 and implant 100. Cap 158 and implant 100 can of course be adapted for either or both ends of implant 100.

As discussed above, implant 100 has a leading end 150 and a trailing end 126. One of the ends preferably has a tool-engaging portion. This tool-engaging portion is adapted to engage an insertion tool that holds and rotates implant 100 into position. The tool-engaging configuration may be an opening, and more particularly an opening that is along the longitudinal axis of the implant to facilitate the use of an insertion tool that rotates implant 100 into an inserted position. Of course, the tool-engaging portion need not be an opening. A hole or a blind hole, threaded or otherwise, is preferred in another embodiment. In another preferred embodiment the opening preferably is a threaded slot that functions to cooperatively engage and disengage a tool for use in inserting implant 100. The opening either alone on the proximal end of implant 100 or in conjunction with other openings on the proximal end function to hold fusion-promoting material in implant 100 while permitting vascular access and bone growth through the opening or openings.

Implants of the present invention may have an end adapted to cooperatively engage an implant driver. The anterior approach implant may have a leading end, trailing end, or both ends that are adapted to engage a cap. One of the purposes for that cap includes restricting the passage of fusion-promoting substances so that they remain loaded within the implant. Another purpose of the cap may be to add structural support to the implant. The cap may be solid or it may have openings therethrough. Any such openings could allow for the loaded material to stay within the implant while providing for vascular access to allow for the ingrowth of blood vessels and the growth of bone through the end of the implant.

For a posterior approach implant the cap may be on either or both ends. The trailing end of the implant in a posterior approach implant has direct exposure to the spinal canal where the spinal cord and nerve roots are located. A cap on a posterior approach implant may be for the purpose of sealing off the spinal canal from the fusion-promoting substances contained in the hollow interior of the implant so that no bone grows into the canal. Further, the present invention implant may be used in combination with chemical substances and/or compounds applied at the trailing end of the implant to inhibit scar formation, and the cap may be of benefit in shielding the fusion-promoting substances contained in the implant from these scar formation inhibiting chemicals and compounds. It may also be for the purposes identified herein used in association with the leading end cap of an anterior approach implant.

Shown in FIGS. 14-16, in accordance with the present invention, as embodied and broadly described herein, is a second embodiment of an expandable threaded artificial interbody spinal fusion implant 200 for posterior insertion across a disc space D between two adjacent vertebral bodies V of a human spine. Threaded implant 200 of the present invention includes an upper member 202 having an arcuate portion 204 adapted for placement toward and at least in part within the upper of the adjacent vertebral bodies V and a lower member 206 having an arcuate portion 208 adapted for placement toward and at least in part within the lower of the adjacent vertebral bodies V. Implant 200 in FIGS. 14 and 15 is shown being implanted into the spine from the posterior aspect with expander 222 on the distal end 226 or leading end 250 of implant 200. While anterior and posterior aspect approaches have been illustrated herein, the present invention is not limited to these illustrated approaches. In particular, but not limited thereto, the threaded implant of the present invention also may be used in threaded implants for insertion from the translateral aspect of the spine as disclosed by Michelson in U.S. Pat. No. 5,860,973, which is incorporated herein by reference.

As best shown in FIG. 16, tracks 232, 234 of upper and lower members 202, 206 of the second embodiment have a cooperating surface 266 and expander 222 has a corresponding cooperating surface 268 that contacts cooperating surface 266 of tracks 232, 234 to orient expander 222 in a predetermined location. The cooperating surfaces orient expander 222 within implant 200 such that the axis of rotation of expander 222 is parallel to the longitudinal axis of implant 200 and more particularly center expander 222 within implant 200 such that the axis of rotation of expander 222 coincides with longitudinal axis L of implant 200.

Tracks 232, 234 include sides 270 having cooperating surface 266 and expander 222 has corresponding cooperating surface 268 used to orient expander 122 in a predetermined location. Cooperating surface 266 of side 270 is a detent and corresponding cooperating surface 268 of expander 222 is a projection. The projection preferably projects away from expander 222 in a direction parallel to the longitudinal axis of implant 200. The detent and the projection preferably center expander 222 within implant 200 such that the axis of rotation of expander 222 coincides with the longitudinal axis of implant 200.

Figure 17:
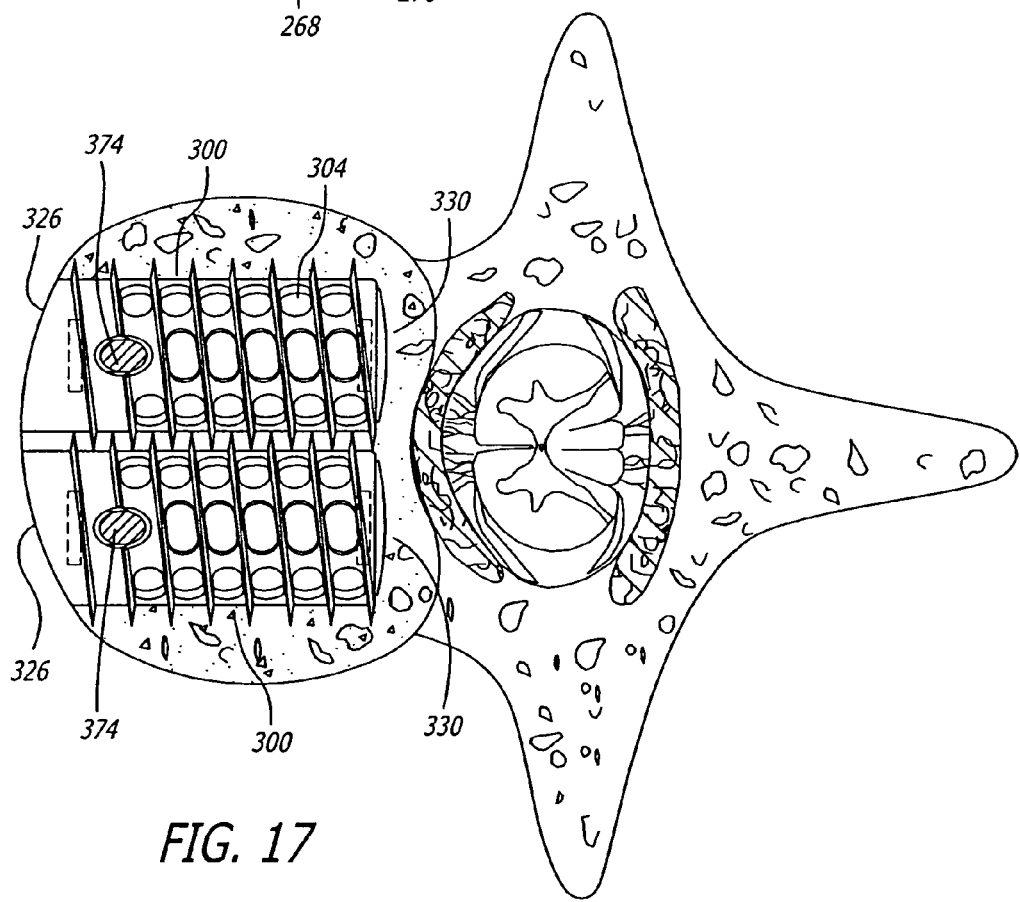
FIG. 17 is a top plan view of another embodiment of the present invention inserted upon the lower vertebral body of an implantation site formed anteriorly across a disc space with the vertebral body shown in partial cross-section.

Shown in FIGS. 17-19, in accordance with the present invention, as embodied and broadly described herein, is a third embodiment of an expandable threaded artificial interbody spinal fusion implant 300 for insertion across a disc space D between two adjacent vertebral bodies V of a human spine. Threaded implant 300 of the present invention includes an upper member 302 having an arcuate portion 626 for orientation toward the upper of adjacent vertebral bodies V and a lower member 306 having an arcuate portion 308 for orientation toward the lower of the adjacent vertebral bodies V.

Implant 300 of the present embodiment may include any of the various features disclosed in association with implant 100 and implant 200 disclosed herein. Implant 300 further includes a side surface 372 contoured to cooperatively receive another implant. See U.S. Pat. No. 5,593,409 by Michelson for a discussion of the advantages associated with placing implants in side-in-side contact.

Another aspect of implant 300 is that its upper and lower members 302, 306 have screw holes 374 passing therethrough adapted to receive a screw 378 passing from the interior of implant 300 into adjacent vertebral bodies V to anchor implant 300 to an adjacent vertebral body V.

Figure 21:
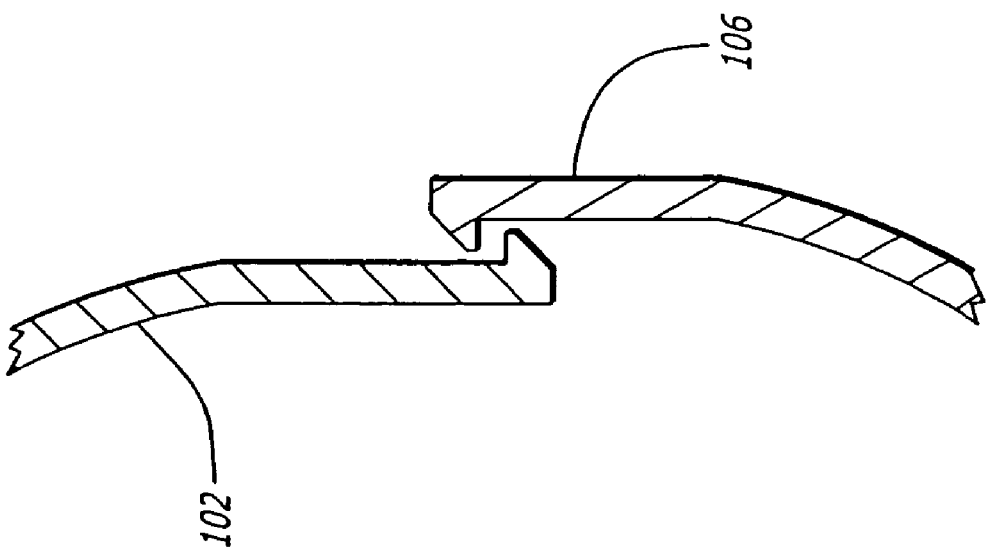
FIG. 21 is a partial cross sectional view of another embodiment of an interlocking wall design along line 21-21 of FIG. 19.
Figure 20:
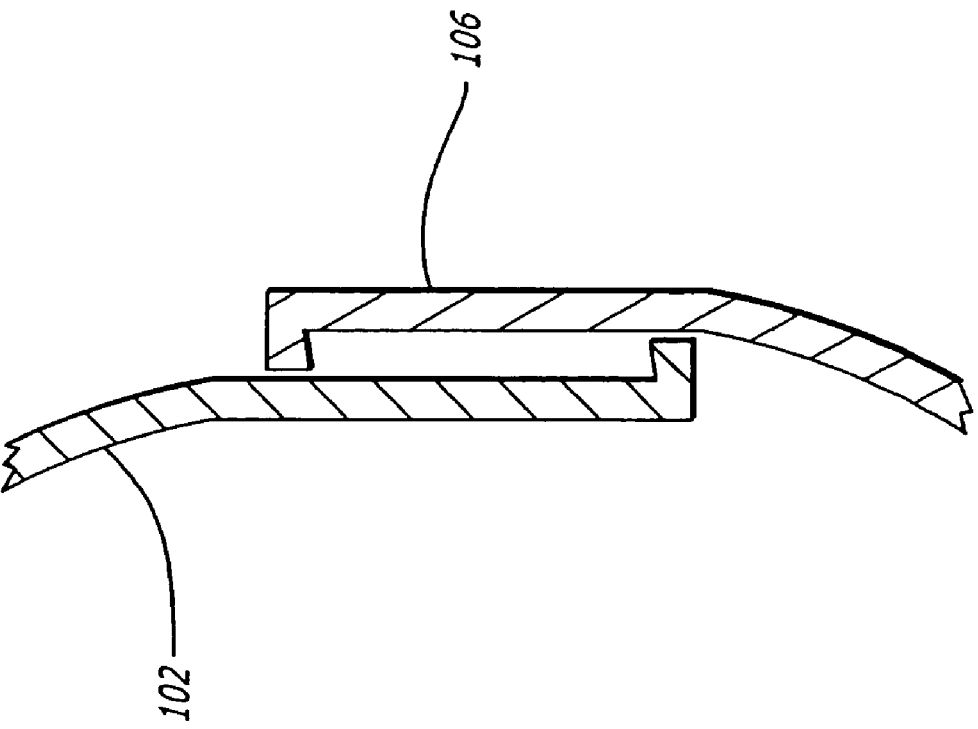
FIG. 20 is a partial cross sectional view of an embodiment of an interlocking wall design along line 21-21 of FIG. 19.

The articulation may be of one of two general types, examples of which are each herein disclosed. As shown in previously described embodiments of the present invention, the articulation may allow rotation about the articulation. A second type of articulation allows for both rotation and expansion at the point of articulation. An example of this is shown in FIG. 19, where a peg and hook design is utilized. While in this example both functions, that is rotation or pivoting, and captured or limited expansion with a fixed end point or stop, occur at the same location. Alternatively, and without departing from the teachings of the present invention, those functions can be divided. By way of example only, and not limitation, expansion can be allowed and controlled by an interlocking wall design, as shown by the interlocking members in the alternative embodiments of FIGS. 20 and 21.

Various other structural features as would be obvious to one of ordinary skill in the art after the teachings herein can similarly be employed.

A fixed end point for the implant expansion is preferred for the proper functioning of the opposed bone screws. A purpose of the opposed bone screws is to rigidly secure the implant within the vertebral segment. A further purpose is to pull each of the adjacent vertebral bodies toward the implant and towards each other so as to have a construct resistant to the deleterious effects of vertebral rocking as may otherwise occur with spinal flexion and extension absent such restraint. If the articulation device captured the upper and lower members together, as in the embodiments of FIG. 1-16, by closely encircling a post then the implant could not expand at that location. So the coupling mechanism of FIG. 19 permits the upper and lower members to remain articulated, permits the implant to expand, and permits the screws to pull against the implant and each other, in opposite directions and to pull the bones toward each other. The optional extended slot and peg configuration on the right-hand side of FIG. 19 illustrated in dashed image lines is not needed to hold the implant together.

In accordance with this embodiment of the present invention, a second expander may be located at least in part between the upper and lower members for moving at least a portion of the upper and lower members away from one another to increase the height of the implant defined by the maximum distance between the arcuate portions of the upper and lower members. All of the features described herein for the expander may also be applicable to the second expander. Additionally, the second expander may be located proximate an end of the implant opposite the other expander, thereby providing an implant capable of being expanded at both ends of implant. The increased height of the implant resulting from moving the two expanders may be the constant or varied along the length of the implant according to the desired configuration of the implant.

Figures 24, 24A:
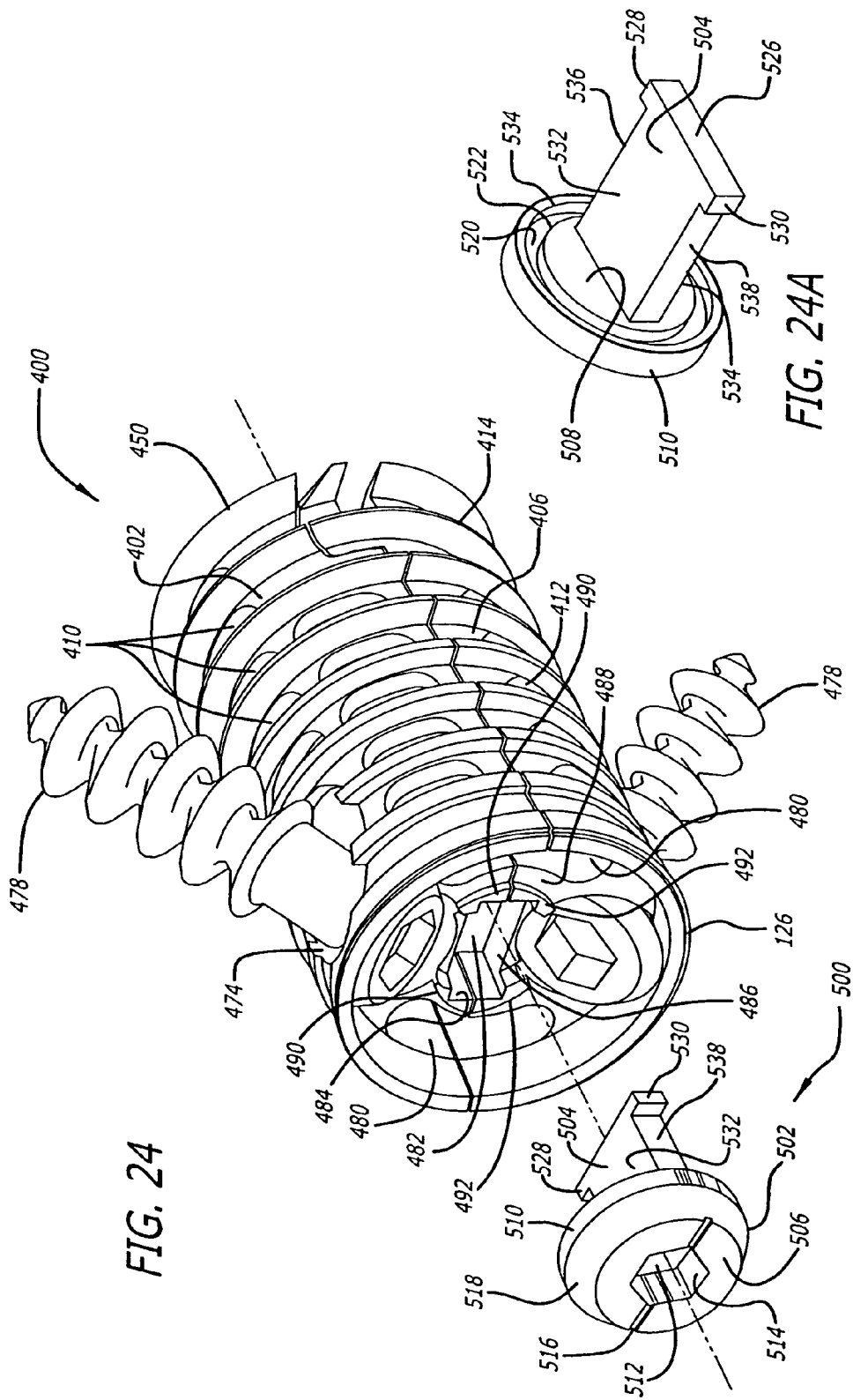
FIG. 24 is an exploded front perspective view of an expandable interbody spinal fusion implant with expanding and locking end cap in accordance with a preferred embodiment of the present invention.
FIG. 24A is a rear perspective view of the end cap of FIG. 24.
Figure 25:
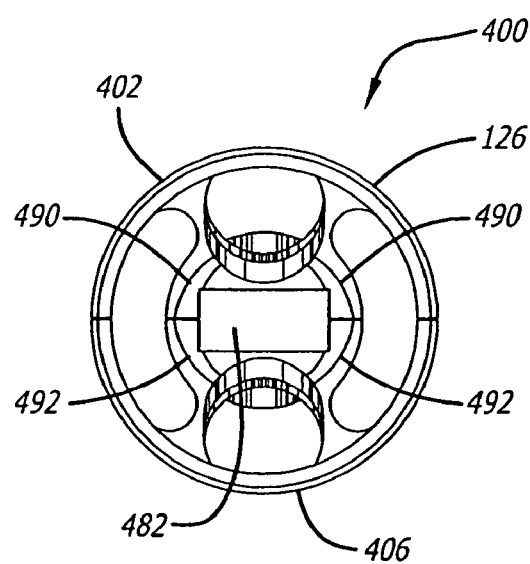
FIG. 25 is a rear elevation view of the implant of FIG. 24.

FIGS. 24-29 show a preferred embodiment of an expandable interbody spinal fusion implant 400 and an expanding and locking end cap 500 for use therewith in accordance with the present invention. As shown in FIGS. 24 and 25, implant 400 preferably has a leading end 450, a trailing end 426, an upper member 402, and a lower member 406. Upper and lower members 402, 406 are each preferably arcuate at least in part and adapted for placement toward and at least in part within the upper and lower of two adjacent vertebral bodies, respectively. Each of upper and lower members 402, 406 preferably have at least one opening 410, 412 in communication with one another for permitting for the growth of bone from adjacent vertebral body to adjacent vertebral body through implant 400. Trailing end 426 preferably includes openings 480 to permit for the growth of bone through implant 400.

Implant 400 has a bone-engaging projection 414 that is preferably an external helical thread to permit for the rotational insertion of implant 400 into the disc space and between adjacent vertebral bodies of a human spine. Although a preferred embodiment of the implant has threads, the invention is not so limited. For example, the exterior of implant 400 may have other bone-engaging projections such as splines, knurling, or other surfaces roughenings to resist expulsion of the implant from the disc space after implantation.

Figure 27:
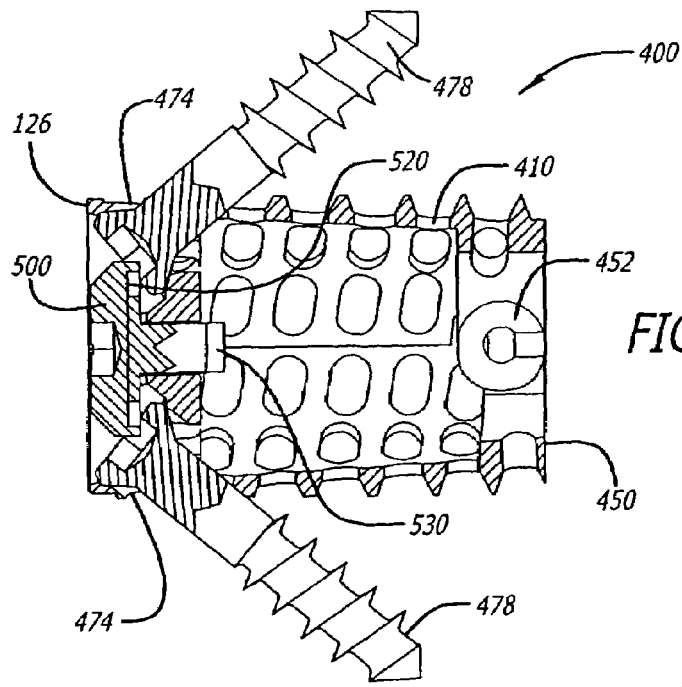
FIG. 27 is a side elevation view in partial cross section of the implant of FIG. 24 in an unexpanded state and end cap inserted therein.
Figure 28:
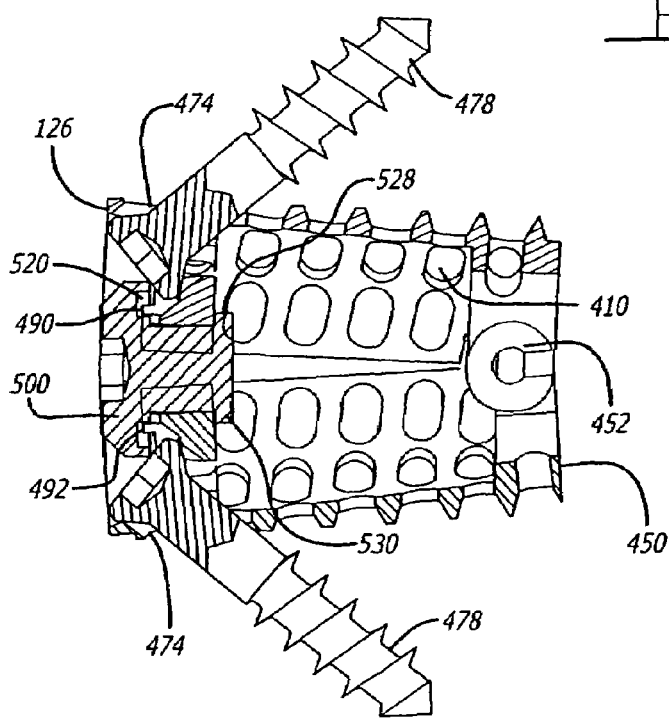
FIG. 28 is a side elevation view in partial cross section of the implant of FIG. 24 in an expanded state and end cap inserted therein.
Figure 30:
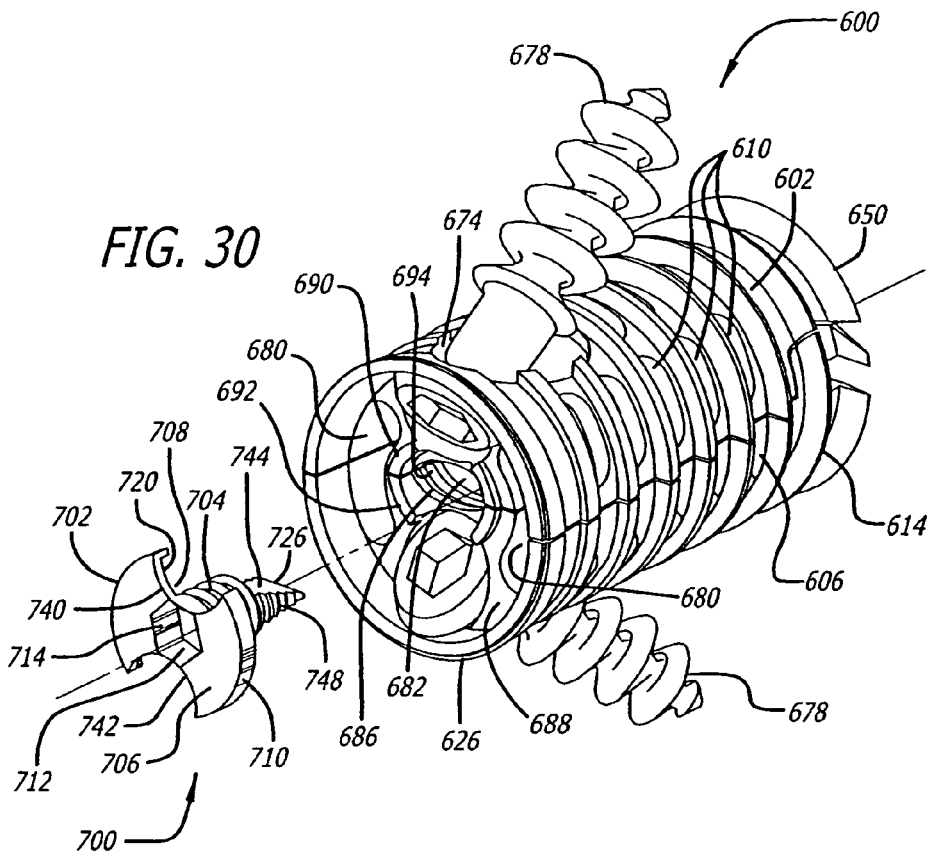
FIG. 30 is a front perspective view of an expandable interbody spinal fusion implant with expanding and locking end cap in accordance with another preferred embodiment of the present invention.
Figure 31:
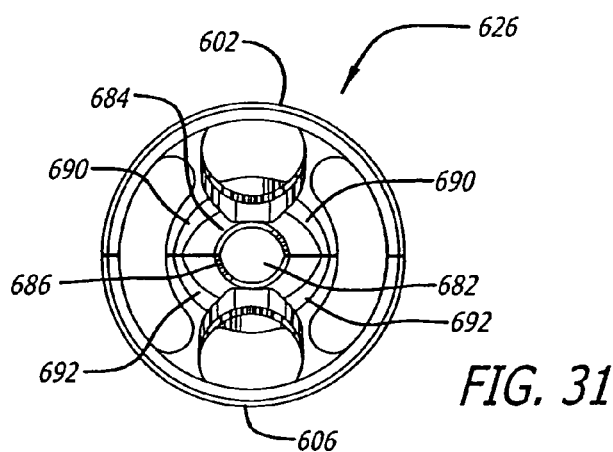
FIG. 31 is a rear elevation view of the implant of FIG. 30.

As shown in FIGS. 27 and 28, by way of example, upper and lower members 402, 406 preferably have a cooperating rotational articulation or pivot point 452 between upper and lower members 402, 406. The cooperating rotational articulation 452 preferably is proximate one of the proximal end and the distal end of upper and lower members 402, 406 at an end opposite to an end cap 500. Upper and lower members 402, 406 preferably have upper and lower screw holes 474 passing therethrough, each adapted to receive a bone screw 478 passing from the interior of implant 400 into an adjacent vertebral body to anchor implant 400 to an adjacent vertebral body. Bone screws are not essential to the operation of the invention, but are preferable for providing added securement of the implant to the adjacent vertebral bodies.

In certain circumstances, upper and lower members 402, 406 can move away from one another and merely securing upper and lower members 402, 406 to the adjacent vertebral bodies with bone screws is not adequate. An example of such a circumstance occurs when the surgeon elects to approach the spine anteriorly, which generally requires severing and/or removing substantial portions of the anterior longitudinal ligament over the operated area. The anterior longitudinal ligament is positioned along the anterior spinal surface and prevents hyperextension of the spine as an individual bends backward. Because the anterior longitudinal ligament covers the anterior spinal surface, the surgeon must cut through this tough ligament to access the disc space below, compromising the stability of the spine. Specifically, the anterior longitudinal ligament is generally lax, except when an individual leans backward, then the ligament acts as a tension band resisting elongation. If the anterior longitudinal ligament is damaged, there is no check on that spinal movement and the vertebral bodies may detrimentally angulate. Thus, a mechanism is needed to prevent movement of the upper and lower members relative to one another beyond a predetermined amount.

FIGS. 24-25 show expanding and locking end cap 500 for use with implant 400. The end cap is capable of one or more of the following functions: (1) expands the implant by moving the upper and lower members apart, (2) maintains the implant in an expanded state by holding at least a portion of the upper and lower members apart so as to maintain the increased height of the implant and resist the collapse of the implant to the collapsed implant height, (3) prevents the implant from expanding beyond a predetermined amount by engaging at least a portion of the upper and lower members, and (4) locks bone screws to the implant by blocking the exit path of the bone screws in a direction opposite to the direction of insertion. Expansion of the implant preferably increases the implant height only, that is in a plane passing through the mid-longitudinal axis of the implant and the upper and lower members. In a preferred embodiment, the end cap is capable of performing all four of the aforementioned functions.

As shown in FIGS. 24 and 25, trailing end 126 of implant 400 preferably has an opening 482 adapted to engage cap 500 and may also provide access to the interior of implant 400 for the purpose of introducing bone growth promoting materials therein. Upper and lower interior surfaces 484, 486 of opening 482 preferably have a portion that extends beyond exterior trailing end surface 488, forming upper lip portions 490 and lower lip portions 492, respectively. When implant 400 is in an unexpanded state, the profile of upper and lower lip portions 490, 492 preferably form the shape of at least a portion of an oval. In the expanded state of implant 400, the profile of upper and lower lip portions 490, 492 preferably becomes less oval and generally more circular in shape. For example, upper and lower lip portions 490, 492 can be arcs of a circle such that in the expanded state, the arcs would be part of the same circle.

Cap 500 has a head 502 and a stem 504. Head 502 has a perimeter preferably sized and shaped to cover at least a portion of upper and lower bone screw holes 474 so as to lock bone screws 478 to implant 400. Head 502 has a top surface 506, a bottom surface 508, and a rim 510. Top surface 506 has a tool engagement area 512 that is preferably adapted to cooperatively engage an insertion tool. Tool engagement area 512 preferably includes a hex-shaped recess 514 and a groove 516 adapted to engage correspondingly-shaped tools, respectively. Other shapes are possible for tool engagement area 512 depending upon the type of insertion tool used with the present invention, all of which are within the broad scope of the present invention.

Top surface 506 of cap 500 preferably has a bevel 518 extending around the perimeter thereof to form a reduced profile. Top surface 506 may have any shape suitable for its intended purpose and it is preferable that such shape does not extend from trailing end 426 so as not to substantially interfere with delicate vascular and neurological structures adjacent thereto after implant 400 is installed in the spine.

As shown in FIG. 24A, bottom surface 508 of cap 500 has a recess 520 proximate the perimeter of bottom surface 508 that is adapted to interact with upper and lower lip portions 490, 492 of implant 400. As described in further detail below, the interaction of lip portions 490, 492 and recess 520 limits the over-expansion of implant 400. Recess 520 has an inner perimeter 522, an outer perimeter 524, and a width therebetween adapted to accommodate the profiles of at least a portion of upper and lower lips 490, 492 of implant 400 in both an unexpanded and expanded state. The surface of outer perimeter 524 forms a flange that acts as a stop against which upper and lower lip portions 490, 492 of implant 400 are prevented from further movement away from the mid-longitudinal axis of implant 400 when implant 400 and cap 500 are engaged, as will be described in more detail below.

Stem 504 of cap 500 projects from bottom surface 508 and is sized and shaped to cooperatively engage opening 482 in trailing end 426 to expand implant 400 and to maintain implant 400 in an expanded state. Stem 504 preferably has a distal end 526 with tabs 528, 530, an upper surface 532, a lower surface 534 opposite to upper surface 532, and sides 536, 538. Tabs 528, 530 are configured to engage the interior surface of trailing end 126 such that when properly positioned within opening 482, tabs 528, 530 prevent cap 500 from backing out of opening 482 of implant 400.

Sides 536, 538 of stem 504 are configured to cooperatively engage upper and lower interior surfaces 484, 486 of opening 482. Opening 482 may have any shape suitable for its intended purpose for interacting with stem 504. For example, sides 536, 538 may be beveled or rounded to accommodate rotational contact with upper and lower interior surfaces 484, 486. Stem 504 may have a generally rectangular cross-section or may have a cross-section with sides 536, 538 intersecting the upper and the lower surfaces 532, 534 at junctions, which may be two diametrically opposed corners and two diametrically opposed arcs. The two diametrically opposed arcs may be each of the same radius and, preferably, the diagonal or modified hypotenuse "MH" between the opposed arcs has a maximum dimension that generally approximates the distance between the upper and lower surfaces 532, 534 such that, when stem 504 is rotated from a first insertion position toward a second/deployed position, no substantial over-distraction occurs between the adjacent vertebral bodies as would occur if the height of the implant was increased markedly beyond that obtained in the second/deployed position. The two diametrically opposed corners may form a 90-degree angle. Additionally, sides 536, 538 may be configured to be divergent away from distal end 526 to better accommodate engagement with upper and lower interior surfaces 484, 486 while implant 400 is in the expanded state.

Figure 26:
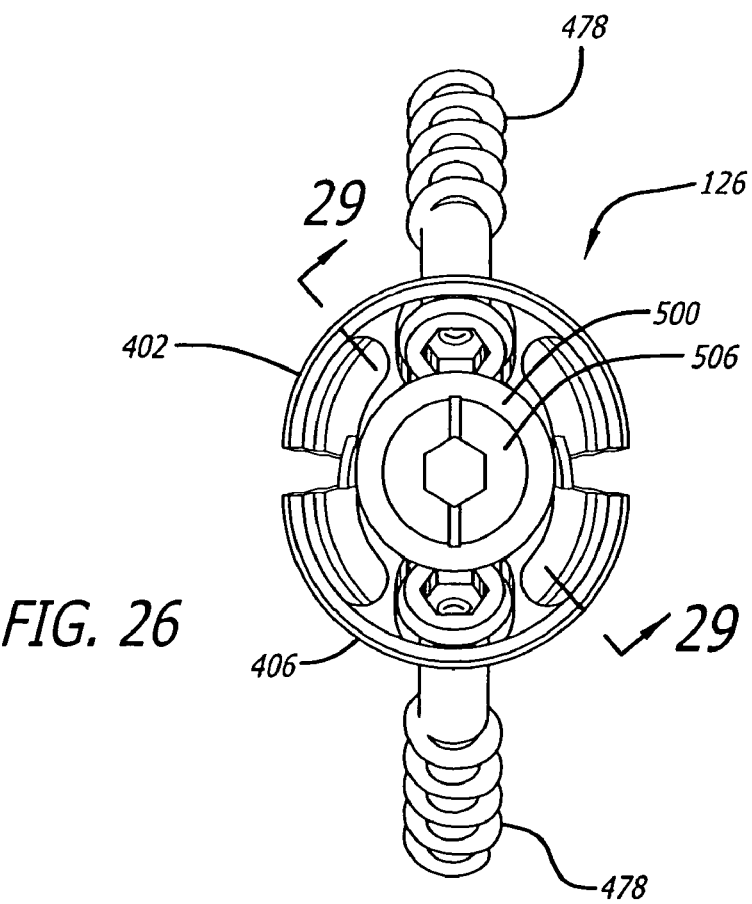
FIG. 26 is a rear elevation view of the implant of FIG. 24 in an expanded state and end cap inserted therein.

FIGS. 26-28 show a preferred expansion of implant 400 by cap 500. In FIG. 27, stem 504 of cap 500 is inserted through opening 482 in trailing end 426 of implant 400. After stem 504 is inserted into opening 482, tabs 528, 530 extend beyond upper and lower interior surfaces 484, 486 of opening 482 and into the interior of implant 400. Upper and lower surfaces 532, 534 of stem 504 are oriented toward upper and lower interior surfaces 484, 486 of opening 482, respectively, such that implant 400 is in a collapsed state. As cap 500 is rotated 90° in either direction, sides 536, 538 of stem 504 cooperatively engage with upper and lower interior surfaces 484, 486 of opening 482, forcing apart upper and lower members 402, 406 away from the mid-longitudinal axis of implant 400 to position implant 400 in an expanded state. The rotation of cap 500 moves upper and lower members 402, 406 from a generally parallel orientation shown in FIG. 27 to an angled orientation shown in FIG. 28. During expansion of implant 400, upper and lower lip portions 490, 492 move within recess 520 of cap 500 until stem 504 ceases moving upper and lower interior surfaces 484, 486 away from the mid-longitudinal axis of implant 400.

Figure 29:
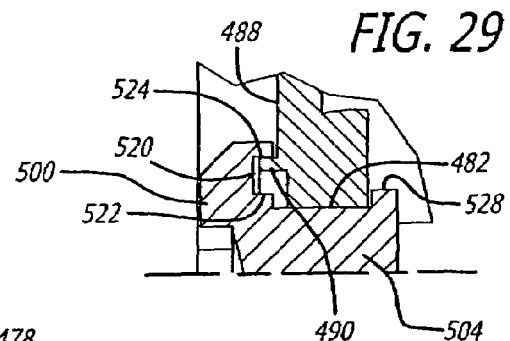
FIG. 29 is a fragmentary cross sectional side elevation view of the implant of FIG. 24 in an expanded state showing a lip portion of the implant trailing end against the outer perimeter of a recess in the end cap for preventing over-expansion of the implant.

FIG. 29 shows a partial cross-section along line 29-29 of FIG. 26. As shown in FIG. 29, the maximum expansion of upper member 402 is reached when upper lip portions 490 are blocked from further motion away from the mid-longitudinal axis of implant 400 upon reaching outer perimeter 524 of recess 520. Although not shown in FIG. 29, lower lip portions 492 similarly contact outer perimeter 524 of recess 520. In this manner, the expansion of implant 400 beyond a predetermined amount is prevented. Tabs 528, 530 of stem 504 bear against the interior of implant 400 and prevent removal of end cap 500 from opening 482. In the deployed position, end cap 500 locks implant 400 in an expanded state.

As shown in FIGS. 30-33, another preferred embodiment of the implant and end cap of the present invention is shown and generally referred to by the reference numbers 600 and 700, respectively. Implant 600 is similar to implant 400, except that opening 682 of implant trailing end 626 preferably has at least one thread 694 for cooperatively engaging with a threaded stem 404 of cap 700.

Cap 700 is similar to cap 500, except for differences noted below. Head 702 includes an upper cutout portion 740 and a lower cutout portion 742, each being adapted to allow the passage of a bone screw 678 into implant 600 after cap 700 has been attached to implant 600. Once bone screws 678 are inserted, cap 500 may be rotated such that at least a portion of head 702 covers each of screws 678. Upper and lower cutout portions 740, 742 allow the surgeon the option of inserting bone screws 678 before or after attachment of cap 700 with implant 600.

Stem 704 has at least one thread 748 along the mid-longitudinal axis of cap 700 for cooperatively engaging with threaded opening 682 of implant 600. Distal end 726 of stem 704 has an upper surface 744 and a lower surface 746 that are convergent towards distal end 726 for assisting in the insertion of stem 704 into opening 682 of implant 600.

Figure 32:
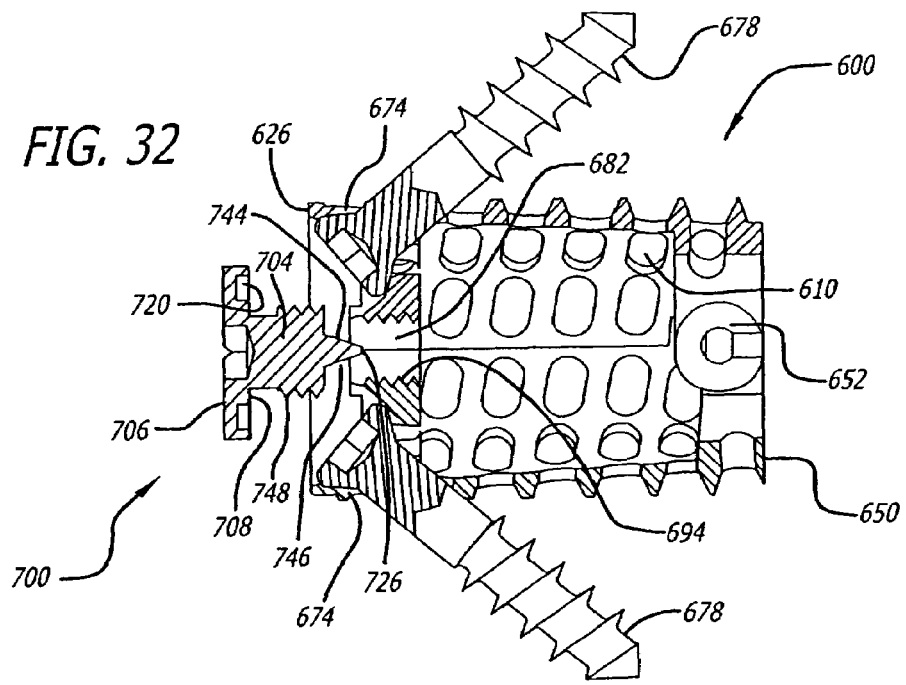
FIG. 32 is a side elevation view in partial cross section of the implant of FIG. 30 in an unexpanded state and end cap being inserted therein.
Figure 33:
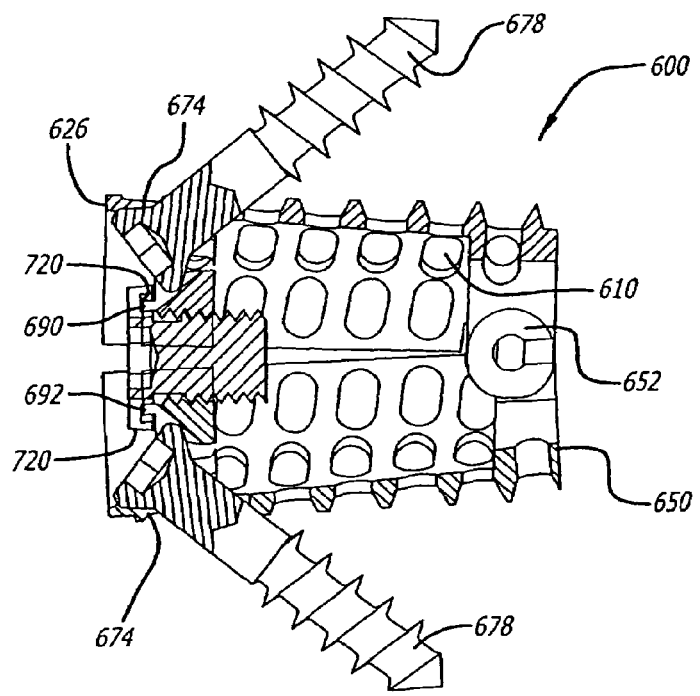
FIG. 33 is a side elevation view in partial cross section of the implant of FIG. 30 in an expanded state and end cap inserted therein.

As shown in FIGS. 32 and 33, cap 700 is inserted into trailing end 626 of implant 600, preferably by aligning the edge of distal end 726 with the plane separating upper and lower members 602, 606. Once upper and lower surfaces 744, 746 of distal end 726 are sufficiently within threaded opening 682 of implant trailing end 626, cap 700 is rotated to allow stem thread 748 of cap 700 to cooperatively engage with threaded opening 682. The engagement of stem thread 748 with threaded opening 682 spreads apart upper and lower members 602, 606 at least along a portion of the length of implant 600. Continued rotation of cap 700 forces upper and lower lip portions 690, 692 to contact recess 720 of cap 700. The pitch of thread 748 is preferably such that as upper and lower lip portions 690, 692 reach recess 720, they come into contact with at least a portion of the outer perimeter of recess 720. Upon contact with recess 720, upper and lower lip portions 690, 692 are prevented from further movement away from the mid-longitudinal axis of implant 600.

Those skilled in the art will appreciate that although it is preferred to use a cap to prevent over-expansion of an expandable implant, the invention is not so limited. For example, the implant trailing end may be adapted to have lip portions along the trailing end interior surface for cooperatively engaging with a recess and/or flange to prevent over-expansion of the implant. In such an instance, an over-expansion inhibiting surface may operate without a stem and/or head by relying on additional surface features of the implant trailing end, for example, a key-way entry along the opening leading to the interior lip portions or a circumferential barrier beyond the interior lip portions for preventing the over-expansion surface from traveling too far into the implant interior. Although the expander implant cap has been described with respect to a threaded expanding spinal fusion implant, it may be adapted for use with any expandable spinal implants including any of the various implant embodiments disclosed herein. Shown in FIGS. 34-36B, in accordance with the present invention, as embodied and broadly described herein, is another embodiment of an expandable threaded artificial interbody spinal fusion implant 800 for anterior insertion across a disc space D between two adjacent vertebral bodies V of a human spine. Implant 800 of the present invention includes an upper member 802 having an arcuate portion 804 adapted for placement toward and at least in part within the upper of the adjacent vertebral bodies V and a lower member 806 having an arcuate portion 808 adapted for placement toward and at least in part within the lower of the adjacent vertebral bodies V. Arcuate portions 804, 808 of upper and lower members 802, 806 in the first position of the present invention are angled to one another and form at least a portion of a frusto-conical shape along the length of implant 800. A bone engaging projection 814, which is preferably formed of at least one thread is on an exterior of each of opposed arcuate portions 804, 808 of upper and lower members 802, 806 for engaging adjacent vertebral bodies V.

Figure 36A:
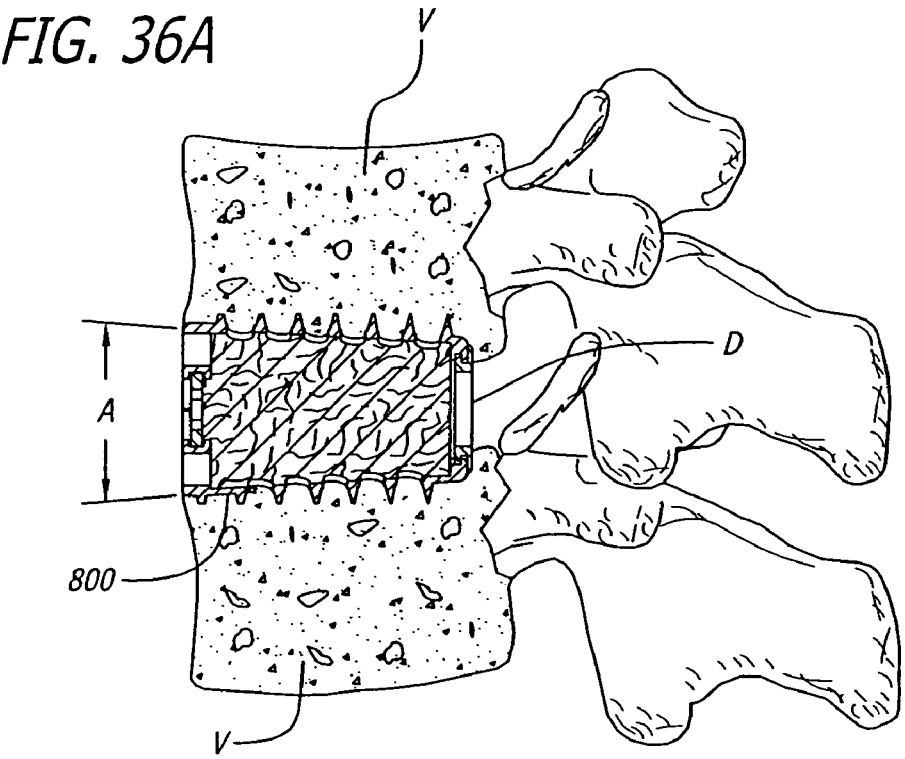
FIG. 36A is a cross-sectional view of the implant of FIG. 35 inserted in an implantation site formed across the disc space and two adjacent vertebral bodies of the spine.
Figure 36B:
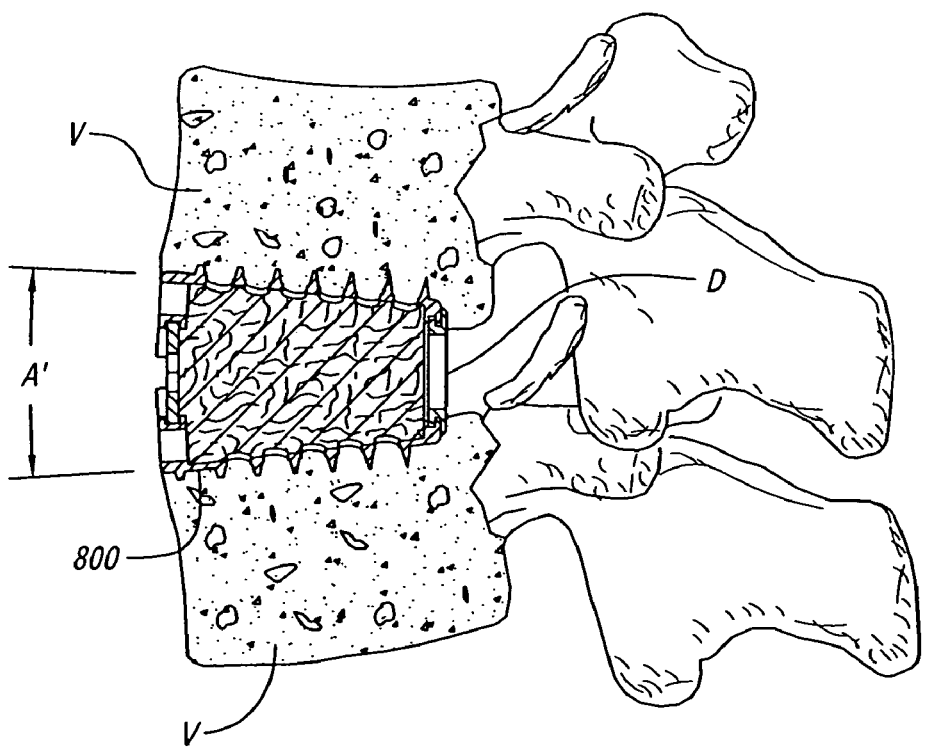
FIG. 36B is a cross-sectional view of the implant of FIG. 35 inserted in an implantation site of FIG. 36B and expanded to place the adjacent vertebral bodies in proper lordosis.

As shown in FIGS. 36A and 36B, in one preferred embodiment of the present invention for anterior insertion, expander 822 is located proximate the trailing end 826 of upper and lower members 802,806. Expander 822 moves arcuate portions 804, 808 of upper and lower members 802, 806 from a first angled orientation A, as shown in FIGS. 35 and 36A in a first position, to a second angled orientation A', as shown in FIG. 36B where implant 800 has a generally oblong cross section at trailing end 826, in a second position. The implant of the present invention need not be a true frusto-conical shape as a cross section need not form a complete circle but may have portions of the perimeter absent, less round, flattened including flattened on two or more sides, or other. It is appreciated that the expander also may move the arcuate portions of the upper and lower members from a first height at each end to a second and greater height at each end.

Figure 37:
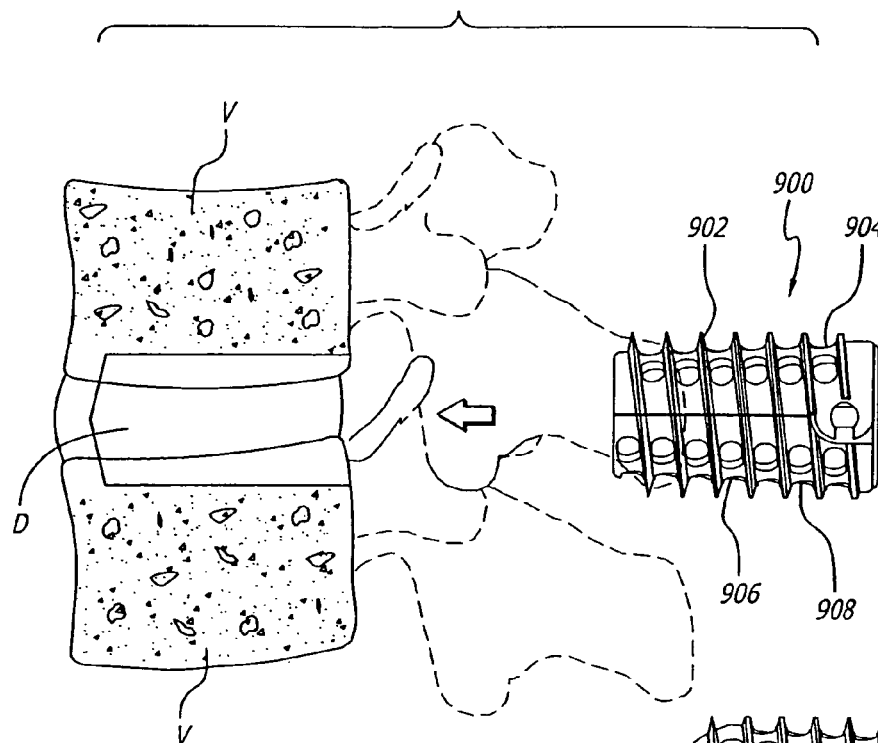
FIG. 37 is a cross-sectional side view of an implantation site formed posteriorly across the disc space between two adjacent vertebral bodies and another embodiment of an implant of the present invention for posterior insertion being installed into the implantation site.
Figure 38:
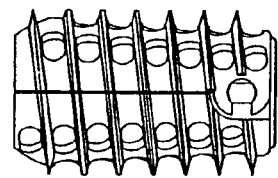
FIG. 38 is a side view of an alternative variation of the embodiment of the implant of FIG. 37 for posterior insertion.
Figure 39:
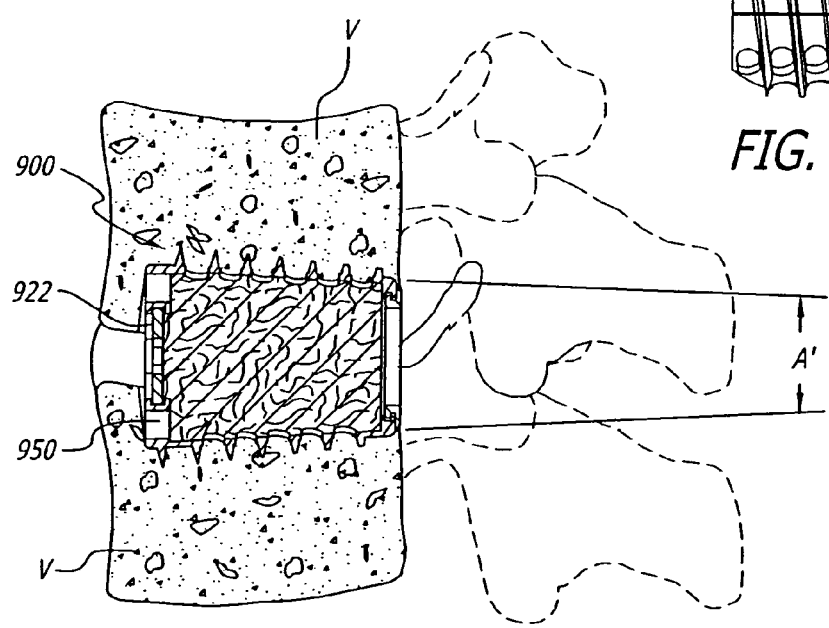
FIG. 39 is a cross-sectional side view of the implantation site formed across the space between two adjacent vertebral bodies and the implant of FIG. 37 installed into the implantation space.

Shown in FIGS. 37-39 is another embodiment of an implant of the present invention for posterior insertion with expander 922 located proximate the leading end 950. As shown in FIG. 37, implant 900 may be angled or tapered so as to converge from trailing end to leading end when in the collapsed position for insertion into the spine. The taper on implant 900 may facilitate its insertion. Alternatively, as shown in FIG. 38, the implant of the present invention may be angled or tapered so as to diverge from trailing end to leading end when in the collapsed position for insertion into the spine. For an implant with an angle that diverges for trailing end to leading end, the leading end may have a chamfer or other configuration to reduce the size of the leading end to facilitate insertion of the implant into the spine.

Figure 40:
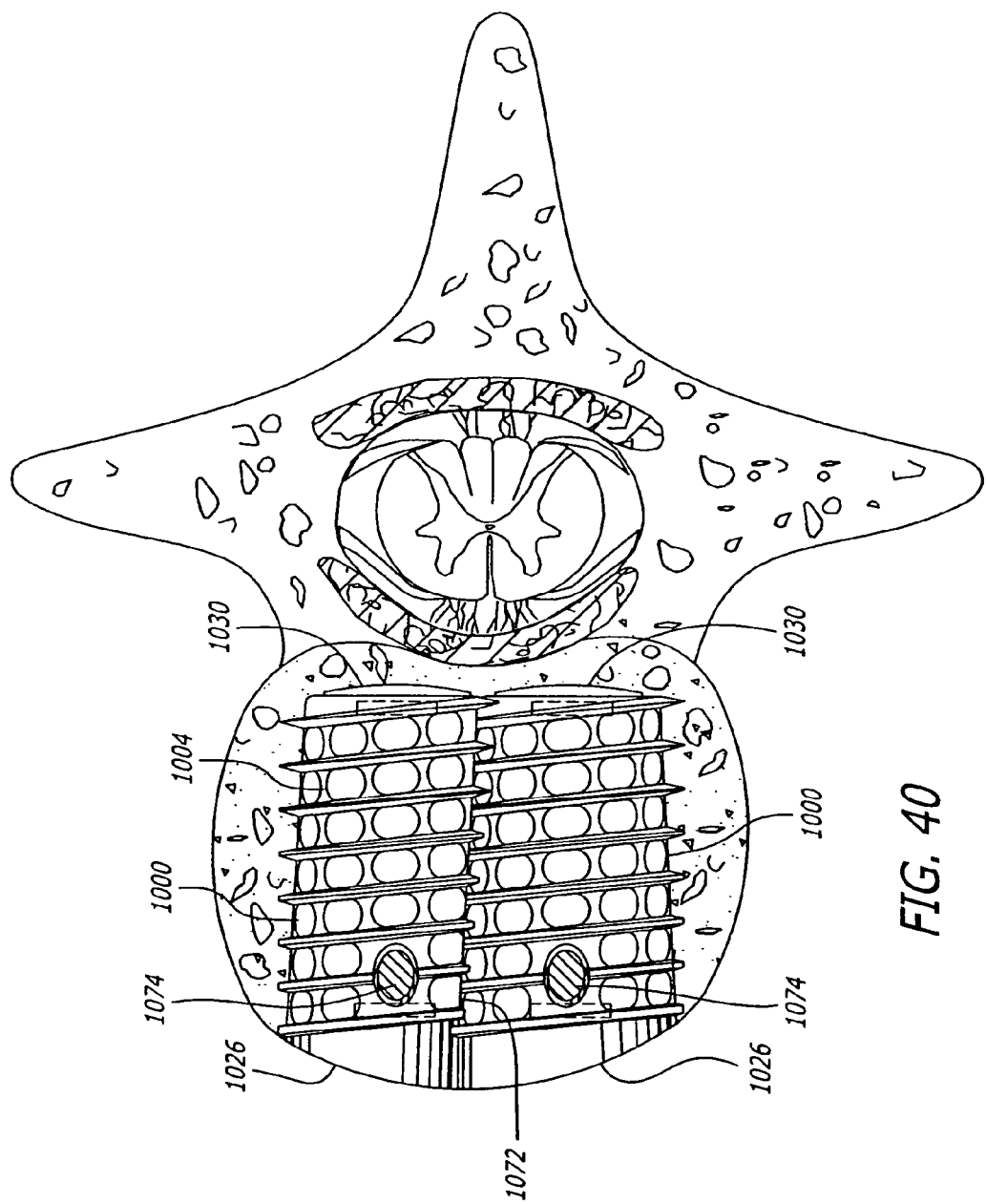
FIG. 40 is a top plan view of yet another embodiment of the implant of the present invention inserted upon the lower vertebral body of an implantation site formed anteriorly across a disc space with the vertebral body shown in partial cross-section.
Figure 41:
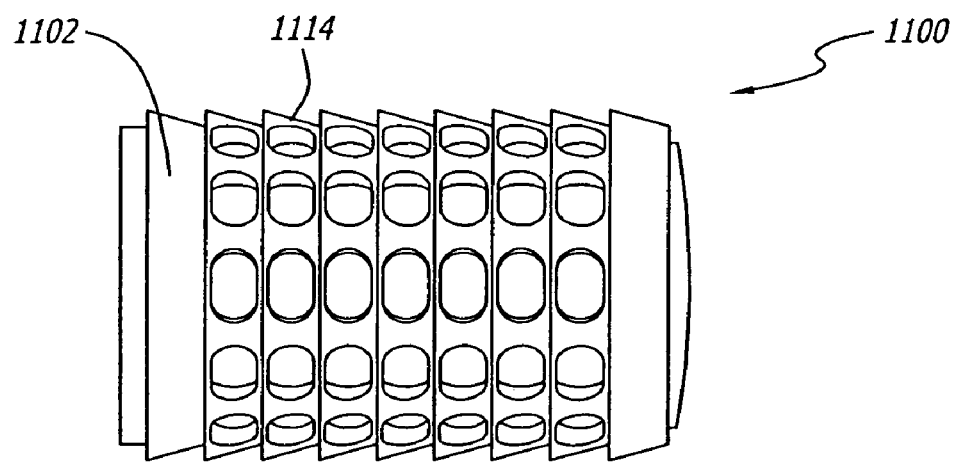
FIG. 41 is a top plan view of a spinal fusion implant of one embodiment of the present invention.
Figure 42:
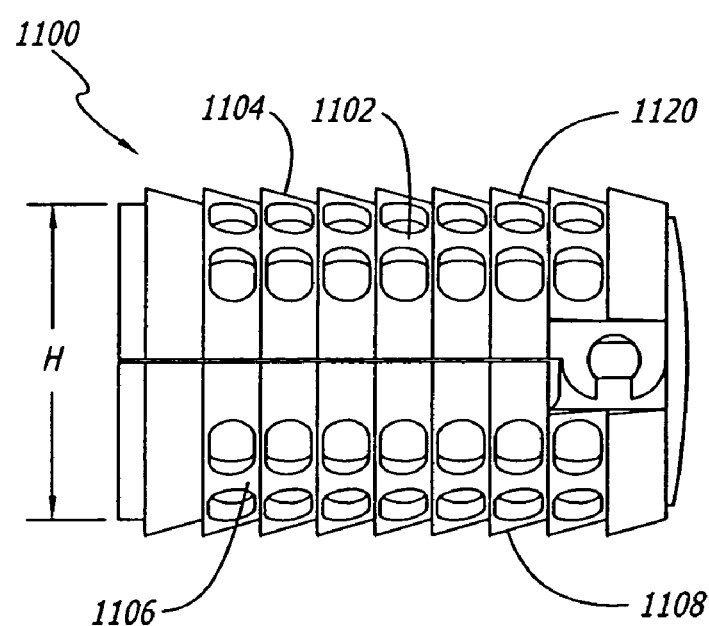
FIG. 42 is a side elevation view of the implant of FIG. 41.
Figure 48:
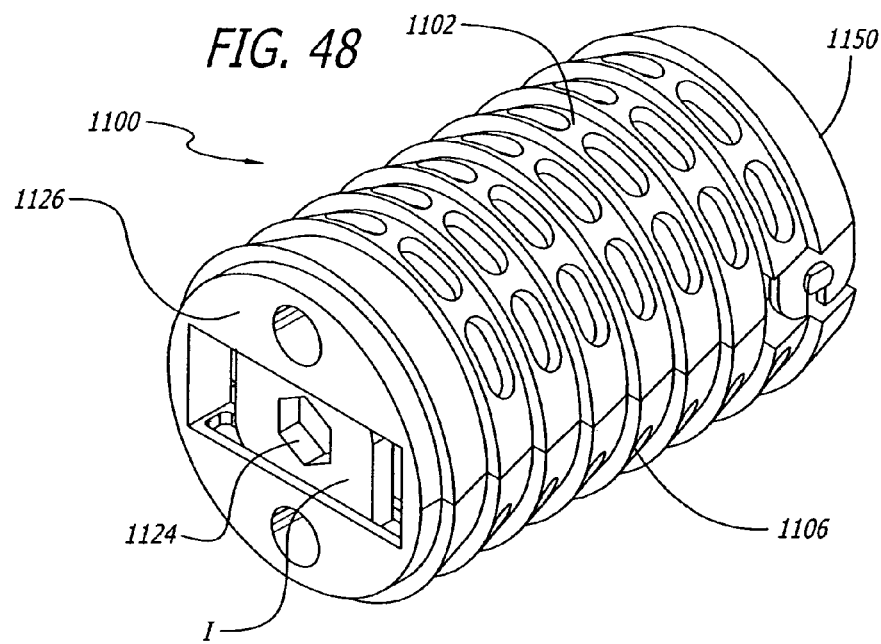
FIG. 48 is a trailing end perspective view of the implant of FIG. 41.
Figure 49:
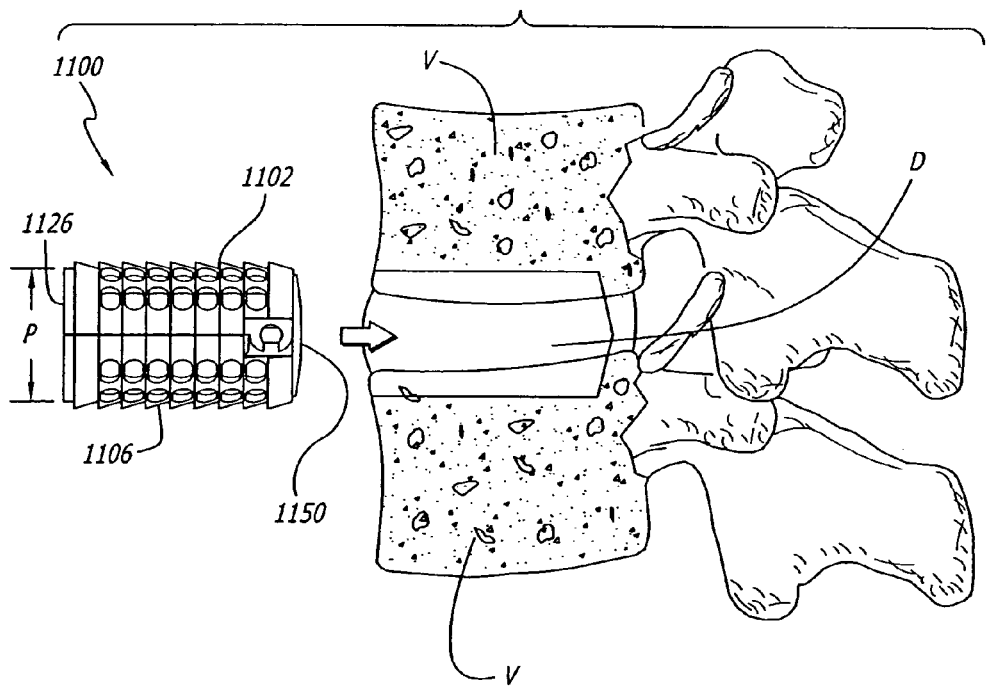
FIG. 49 is a side view of the implant of FIG. 48 being inserted from a generally anterior approach to the spine into an implantation site formed across a disc space and two adjacent vertebral bodies of the spine shown in partial cross-section.

Shown in FIG. 40, in accordance with the present invention, as embodied and broadly described herein, is yet another embodiment of an expandable threaded artificial interbody spinal fusion implant 1000 for insertion across a disc space D between two adjacent vertebral bodies V of a human spine. Threaded implant 1000 of the present invention includes an upper member 1002 having an arcuate portion 1004 for orientation toward the upper of adjacent vertebral bodies V and a lower member 1006 having an arcuate portion 1008 for orientation toward the lower of the adjacent vertebral bodies V. Implant 1000 further includes a side surface 1072 contoured to cooperatively receive another implant. Another aspect of implant 1000 is that its upper and lower members 1002, 1006 have screw holes 1074 passing therethrough adapted to receive a screw 1078 passing from the interior of implant 1000 into adjacent vertebral bodies V to anchor implant 1000 to an adjacent vertebral body V.

Figure 50A:
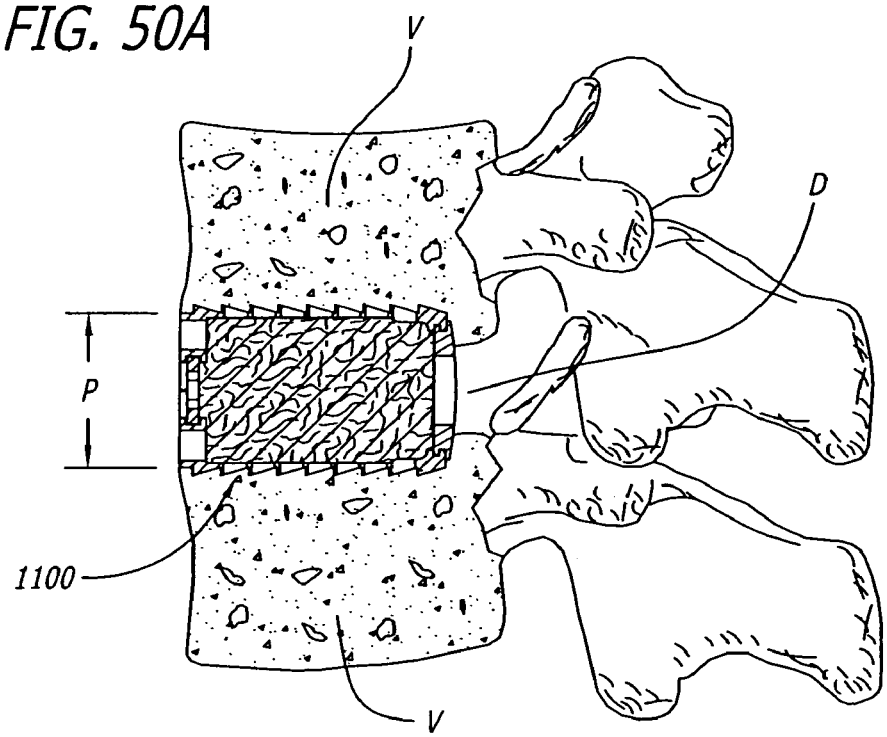
FIG. 50A is a cross-sectional view of the implant of FIG. 41 inserted in an implantation site formed across the disc space and two adjacent vertebral bodies of the spine.
Figure 50B:
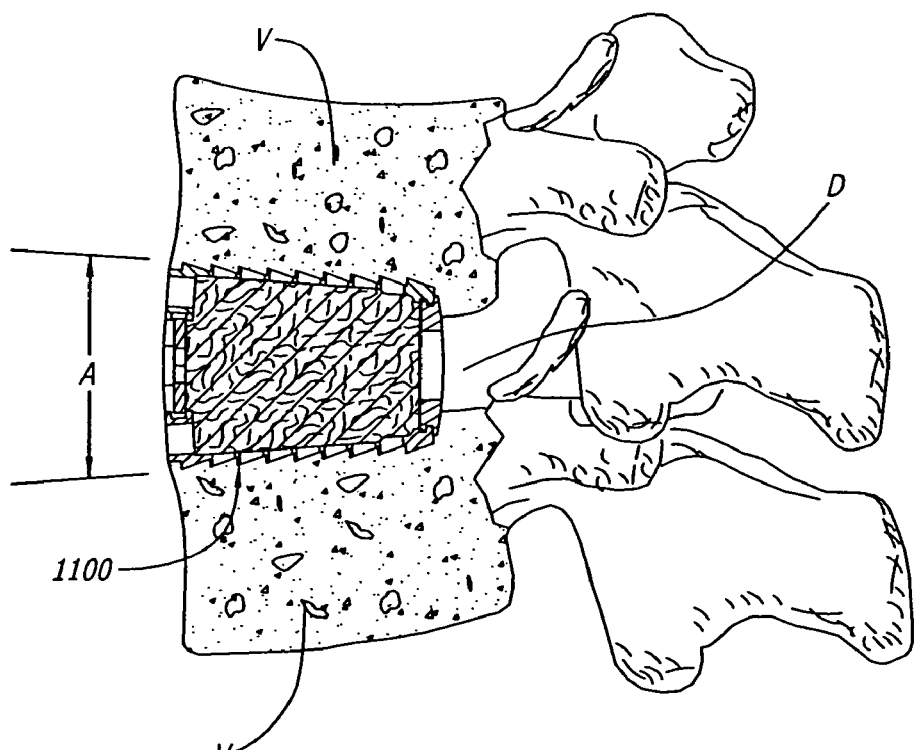
FIG. 50B is a cross-sectional view of the implant of FIG. 41 inserted in an implantation site of FIG. 50A and expanded to place the adjacent vertebral bodies in proper lordosis.

Shown in FIGS. 41-50B, in accordance with the present invention, as embodied and broadly described herein, is one embodiment of an expandable artificial interbody spinal fusion implant 1100 for anterior insertion across a disc space D between two adjacent vertebral bodies V of a human spine. Push-in implant 1100 of the present invention includes an upper member 1102 having an arcuate portion 1104 adapted for placement toward and at least in part within the upper of the adjacent vertebral bodies V and a lower member 1106 having an arcuate portion 1108 adapted for placement toward and at least in part within the lower of the adjacent vertebral bodies V. Arcuate portions 1104, 1108 of upper and lower members 1102, 1106 in the first position of the present invention are parallel to one another and form at least a portion of a cylinder along the length of implant 1100. On an exterior 1120 of each of opposed arcuate portions 1104, 1108 of upper and lower members 1102, 1106 is a portion 1114, 1116 of at least one bone-engaging projection 1118 adapted for linear insertion, which in one preferred embodiment is a ratchet. As shown in FIGS. 50A and 50B, expander 1122 is located proximate the trailing end 1126 of upper and lower members 1102, 1106.

Shown in FIGS. 43-47, in accordance with the present invention, as embodied and broadly described herein, is one embodiment of an expandable artificial interbody spinal fusion implant 1100' for anterior insertion across a disc space D between two adjacent vertebral bodies V of a human spine. Implant 1100' of FIGS. 43, 44, 46, and 47 has a similar configuration to that of implant 1100 of FIG. 41, except that it has portions of its perimeter flattened or truncated so as to have a truncated medial side 1117' and truncated lateral side 1119'. As best shown in FIGS. 44 and 47, medial side 1117' is truncated to a greater extent than lateral side 1119'. Alternatively, the medial side 1117' could be truncated to a lesser extent than lateral side 1119'. FIG. 45 shows an embodiment of the present invention with implant 1100'' having medial side 1117'' truncated to approximately the same extent as lateral side 1119'.

Implant 1100' has a major diameter or height equal to the distance between bone-engaging projects 1118' on opposed arcuate portions 1104', 1108'. The width of implant 1100' is equal to the distance between a flattened segment and a point diametrically opposite the flattened segment, such as the distance between the medial side 1117' and lateral side 1119'.

The effect of having at least one of medial side 1117' and lateral side 1119' truncated or reduced is that the width of implant 1100' is substantially reduced while the major diameter or height of implant 1100' is maintained.

Figure 51:
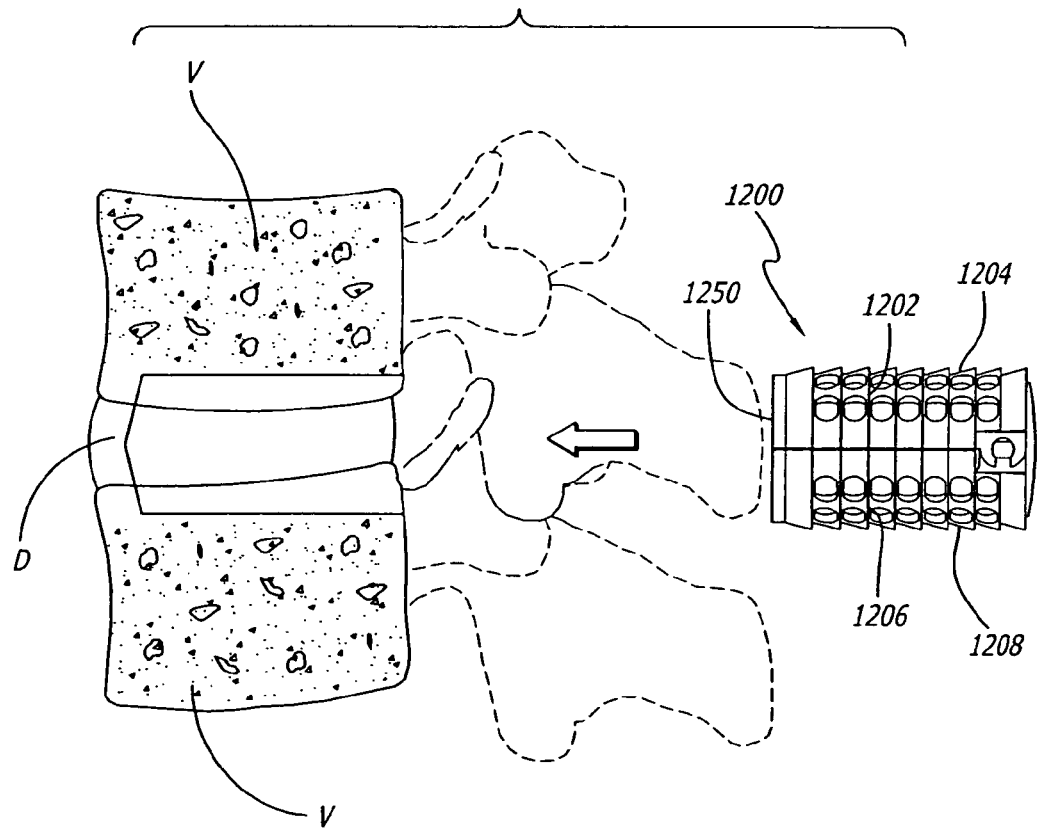
FIG. 51 is a cross-sectional side view of an implantation site formed posteriorly across the disc space between two adjacent vertebral bodies and a second embodiment of an implant of the present invention for posterior insertion being installed into the implantation site.

FIG. 51 shows another embodiment of the implant of the present invention for posterior insertion adapted for expansion proximate the leading end 1250. Implant 1200 is being implanted into the spine from the posterior aspect with expander 1222 on the leading end 1250 of implant 1200. While anterior and posterior aspect approaches have been illustrated herein, the present invention is not limited to these illustrated approaches. In particular, but not limited thereto, the push-in implant of the present invention also may be used in push-in implants for insertion from the translateral aspect of the spine as disclosed by Michelson in U.S. Pat. No. 5,860,973, which is incorporated herein by reference.

Figure 52:
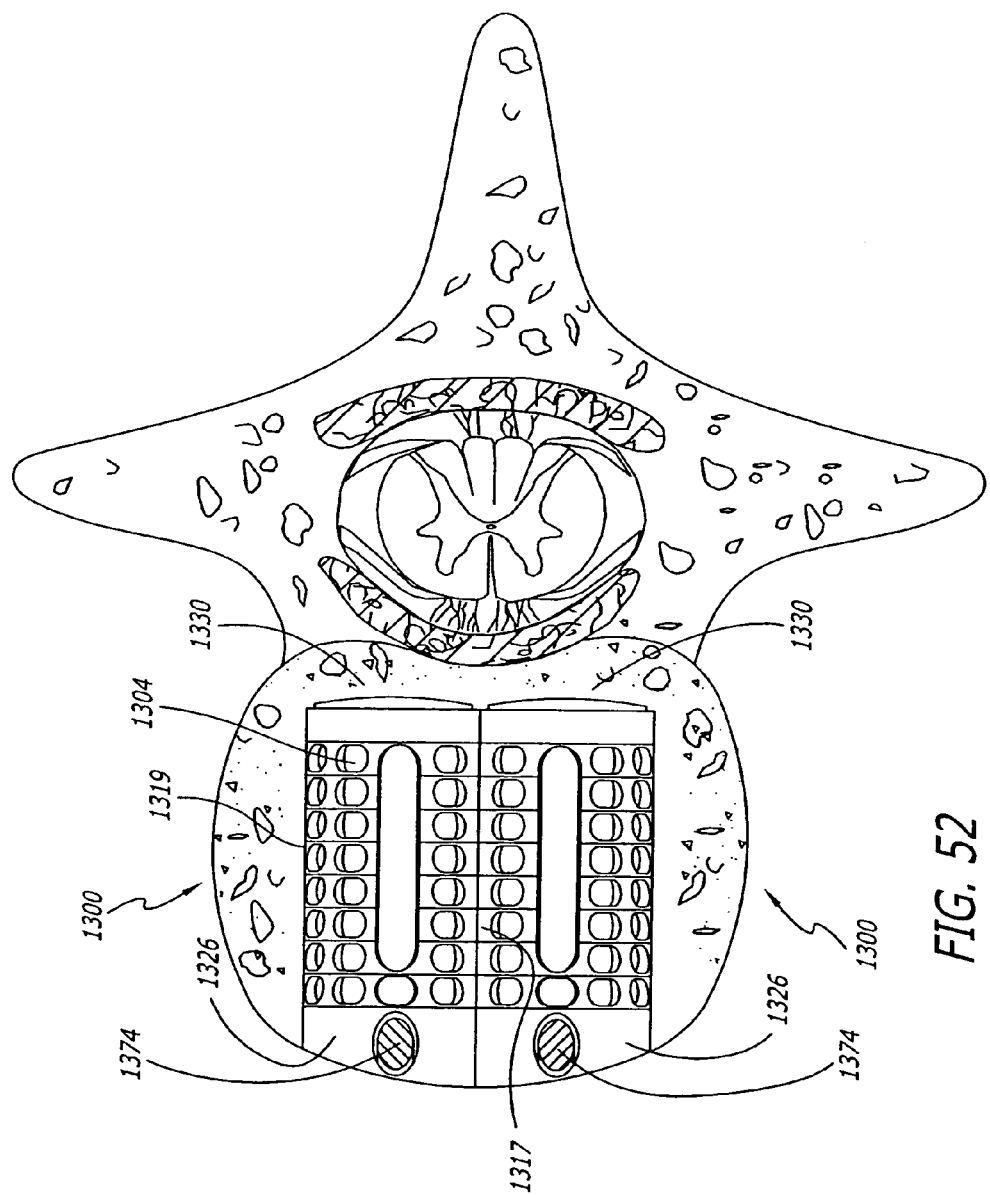
FIG. 52 is a top plan view of yet another embodiment of the present invention inserted upon the lower vertebral body of an implantation site formed anteriorly across a disc space with the vertebral body shown in partial cross-section.
Figure 53:
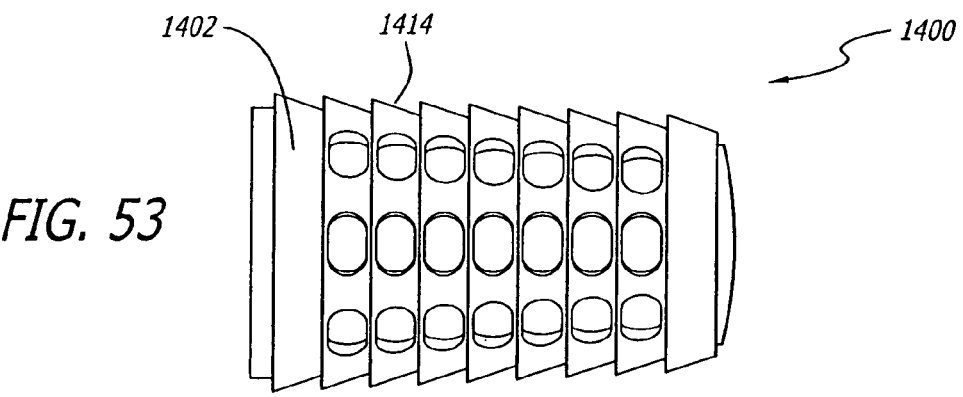
FIG. 53 is a top plan view of another spinal fusion implant of one embodiment of the present invention.
Figure 54:
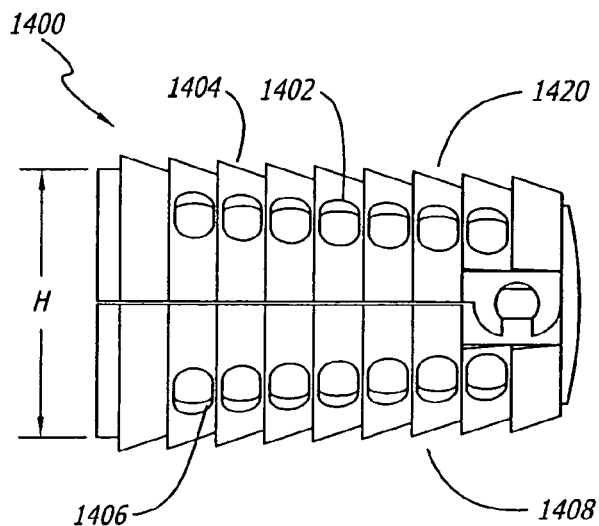
FIG. 54 is a side elevation view of the implant of FIG. 53.
Figure 55:
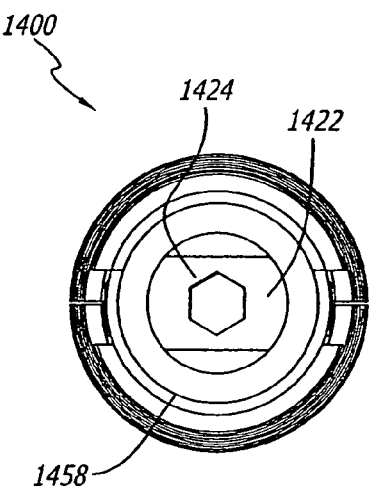
FIG. 55 is a leading end view of the implant with the end cap there attached of FIG. 53.
Figure 56:
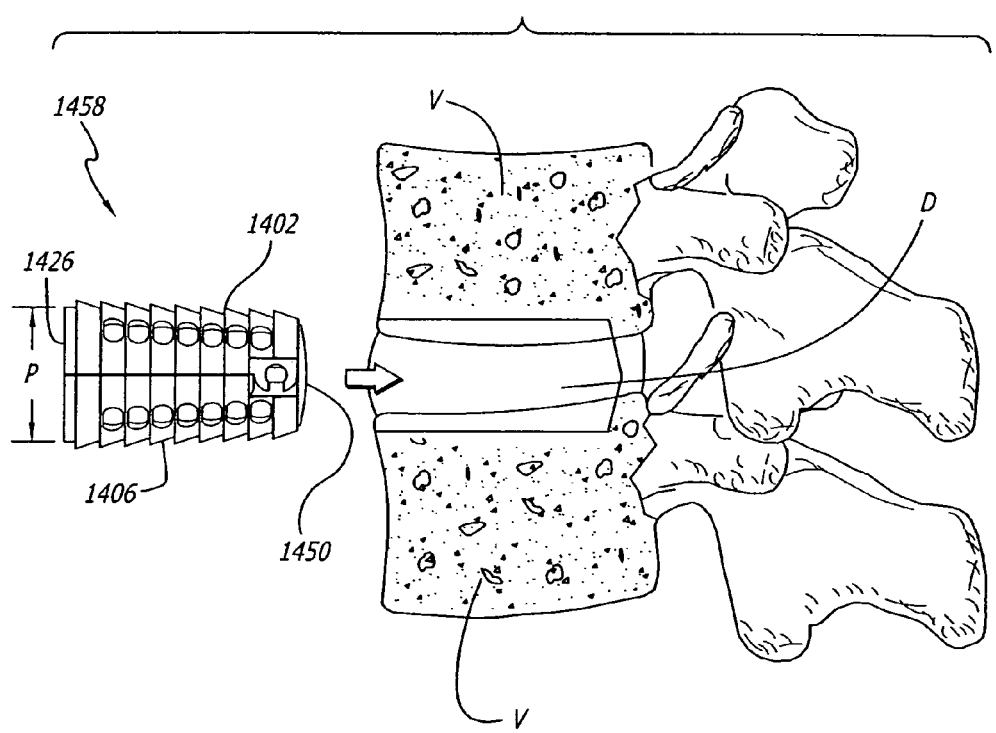
FIG. 56 is a side view of the implant of FIG. 53 being inserted from a generally anterior approach to the spine into an implantation site formed across a disc space and two adjacent vertebral bodies of the spine shown in partial cross-section.
Figure 57A:
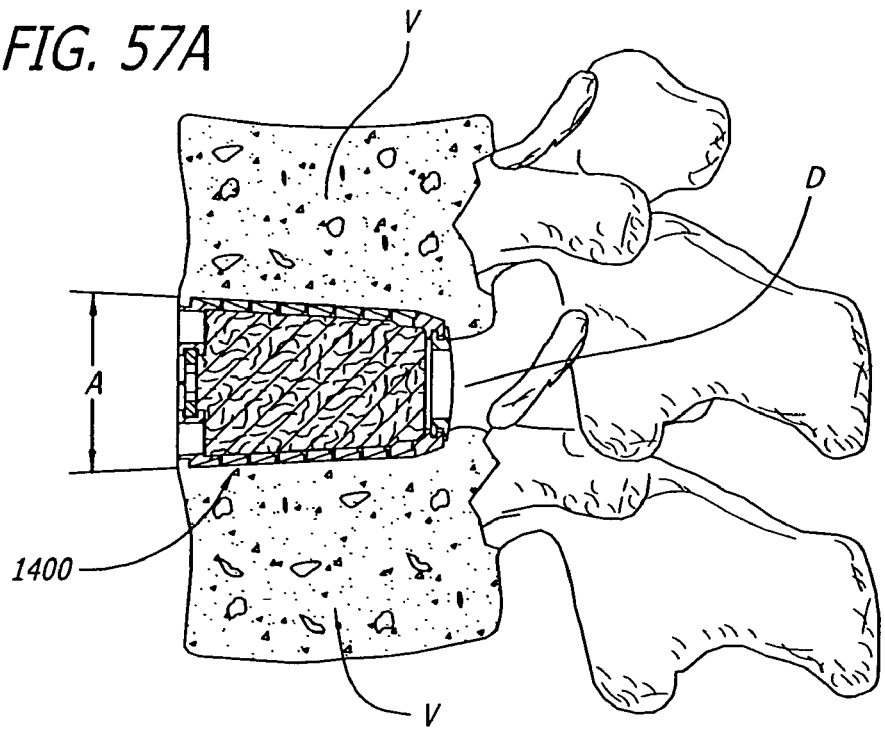
FIG. 57A is a cross-sectional view of the implant of FIG. 53 inserted in an implantation site formed across the disc space and two adjacent vertebral bodies of the spine.
Figure 57B:
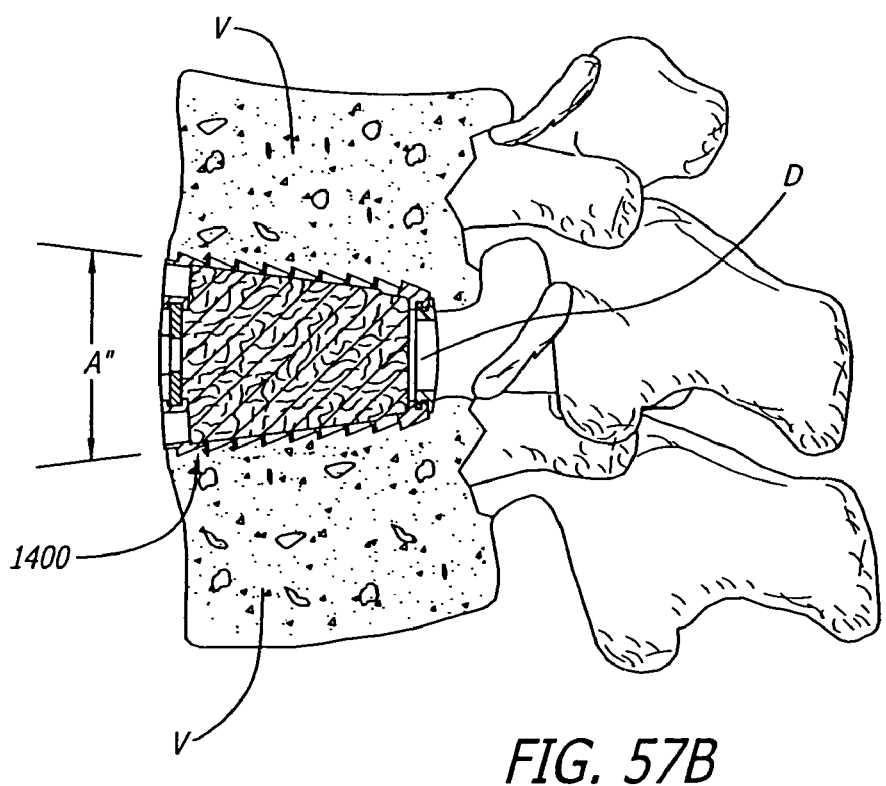
FIG. 57B is a cross-sectional view of the implant of FIG. 53 inserted in an implantation site of FIG. 57A and expanded to place the adjacent vertebral bodies in proper lordosis.

FIG. 52 shows a pair of side-by-side implants 1300 having a truncated medial side 1317 and a truncated lateral side 1319, respectively. The implants are implanted across the disc space with the medial sides facing and adjacent to another implant such that the combined overall width of the two spinal implants is less than twice the major diameter or height of the implants.

Shown in FIGS. 53-57B, in accordance with the present invention, as embodied and broadly described herein, is yet another embodiment of an expandable artificial interbody spinal fusion implant 1400 for anterior insertion across a disc space D between two adjacent vertebral bodies V of a human spine. Arcuate portions 1404, 1408 of upper and lower members 1402, 1406 in the first position of the present invention are angled to one another and form at least a portion of a frusto-conical shape along the length of implant 1400. While preferred embodiments of the present invention illustrated in the attached figures and discussed herein have arcuate portions 1404, 1408 angled to one another to form at least a portion of a frusto-conical shape along the length of implant 1400, the arcuate portions may also form at least a portion of a shape described as a cylinder split along a horizontal plane through its mid-longitudinal axis wedged upper half from lower half by an inclined plane or any variation thereof suitable for the intended purpose of the expandable implant having upper and lower arcuate portions of the present invention.

Shown in FIGS. 58-60 is another embodiment of an implant of the present invention for posterior insertion with expander 1522 located proximate the leading end 1550. As shown in FIG. 58, implant 1500 may be angled or tapered so as to converge from trailing end to leading end when in the collapsed position for insertion into the spine. The taper on implant 1500 may facilitate its insertion. Alternatively, as shown in FIG. 59, the implant of the present invention may be angled or tapered so as to diverge from trailing end to leading end when in the collapsed position for insertion into the spine. For an implant with an angle that diverges for trailing end to leading end, the leading end may have a chamfer or other configuration to reduce the size of the leading end to facilitate insertion of the implant into the spine.

Figure 61:
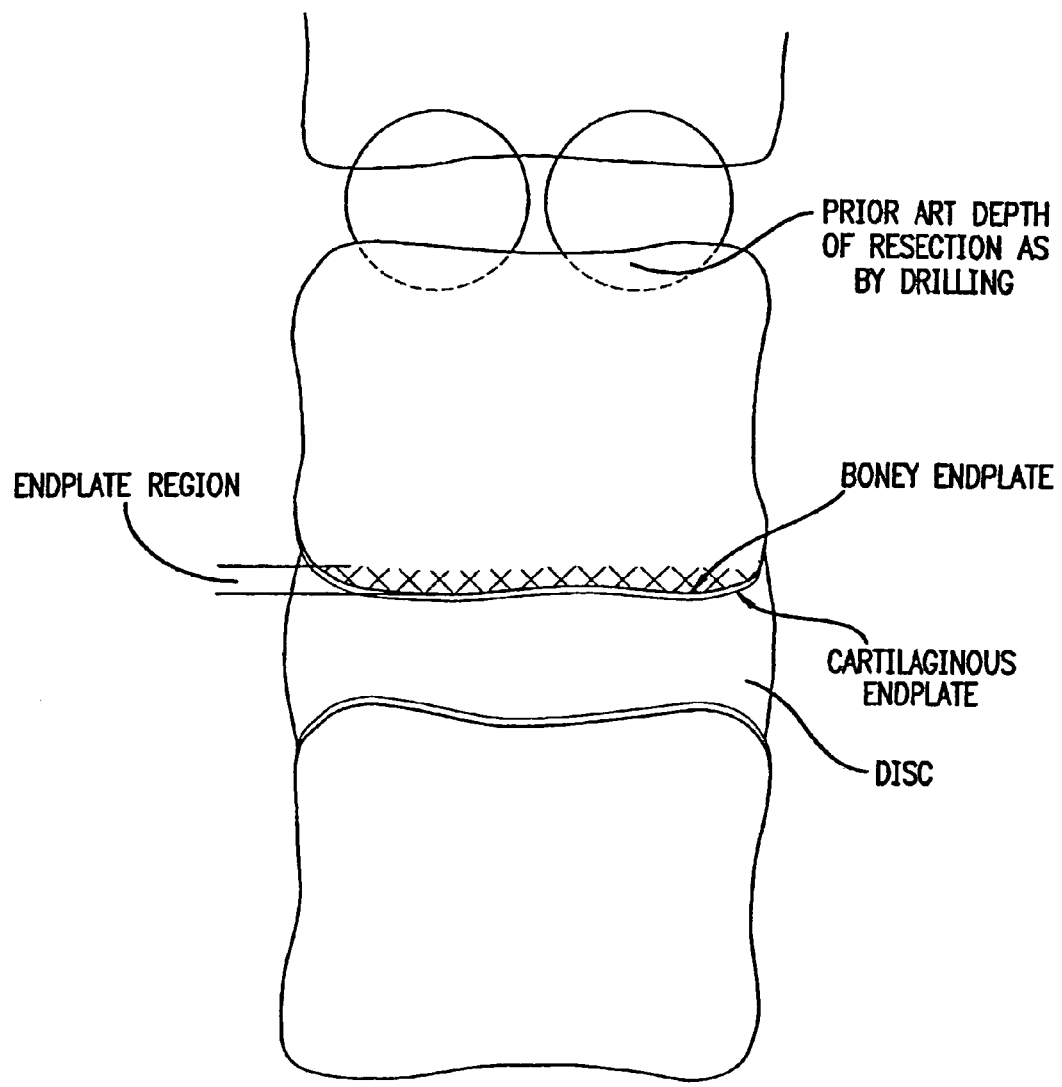
FIG. 61 is a front elevation view of two disc levels of the lumbar spine showing the prior art depth of resection resulting from drilling through the bony endplate region of adjacent vertebral bodies and showing the endplate region on a vertebral body.

Human vertebral bodies have a hard outer shell of compacted dense cancellous bone (sometimes referred to as the cortex) and a relatively softer, inner mass of cancellous bone. Just below the cortex adjacent the disc is a region of bone referred to herein as the "subchondral zone". As best shown in FIG. 61, the outer shell of compact bone (the bony endplate) adjacent to the spinal disc and cartilaginous endplate and the underlying subchondral zone are together herein referred to as the bony "end plate region" and, for the purposes of this application, is hereby so defined. In the lumber spine the bony endplate is generally 2 mm deep. By way of example, prior art threaded implants requiring approximately a 3 mm drill depth into the vertebral body will have threads of approximately 1 mm or more resulting in a total depth of penetration into the vertebral body of 4 mm or more. The embodiment of the implant of the present invention to be described next permits the implant to penetrate into the vertebral bodies to a depth of less than 3 mm or not to penetrate into the vertebral bodies.

Shown in FIGS. 62-67, in accordance with the present invention, as embodied and broadly described herein, is one embodiment of an expandable push-in artificial interbody spinal fusion implant 1600 for posterior insertion across a disc space D between two adjacent vertebral bodies V of a human spine. Push-in implant 1600 of the present invention includes an upper member 1602 having an upper surface 1604 adapted for placement toward and into contact with the upper of the adjacent vertebral bodies V and a lower member 1606 having a lower surface 1608 adapted for placement toward and into contact with the lower of the adjacent vertebral bodies V. Upper and lower surfaces 1604, 1608 of upper and lower members 1602, 1606 have at least one opening 1610, 1612 in communication with one another for permitting for the growth of bone from vertebral body V to adjacent vertebral body V through implant 1600. Upper and lower members 1602, 1606 are articulated therebetween at an adjacent one of the proximal ends and the distal ends of upper and lower members 1602, 1606 and allow for rotation between the articulating members at the end opposite the articulating end of implant 1600. Upper and lower members 1602, 1606 have a first position relative to one another that allows for a collapsed implant height and a second position relative to one another that allows for an increased height. Upper and lower surfaces 1604, 1608 of upper and lower members 1602, 1606 in the first position of the present invention are parallel to one another. On an exterior 1620 of each of opposed upper and lower surfaces 1604, 1608 of upper and lower members 1602, 1606 is at least one bone-engaging projection 1618 adapted for linear insertion, which in one preferred embodiment is a ratchet. Alternatively, bone-engaging projection 1618 can be a surface roughening, knurling, or any other configuration suitable for the intended purpose.

While a specialized form of a blocker 1621 is described in significant detail herein with reference to expander 1622, blocker 1621 need not be in contact with upper and lower members 1602, 1606 when implant 1600 is initially inserted into the implantation space. As will be described with reference to FIGS. 93-98, certain embodiments of the present invention do not require a blocker at all but utilize a cooperatively engaging interlocking wall configuration. Blocker 1621 may be a block or any type of spacer that is inserted between the articulated upper and lower members 1602, 1606 after implant 1600 is positioned so as to hold portions of the upper and lower members 1602, 1606 spaced apart the optimal height and angulation relative to one another. The present invention includes expanding the implant with a tool, such as a spreader or a distractor but is not limited to a scissors type, a rack and gear type, a threaded member type or any other specific type of movement mechanism. Each tool nevertheless preferably engages upper and lower implant members 1602, 1606 to urge them apart. Blocker 1621 is then inserted into contact with upper and lower members 1602, 1606 to maintain implant 1600 at an expanded height.

As used herein with reference to embodiments directed to impacted or block implants the terms "generally or substantially planar" and "non-arcuate" are intended to describe the upper and lower surfaces of the implant of the present invention as having (1) no curvature, as in a planar surface, (2) slight or mild curvature from the leading end to the trailing end of the implant, and/or (3) slight or mild curvature across the implant width. Slight or mild curvature does not include the curvature associated with the upper and lower surfaces of implants for insertion into a disc space having a circular cross section formed across a spinal disc and into the adjacent vertebral bodies. While the upper and lower surfaces of the present invention may have some curvature, in comparison to an implant having a circular cross section, the curvature is minimal. For implants having a circular cross section such as threaded implants the curvature of the upper and lower surfaces contacting the adjacent vertebral bodies is a radius of half the width of the implant. If there is a curvature to the upper and lower surfaces of the present invention, the curvature is that of a circle much greater than the width of the implant; thus, it has a slight curvature that may correspond to an anatomical curvature of a disc or the surface of the vertebral endplate.

In another embodiment, the upper and lower surfaces may have a relatively mild convexity in at least one or both directions so as to better conform to the anatomical shape of the disc space or the vertebral endplates. While a substantially parallelepiped shape having a quadrilateral cross section may be generally preferred the leading and trailing ends may be substantially rounded to some advantage.

The height of the implant is at least that of the height of the restored disc space into which it is inserted. The implant is inserted at least in part within the space that was previously occupied by the disc material that was contained between the vertebral bodies.

Figure 62:
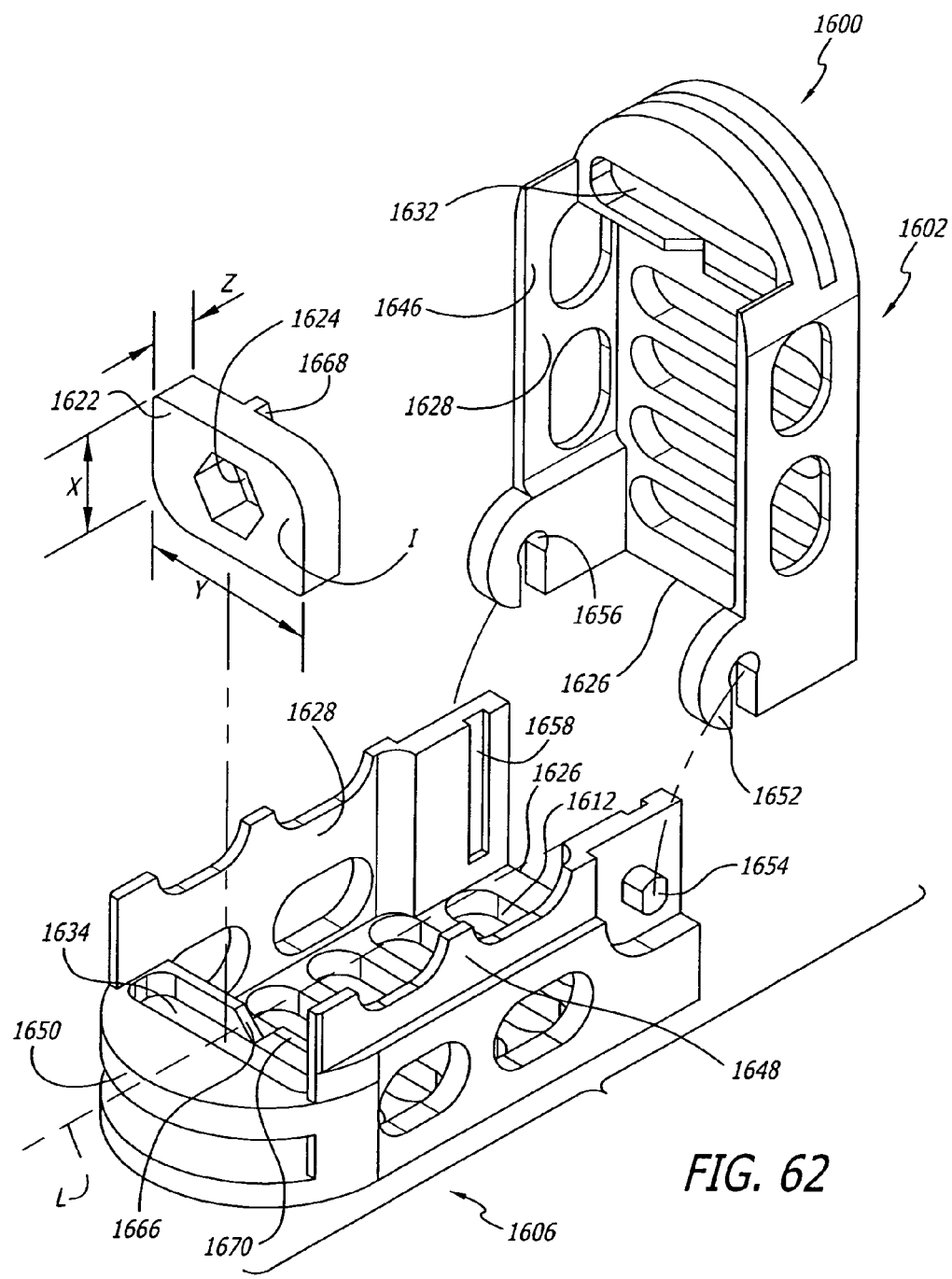
FIG. 62 is an exploded perspective view of a spinal fusion implant of one embodiment of the present invention.
Figure 63:
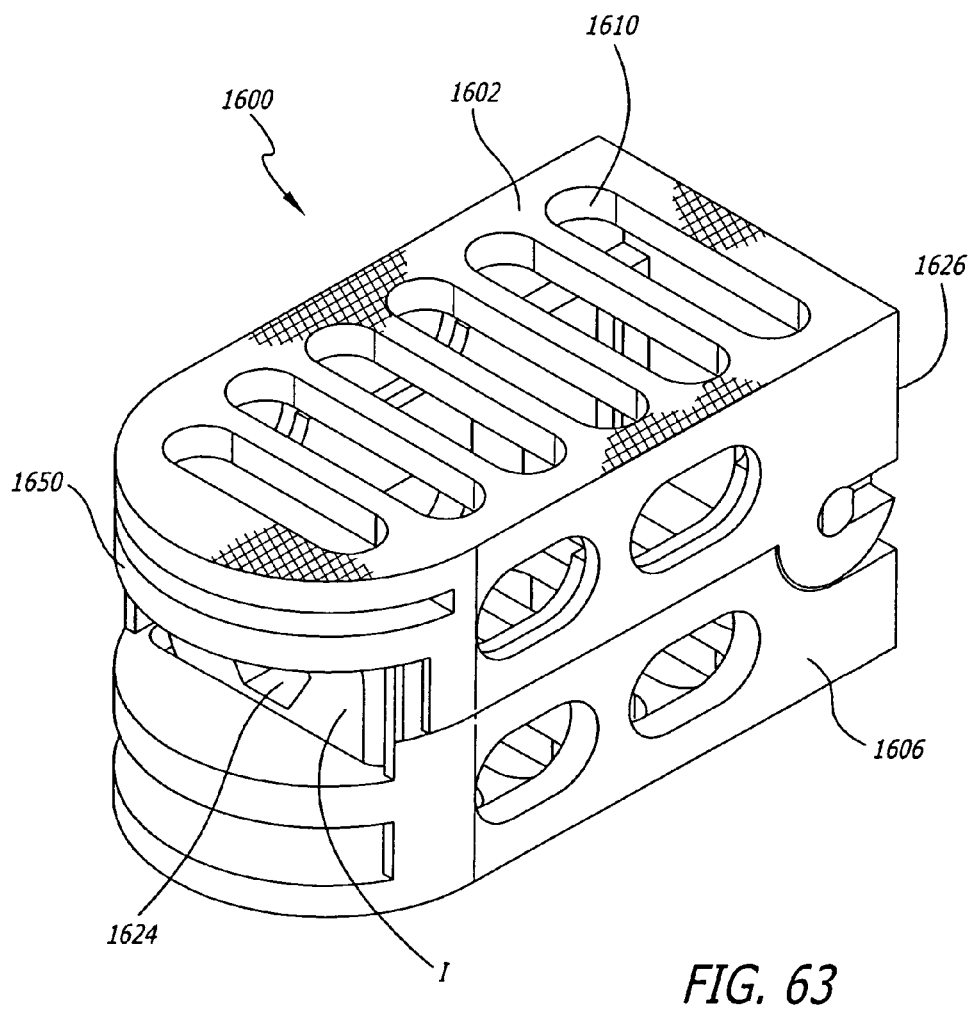
FIG. 63 is a leading end perspective view of the implant of FIG. 62.
Figure 64:
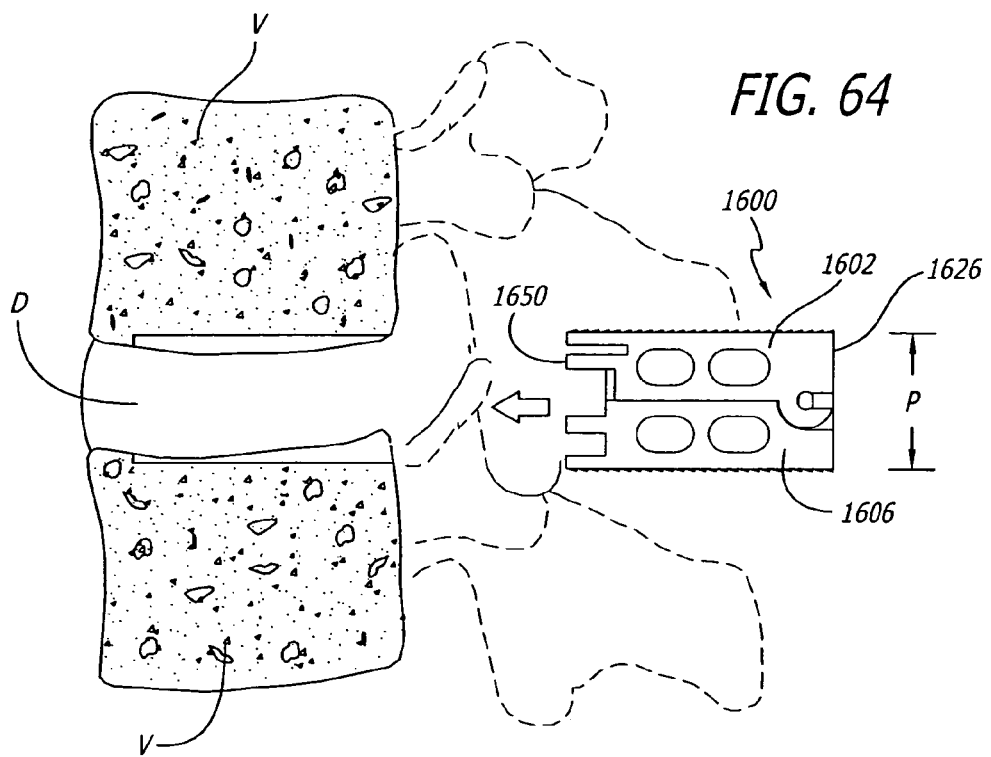
FIG. 64 is a side view of the implant of FIG. 62 being inserted from a generally posterior approach to the spine into an implantation site formed across a disc space and two adjacent vertebral bodies of the spine shown in partial cross-section.
Figure 65:
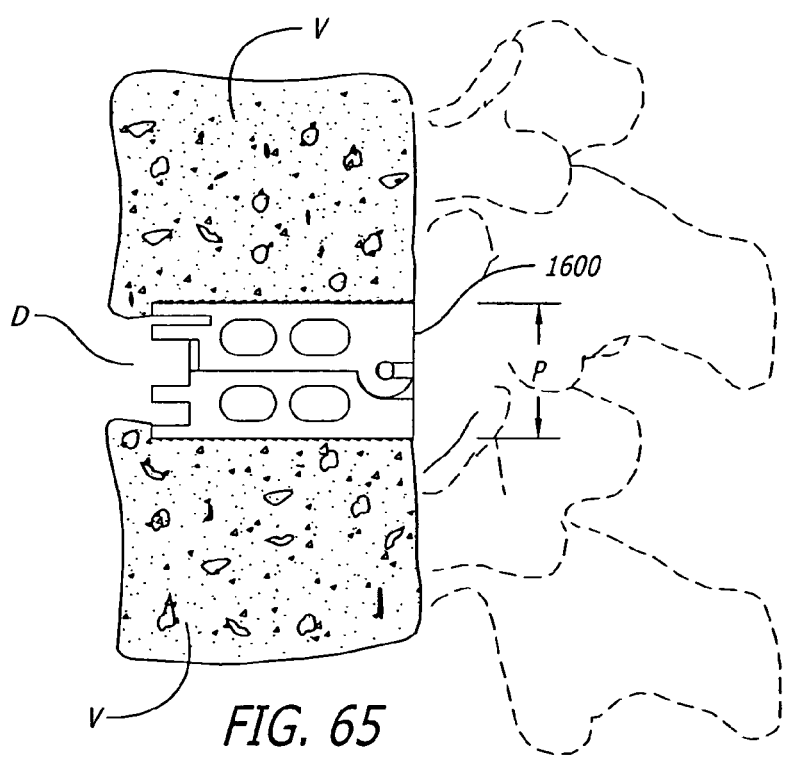
FIG. 65 is a side view of the implant of FIG. 64 inserted in an implantation site formed across the disc space and two adjacent vertebral bodies of the spine.
Figure 66:
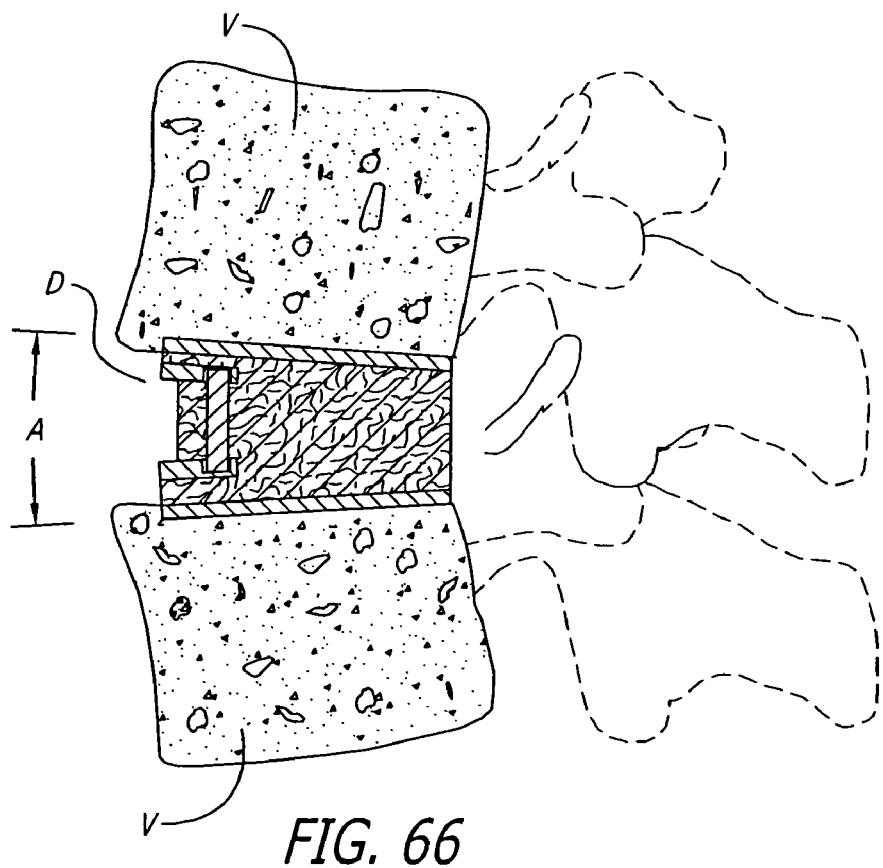
FIG. 66 is a cross-sectional side view of the implant of FIG. 64 with the implant in an expanded position inserted in an implantation site formed across the disc space and two adjacent vertebral bodies of the spine.
Figure 67:
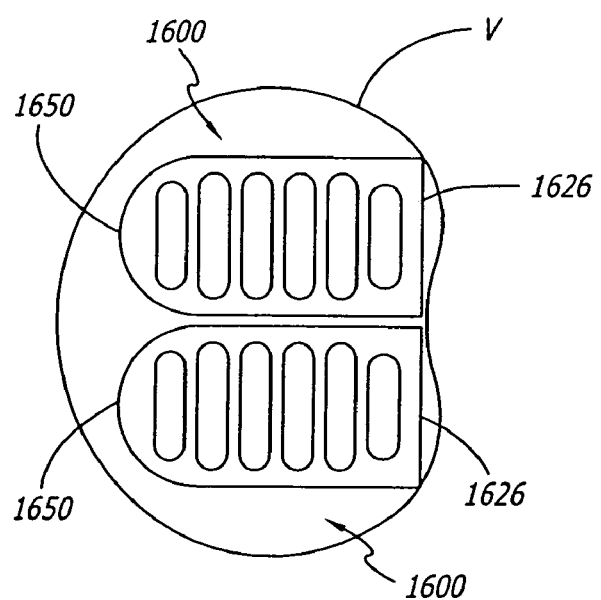
FIG. 67 is a top view of two implants of FIG. 62 implanted in a final position upon the lower vertebral body of an implantation site formed posteriorly across a disc space.
Figure 68:
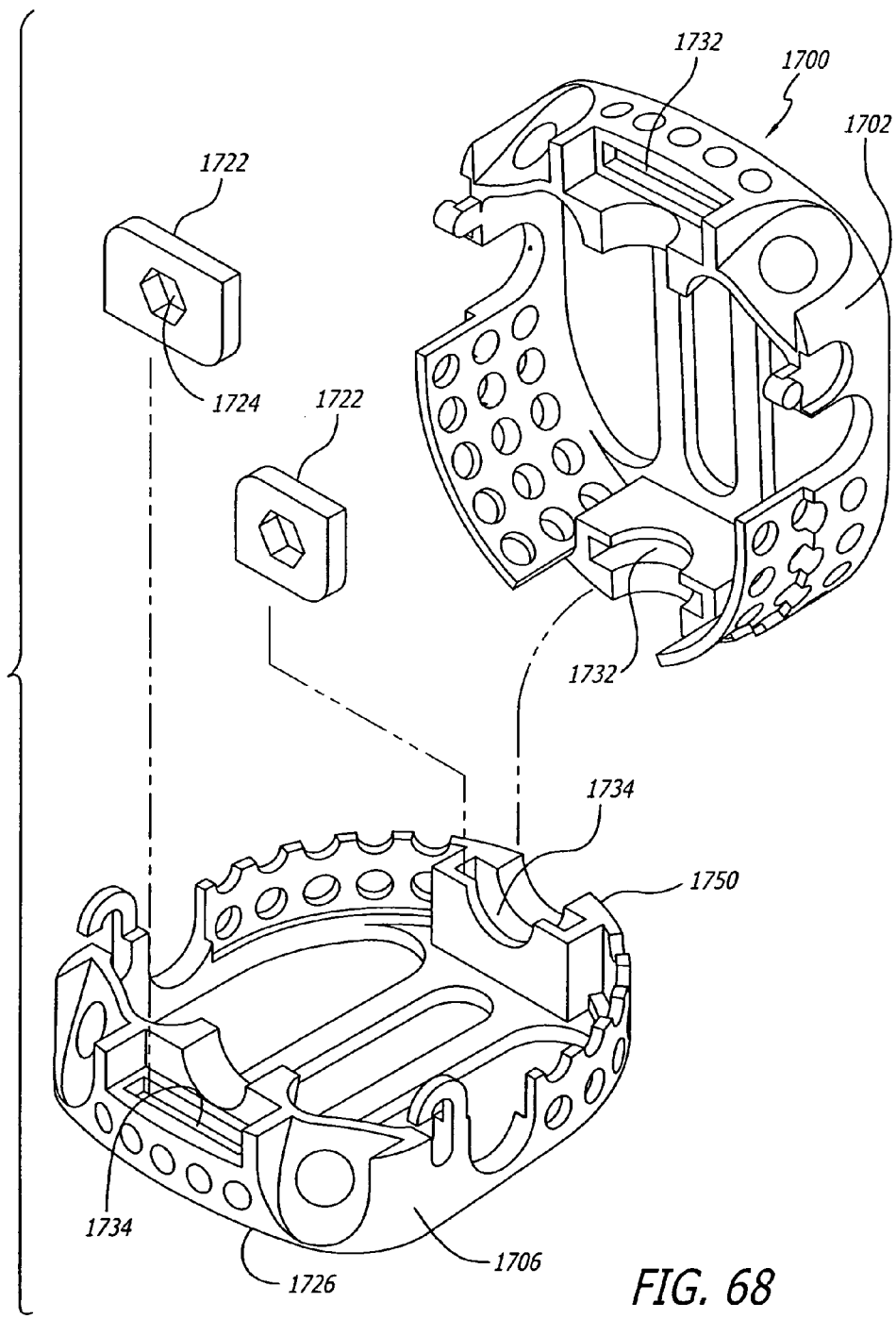
FIG. 68 is an exploded perspective view of a spinal fusion implant of another embodiment of the present invention.
Figure 70:
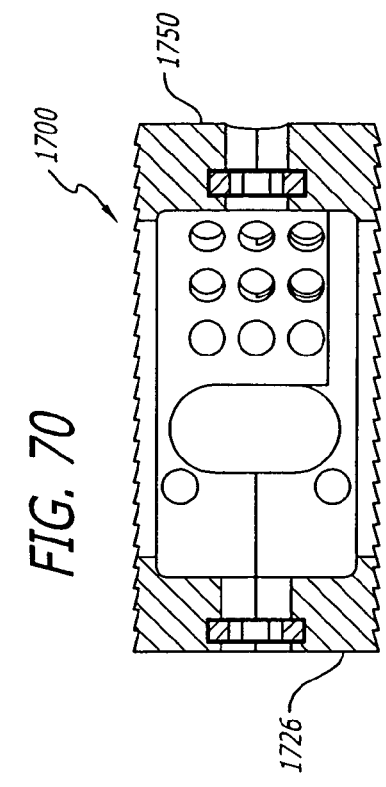
FIG. 70 is a cross-sectional side view along the mid-longitudinal axis of the implant of FIG. 68.
Figure 71B:
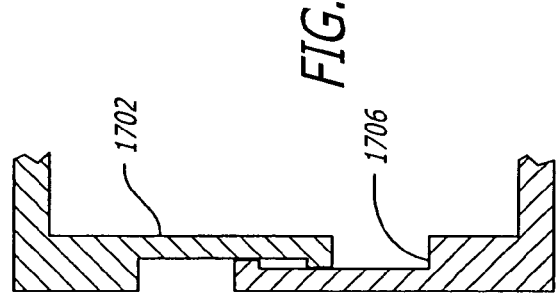
FIG. 71B is a partial cross sectional view of an embodiment of the interlocking wall design of FIG. 71A shown in a partially expanded position for implants of the present invention.
Figure 69:
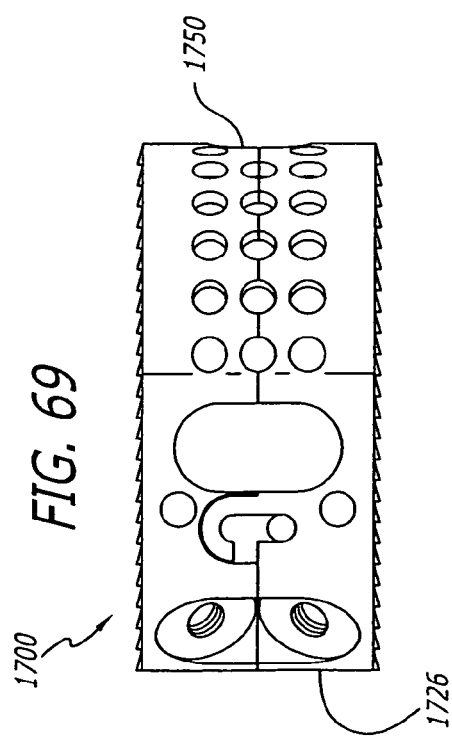
FIG. 69 is a side view of the implant of FIG. 68.
Figure 71A:
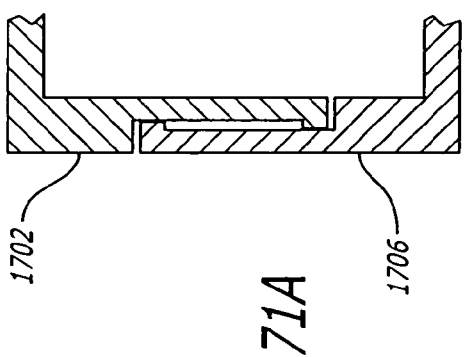
FIG. 71A is a partial cross sectional view of an embodiment of an interlocking wall design shown in the collapsed state for implants of the present invention.

As shown in FIGS. 62 and 63, in one preferred embodiment of the present invention for posterior insertion, expander 1622 is located proximate the leading end 1650 of upper and lower members 1602, 1606. In another embodiment shown in FIGS. 68-75 for anterior insertion, expanders 1722 used in implant 1700 are located proximate each of the trailing end 1726 and leading end 1750. An alternative embodiment of the present invention for anterior insertion shown in FIGS. 76-78 has an expander 1822 located proximate trailing end 1826 only of implant 1800. Implant 1600 preferably has an interior surface 1628 and a hollow 1630 defined therein. Expander 1622 of the present embodiment is located proximate interior surface 1628 and more particularly proximate interior surface 1628 at leading end 1650 of upper and lower members 1602, 1606. As is preferred, hollow 1630 between the ends is unobstructed by expander 1622 so as to allow for the unimpeded loading of the interior of the implant with the desired fusion-promoting substances; thus, loading the implant is easy. Further, this preferred configuration of implant 1600 makes available all of the volume of the hollow to contain fusion-promoting substances and so as to permit for the growth of bone directly through the hollow unobstructed by the expander to adjacent vertebral bodies V. Unobstructed hollow 1630 further allows for packing implant 1600 with fusion-promoting substances. It is appreciated that depending on the intended results, the expander also may be located at distal end 1626 or leading end 1650 of upper and lower members 1602, 1606 or anywhere else within the implant. The unobstructed hollow preferably has no mechanism extending along the longitudinal axis of the implant when finally deployed and the mechanism that moves the implant from a first position to a second position preferably does not move expander 1622 longitudinally through the hollow portion. The expander may work by pivoting on a surface in contact with an interior wall portion of at least one of the upper and lower members 1602, 1606. Moreover, multiple expanders may be used in contact with upper and lower members 1602, 1606 at any location within implant 1600.

An alternative embodiment of an expander used with the present invention includes an expander having an external thread that cooperates with converging threaded portions of the upper and lower members 1602, 1606 to expand the implant as the expander is rotated into position. Another alternative embodiment of an expander includes an expander having a cam configuration to expand the implant upon rotation.

Similar implants may be used in the reverse direction, from anterior to posterior by moving the pivot to the leading end and having the expander at the trailing end. Thus, the implant will get taller at its trailing end instead of its leading end. This smaller width implant design can be used to do an anterior approach spinal fusion where the surgeon wants to put in two implants instead of one large implant as when the surgery is to be preformed laproscopically.

A cap having an exterior surface and an interior surface may be used to close trailing end 1626 of implant 1600. The interior surface of the cap may have spaced slots about its circumference to facilitate a snap fit between the cap and the implant 1600. The cap and implant 1600 can of course be adapted for either or both ends of implant 1600. Further, the cap may be solid or perforate and made of a surgical quality plastic that may be resorbable or of any other suitable material.

For a posterior approach implant, it may be desirable to have a cap on the trailing end. The trailing end of the implant in a posterior approach implant has direct exposure to the spinal canal where the spinal cord and nerve roots are located. A cap on a posterior approach implant may be for the purpose of sealing off the spinal canal from the fusion-promoting substances contained in the hollow interior of the implant so that no bone grows into the canal. Further, the present invention implant may be used in combination with chemical substances and/or compounds applied at the trailing end of the implant to inhibit scar formation, and the cap may be of benefit in shielding the fusion-promoting substances contained in the implant from these scar formation inhibiting chemicals and compounds. It may also be for the purposes identified herein used in association with the leading end cap of an anterior approach implant. An anterior approach implant may have a leading end, trailing end, or both ends that are adapted to engage a cap. One of the purposes for that cap includes restricting the passage of fusion-promoting substances so that they remain loaded within the implant. Another purpose of the cap may be to add structural support to the implant. The cap may be solid or it may have openings therethrough. Any such openings could allow for the loaded material to stay within the implant while providing for vascular access to allow for the ingrowth of blood vessels and the growth of bone through the end of the implant.

Shown in FIGS. 68-75, in accordance with the present invention, as embodied and broadly described herein, is an embodiment of an expandable push-in artificial interbody spinal fusion implant 1700 for anterior insertion across a disc space D between two adjacent vertebral bodies V of a human spine. Push-in implant 1700 of the present invention includes an upper member 1702 having an upper surface 1704 adapted for placement toward and in contact with the upper of the adjacent vertebral bodies V and a lower member 1706 having a lower surface 1708 adapted for placement toward and in contact with the lower of the adjacent vertebral bodies V. Implant 1700 in FIGS. 72 through 75 is shown being implanted into the spine from the anterior aspect with expanders 1722 on the distal end 1726 and leading end 1750 of implant 1700. While anterior and posterior aspect approaches have been illustrated herein, the present invention is not limited to these illustrated approaches. In particular, but not limited thereto, the push-in implant of the present invention also may be used in push-in implants for insertion from the translateral aspect of the spine as disclosed by Michelson in U.S. Pat. No. 5,860,973, which is incorporated herein by reference.

Figure 72:
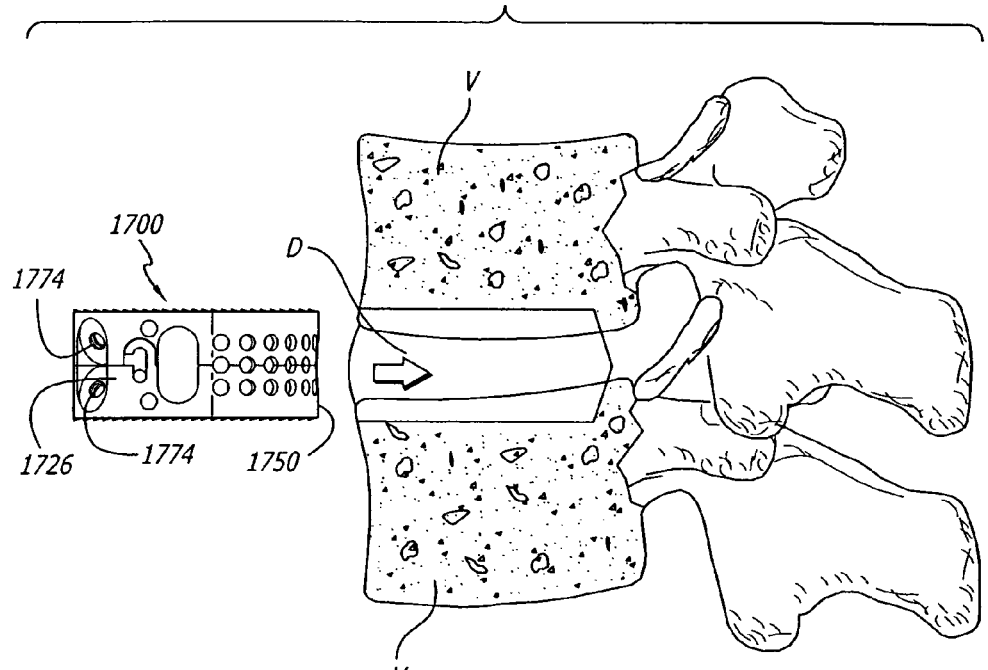
FIG. 72 is a cross-sectional side view of an implantation site formed anteriorly across the disc space between two adjacent vertebral bodies and the implant of FIG. 68 being installed into the implantation site.
Figure 72A:
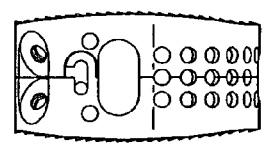
FIG. 72A is a side view of an alternative implant having an anatomically shaped upper and lower surface for insertion from the anterior aspect of the spine.
Figure 73:
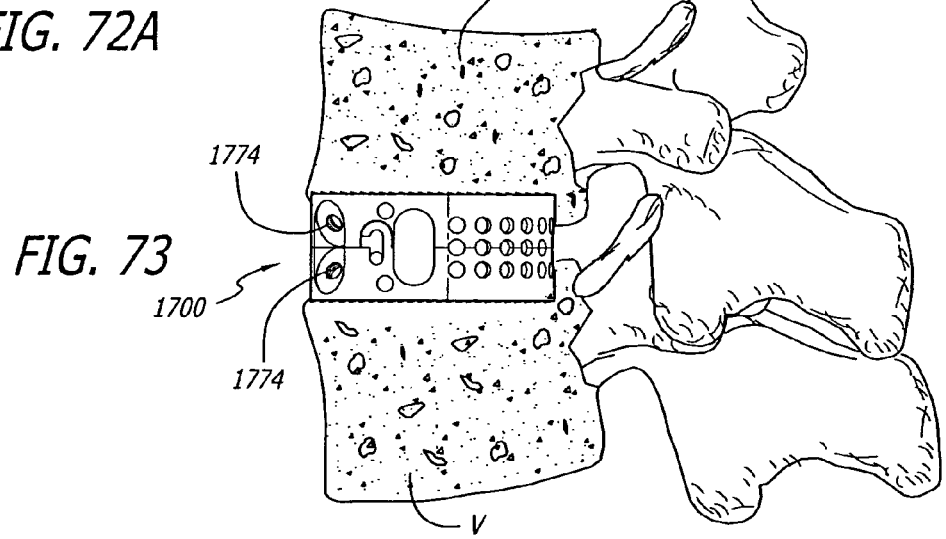
FIG. 73 is a cross-sectional side view of the implantation site formed across the space between two adjacent vertebral bodies and the implant of FIG. 68 installed into the implantation site.
Figure 74:
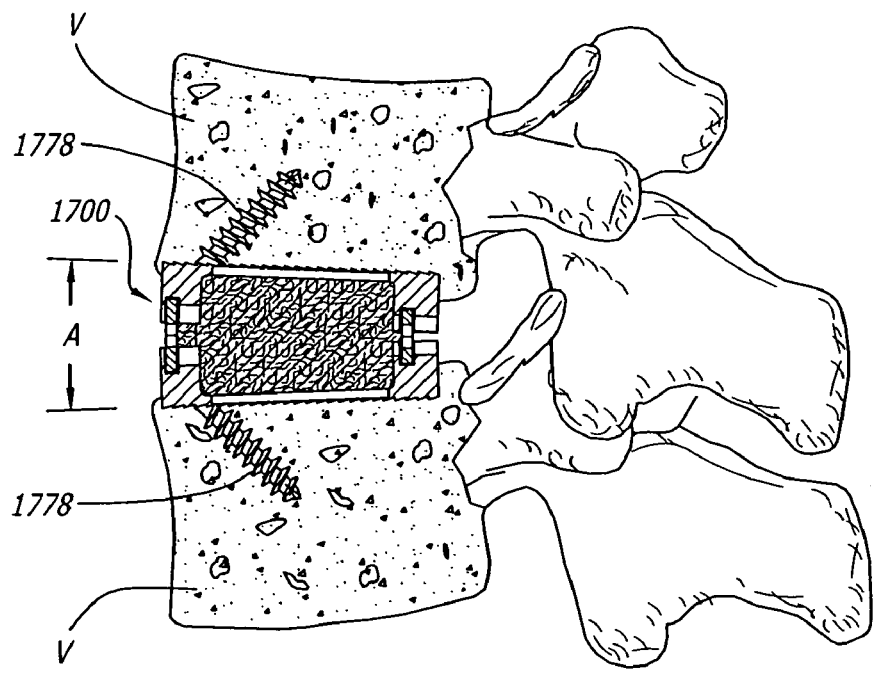
FIG. 74 is a cross-sectional side view of the implantation site formed across the space between two adjacent vertebral bodies and of the implant of FIG. 68 installed into the implantation site in the final deployed position with upper and lower surfaces in angular orientation to one another and bone screws installed to anchor the implant.
Figure 75:
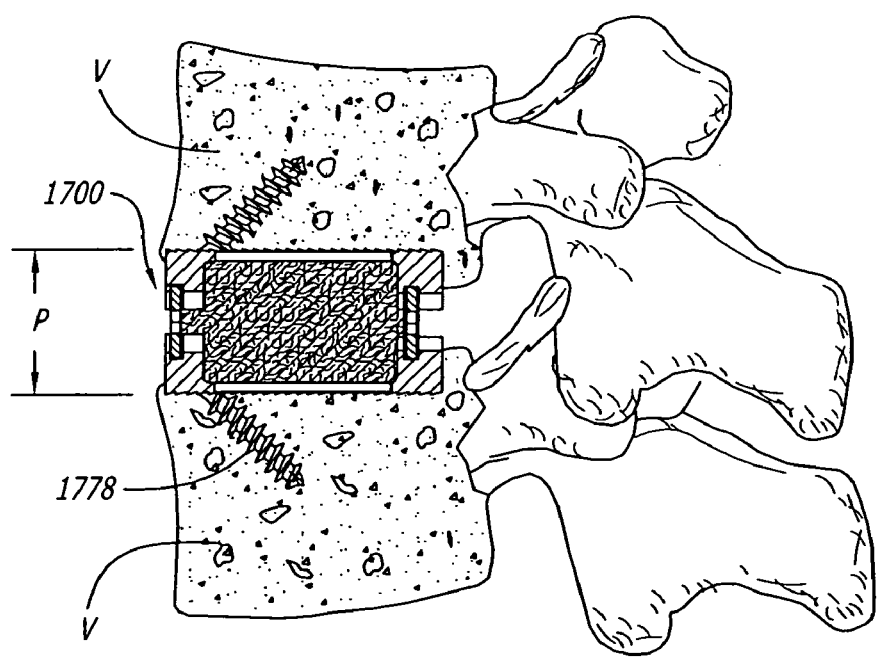
FIG. 75 is a cross-sectional side view of the implantation site formed across the space between two adjacent vertebral bodies and of the implant of FIG. 68 installed into the implantation space in the final deployed position with upper and lower surfaces in parallel orientation to one another and bone screws installed to anchor the implant.

FIG. 72A is a side view of an alternative implant having an anatomically shaped upper and lower surface for insertion from the anterior aspect of the spine. The anatomical curvature may correspond to that of a disc or the surface of the vertebral endplate. In another embodiment, the upper and lower surfaces may have a relatively mild convexity in both directions, that is from leading to trailing end as well as side-to-side so as to better conform to the anatomical shape of the disc space or the vertebral endplates.

Figure 76:
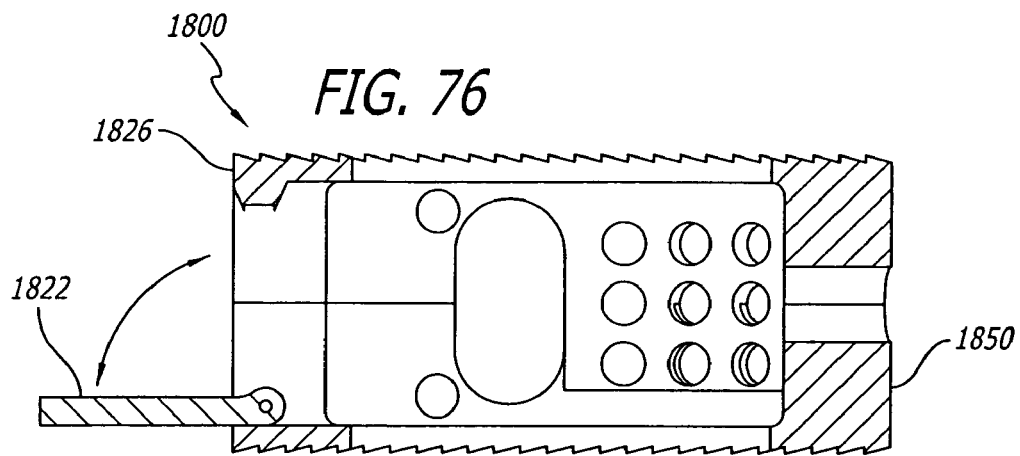
FIG. 76 is a cross-sectional side view of an alternative embodiment of an implant of the present invention with a pivoting trailing end that is also a blocker with the trailing end in the open position.
Figure 77:
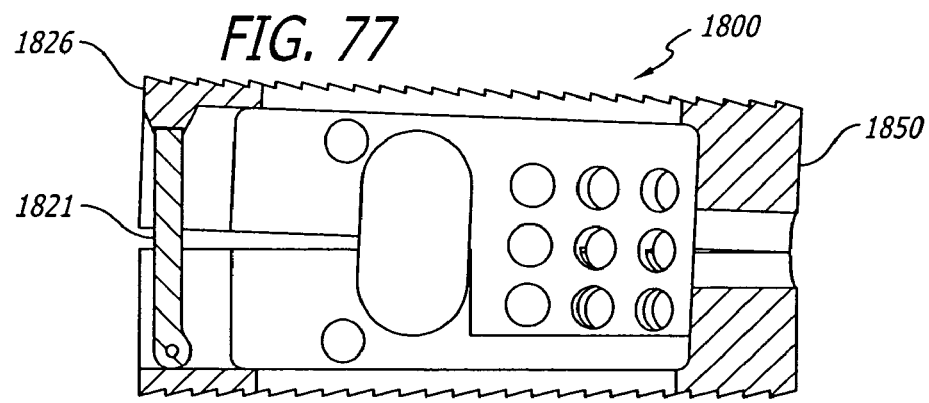
FIG. 77 is a cross-sectional side view of an alternative embodiment of an implant of FIG. 76 with the trailing end in the closed position.
Figure 78:
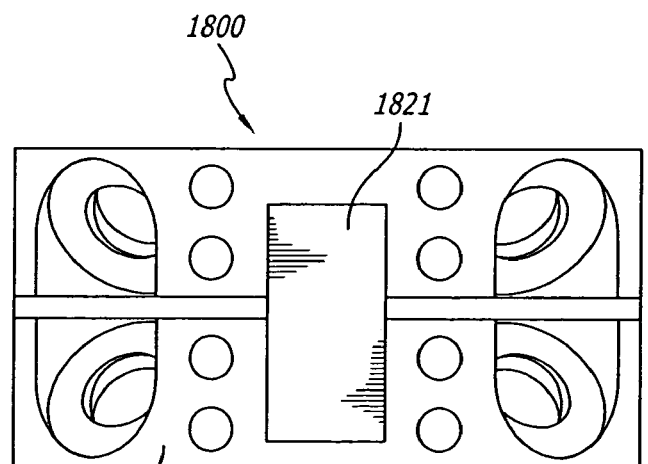
FIG. 78 is a trailing end perspective view of the implant of FIG. 77.
Figure 82:
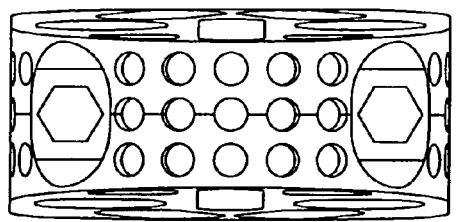
FIG. 82 is a leading end view of the implant of FIG. 80.
Figure 81:
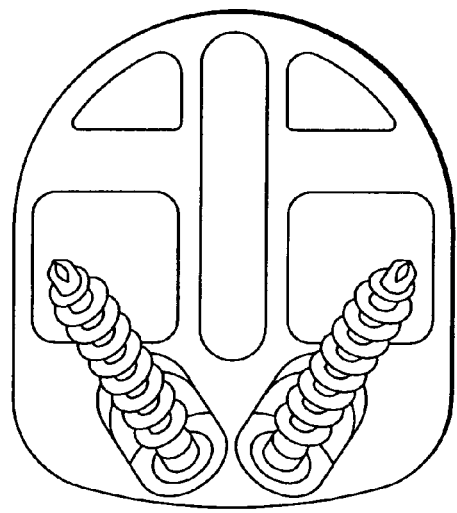
FIG. 81 is a top plan view of the implant of FIG. 80 with bone screws installed.
Figure 83:
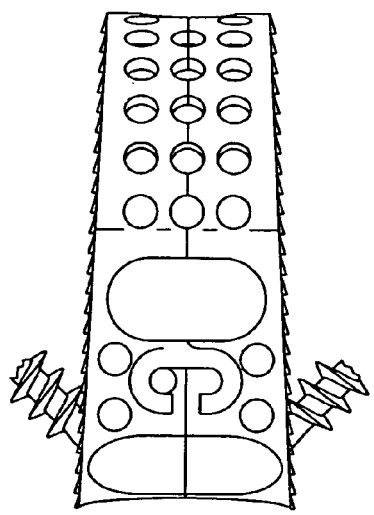
FIG. 83 is a side elevation view of the implant of FIG. 81.
Figure 80:
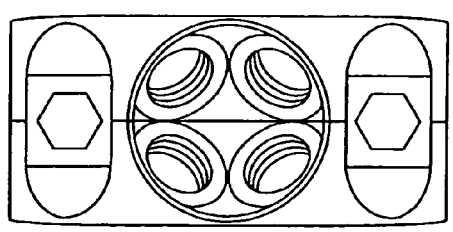
FIG. 80 is a trailing end view of another preferred embodiment of the implant of the present invention having four expanders and adapted to be inserted from an anterior approach to the spine.

An alternative embodiment of an implant for use from the anterior approach is shown in FIGS. 76 through 78. In implant 1800 blocker 1822 takes the form of a trailing wall that articulates or hinges to the inside of implant 1800. The trailing wall may be left open during insertion of implant 1800 so as to trail behind the upper and lower members. Once implant 1800 is implanted into position, the trailing wall is rotated about one of its ends and pushed into position and locked into place. This may occur by having the trailing wall contact an inclined plane that leads up to a notch into which the trailing wall locks into place. The trailing wall itself may also have at least one opening in it to permit the further loading of fusion-promoting materials into implant 1800.

FIGS. 79 and 79A show a preferred embodiment of an expandable interbody spinal fusion implant 1900 and an expanding and locking end cap 2000 for use therewith in accordance with the present invention. As shown in FIG. 79, implant 1900 preferably has a trailing end 1926 that includes openings 1980 to permit for the growth of bone through implant 1900. Implant 1900 has a bone-engaging projection that is preferably one of ratchets, splines, knurling, or other surfaces rougheniings to resist expulsion of the implant from the disc space after implantation.

FIGS. 80-84 show another preferred embodiment of the implant 2100 that is adapted to be inserted from an anterior approach to the spine. In implant 2100 two sets of expanders 2122 are used, each set being located on one side of the mid-longitudinal axis of implant 2100. Depending upon the type of articulation used, expanders 2122 may be rotated to confer a transverse angulation as well as longitudinal angulation to the upper and lower members of implant 2100 in situations where such angulation is desired. All four expanders 2122 may be used to expand the upper and lower members of implant 2100 by the same or different amount relative to one another. This can be done to permit the surgeon to expand the leading and trailing ends or sides by varying degrees.

Another aspect of implant 2100 is that its upper and lower members have screw holes passing therethrough adapted to receive a bone screw passing from the interior of implant 2100 into adjacent vertebral bodies to anchor implant 2100 to an adjacent vertebral body. A purpose of the opposed bone screws is to rigidly secure the implant within the vertebral segment. A further purpose is to pull each of the adjacent vertebral bodies toward the implant and towards each other.

Figure 85:
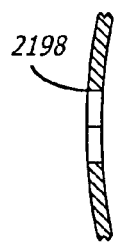
FIG. 85 is a side view in partial cross section of a cap for use with the implant of FIG. 80.
Figure 84:
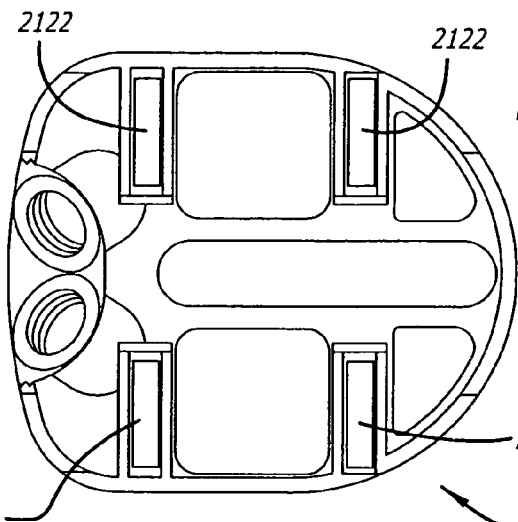
FIG. 84 is a top plan view of the lower member of the implant of FIG. 80.

FIG. 85 shows a preferred embodiment of an end cap 2198 for locking the bone screws to implant 2100. The end cap is preferably configured to threadably engage the opening in the trailing end of implant 2100.

Figure 86:
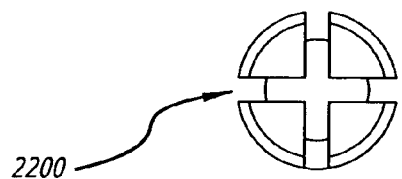
FIG. 86 is a top plan view of a preferred embodiment of a bone screw for use with the implant of FIG. 80.
Figure 87:
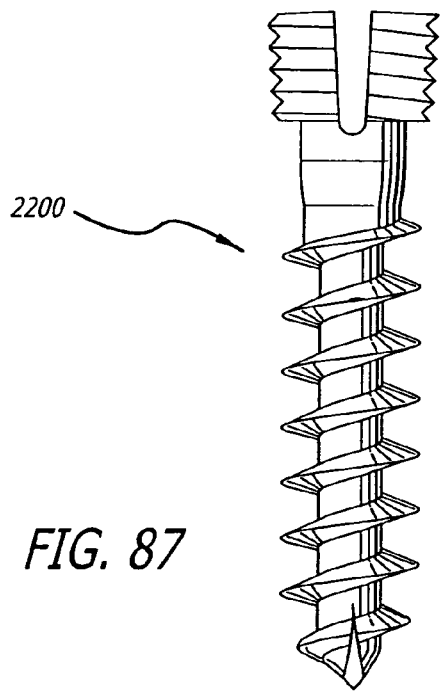
FIG. 87 is a side elevation view of the screw of FIG. 86.
Figure 91:
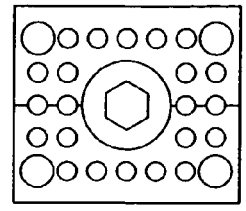
FIG. 91 is a trailing end view of the implant of FIG. 88.
Figure 88:
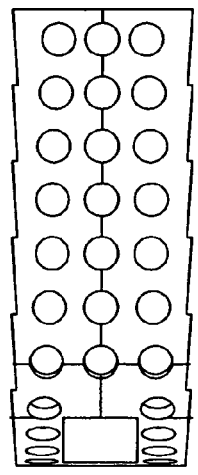
FIG. 88 is an exterior facing side elevation view of another preferred embodiment of an implant of the present invention adapted to be inserted from a posterior approach to the spine preferably in pairs.
Figure 89:
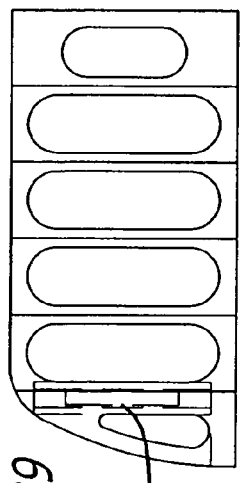
FIG. 89 is a top plan view of the implant of FIG. 88.
Figure 92:
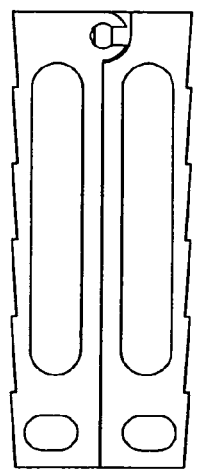
FIG. 92 is an interior facing side elevation view of the implant of FIG. 88.
Figure 90:
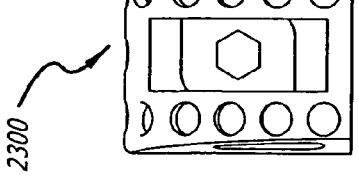
FIG. 90 is a leading end view of the implant of FIG. 88.
Figure 93:
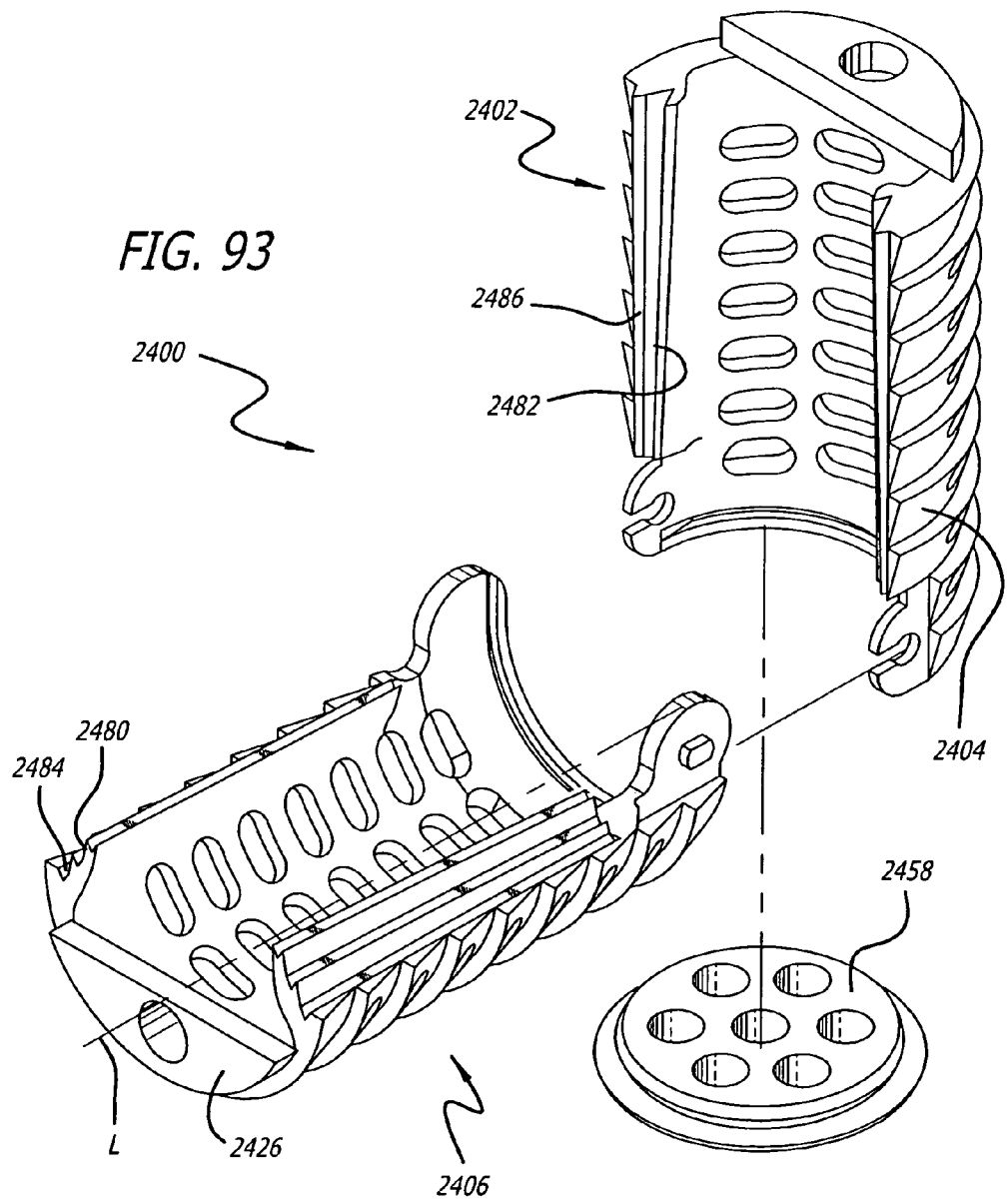
FIG. 93 is an exploded perspective view of a spinal fusion implant of another embodiment of the present invention.
Figure 96:
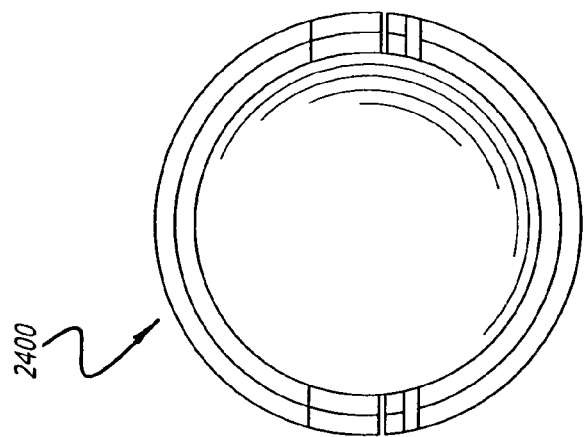
FIG. 96 is a leading end view of the implant of FIG. 95.
Figure 95:
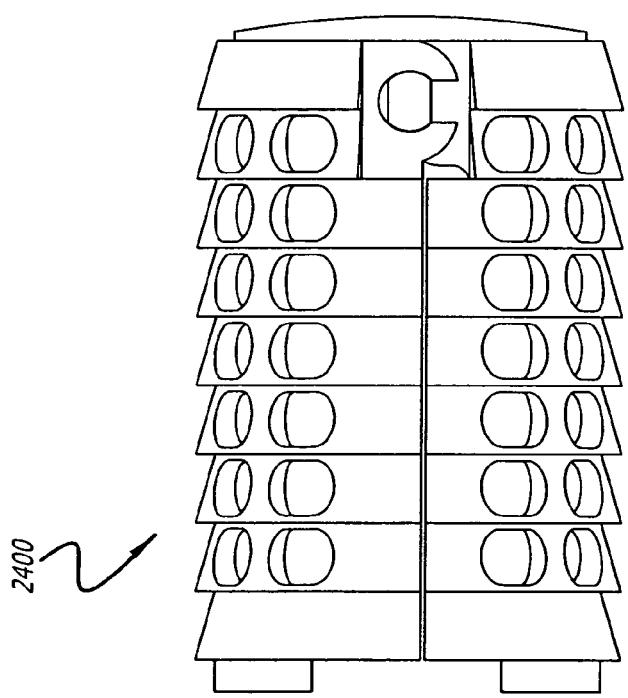
FIG. 95 is a side view of the implant of FIG. 93 in the first or collapsed position.
Figure 94:
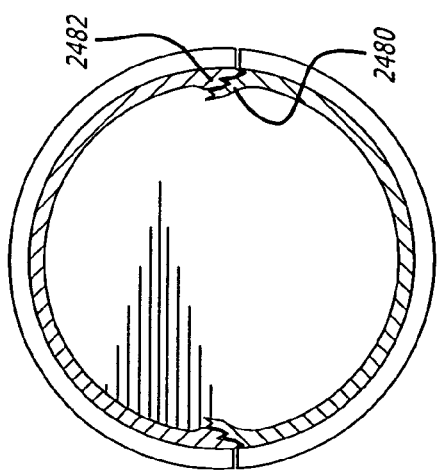
FIG. 94 is a trailing end view of the implant of FIG. 95.

FIGS. 86 and 87 show a preferred embodiment of a bone screw 2200 for use with implant 2100. Bone screw 2200 preferably has a threaded head portion to threadably engage the screw holes of implant 2100. Bone screw 2200 is self-locking since the thread pattern of the head is different from the thread pattern along the shaft of the screw that penetrates the bone. It is appreciated that bone screws are not essential to the operation of the invention, but are preferable for providing added securement of the implant to the adjacent vertebral bodies.

FIGS. 88-92 show another preferred embodiment of an implant 2300 of the present invention adapted to be inserted from a posterior approach to the spine. Implant 2300 is preferably installed in pairs, to either side of the mid-sagittal axis of the vertebral bodies. Each implant 2300 in the pair is preferably a mirror image of the other. Implant 2300 preferably has a leading end for placement toward the anterior aspect of the vertebral bodies that is configured to conform to at least a portion of the anterior aspect of the vertebral bodies. The upper and lower members are preferably articulated at the trailing end of implant 2300. An expander 2322 located proximate the leading end of implant 2300 is used to angulate the upper and lower members of implant 2300 to place the adjacent vertebral bodies in proper lordosis. Expander 2322 is manipulated by a tool inserted from a posterior approach through the trailing end of the implant. For insertion from an anterior approach to the spine, it is appreciated that in an alternative embodiment, expander 2322 may be located proximate the trailing end of the implant with the upper and lower members being articulated at the leading end of the implant.

FIGS. 93-98 show another preferred embodiment of an implant 2400 of the present invention. Each of upper and lower members 2402, 2406 of at least one embodiment of the present invention have side walls 2480, 2482 adapted to cooperatively engage one another along at least a portion of the length of side walls 2480, 2482 to hold at least a portion of upper and lower members 2402,2406 apart so as to maintain the increased height of implant 2400 and resist the collapse of implant 2400 to the collapsed implant height when implant 2400 is in a final deployed position. Preferably side walls 2480, 2482 of at least one, and if desired both, of upper and lower members 2402, 2406 flex when implant 2400 is moved from the first position to the second position. In particular, when implant 2400 is moved from the first position to the second position certain of side walls 2480, 2482 may spring from a position closer to mid-longitudinal axis L of implant 2400 to a position further away from mid-longitudinal axis L or may spring from a position further from mid-longitudinal axis L of implant 2400 to a position closer to mid-longitudinal axis L. This movement of at least one of side walls 2480, 2482 may include rotating at least a portion of the side wall along an arc around an axis that is parallel to mid-longitudinal axis L of implant 2400 when implant 2400 is moved from the first position to the second position. These rotational, flexing, or springing forces acting to engage cooperatively configured side walls 2480, 2482 of upper and lower members 2402, 2406 together add lateral stability to implant 2400 while maintaining the increased height of implant 2400.

Preferably, side walls 2480, 2482 of upper and lower members 2402, 2406 have cooperatively engaging stepped surfaces. Preferred stepped surfaces of one embodiment of the present invention include interdigitating projections 2486 and detents 2484. Side walls having detents 2484 preferably have more detents 2484 than the cooperatively engaging side walls having projections 2486 have projections 2486 to permit implant 2400 to move from the first position to the second position. During movement of implant 2400 from the first position to the second position side walls 2480 having detents 2484 in one embodiment have at least one detent 2484 that narrows during movement of side wall 2480 having detents 2484. This movement moves side wall 2480 having detents 2484 into alignment and engagement with projections 2486 of side wall 2482 having projections 2486 to increase the height of implant 2400. One particular preferred embodiment of the present invention includes side walls 2482 with two projections 2486 adapted to cooperatively engage side walls 2480 with three detents 2484. Moving two projections 2486 from the lower two of the three detents 2484 to the higher two of the three detents 2484 results in an increase to the maximum height of implant 2400.

Cooperatively engaging side walls 2480, 2482 preferably are at or near the equatorial region of implant 2400. Preferably, at least a portion proximate the equatorial region of implant 2400 is composed of a material that provides at least one of opposed cooperatively engaging side walls 2480, 2482 with a degree of resiliency. One preferred material is Nitonol, though it will be appreciated by those of ordinary skill in the art that many materials may be utilized for the purpose of providing resiliency, all of which are within the broad scope of the present invention.

While side walls 2480, 2482 of one preferred embodiment are substantially along the length of implant 2400, the invention is not so limited. Side walls 2480, 2482 may be along only a portion of implant 2400 length or if desired may be along a side wall that is on or near an end of the implant 2400 opposite the articulating end of implant 2400. For example, the cooperatively engaging side wall may be on trailing end wall 2426, which is specifically identified as a side wall herein for purposes of this disclosure, and the structure permitting articulation may be on or near the leading end of implant 2400. If the structure permitting articulation of the implant is on or near the trailing end of the implant then a cooperatively engaging side wall may be on the leading end wall, which is specifically identified as a side wall herein for purposes of this disclosure. Additionally, although the side walls are shown in FIGS. 93-98 as being substantially parallel to the implant axis, it is also within the scope of the present invention to have the side walls at an angle with respect to the implant mid-longitudinal axis. The cooperatively engaging side walls of the present invention may be used with any of the implants disclosed herein instead of or in addition to the disclosed blocker and expander embodiments of the present invention or with any other expandable implant were suitable for the purpose of providing the necessary support and stability to the implant.

The expandable spinal fusion implant may be made of artificial or naturally occurring materials suitable for implantation in the human spine. The implant can comprise bone including, but not limited to, cortical bone. The implant can also be formed of material other than bone, such as metal including, but not limited to, titanium and its alloys or ASTM material, surgical grade plastics, plastic composites, ceramics, or other materials suitable for use as a spinal fusion implant. The plastics may be bioabsorbable. The spinal fusion implant of the present invention can further be formed of bone growth promoting materials, including but not limited to, bone morphogenetic proteins, hydroxyapatite, and genes coding for the production of bone. The implant can be treated with a bone growth promoting substance, can be a source of osteogenesis, or can be at least in part bioabsorbable. The implant of the present invention can be formed of a porous material.

The expandable spinal fusion implant of the present invention may be coated with, comprised of, be used in combination with, or have a hollow for containing bone growth promoting materials, including but not limited to, bone morphogenetic proteins, hydroxyapatite, and genes coding for the production of bone. The spinal fusion implant of the present invention can be formed of a material that intrinsically participates in the growth of bone from one of adjacent vertebral bodies V to the other of adjacent vertebral bodies V.

While various embodiments of the present invention are presented by way of example only and not limitation, common to each of them, is that the expandable spinal fusion implant for insertion across disc space D between two adjacent vertebral bodies V of a human spine has an upper member having a portion adapted for placement toward and into contact with or at least in part within the upper of the adjacent vertebral bodies V. The implant also has a lower member having a portion adapted for placement toward and into contact with or at least in part within the lower of the adjacent vertebral bodies V. The portions of the upper and lower members have at least one opening. The openings of the upper and lower members are in communication with one another to permit for the growth of bone from vertebral body V to adjacent vertebral body V through the implant. At least a portion of a bone-engaging projection for engaging adjacent vertebral bodies V is on the exterior of each of the opposed portions of the upper and lower members. An interlocking wall preferably is located proximate at least one of the ends to hold at least a portion of the upper and lower members apart from one another to increase the implant height. There is disclosed in the above description and the drawings implants, which fully and effectively accomplish the objectives of this invention. However, it will be apparent that variations and modifications of the disclosed embodiments may be made without departing from the principles of the invention or the scope of the appended claims.

What is claimed is:

1. An interbody spinal fusion implant for insertion at least in part across at least a surgically corrected height of a disc space between two adjacent vertebral bodies of a spine, said implant comprising:

a mid-longitudinal axis;

an upper member having a portion adapted for placement toward and into contact with one of the adjacent vertebral bodies, said upper member having at least one opening adapted to communicate with one of the adjacent vertebral bodies, said upper member having a proximal end and a distal end, and a length between said proximal and distal ends;

a lower member having a portion adapted for placement toward and into contact with the other of the adjacent vertebral bodies, said lower member having at least one opening adapted to communicate with the other of the adjacent vertebral bodies, said openings of said upper and lower members being in communication with one another and being adapted to permit growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating about a pivot axis transverse to the mid-longitudinal axis and adjacent one of said proximal ends and said distal ends of said upper and lower members and allowing for expansion of said implant, said upper and lower members having a first position relative to one another allowing for a collapsed implant height and a second position relative to one another allowing for an increased height;

a plane parallel to the mid-longitudinal axis and passing through the pivot axis of said upper and lower members; and each of said upper and lower members having side walls, each of said side walls having a length, said side walls being adapted to cooperatively engage one another along at least a portion of the length of said side walls to hold at least a portion of said upper and lower members apart so as to maintain the increased height of said implant and resist the collapse of said implant to the collapsed implant height when said implant is in a final deployed position, one of said side walls having a first load bearing surface with a longitudinal axis that is non-perpendicular to the mid-longitudinal axis of the implant, another of said side walls having a second load bearing surface for contacting said first load bearing surface, wherein at least one of said sidewalls moves in the plane in one of a direction away from and toward the mid-longitudinal axis when said implant is moved from the first position to the second position.

2. The implant of claim 1, wherein one of said first and second load bearing surfaces is a groove, and the other of said first and second load bearing surfaces is a projection.

3. The implant of claim 1, wherein said side walls of at least one of said upper and lower members flex when said implant is moved from the first position to the second position.

4. The implant of claim 1, wherein said side walls of both of said upper and lower members flex when said implant is moved from the first position to the second position.

5. The implant of claim 1, wherein at least one of said side walls of at least one of said upper and lower members spring from a position closer to the mid-longitudinal axis of said implant to a position further away from the mid-longitudinal axis when said implant is moved from the first position to the second position.

6. The implant of claim 1, wherein at least one of said side walls of at least one of said upper and lower members spring from a position further from the mid-longitudinal axis of said implant to a position closer to the mid-longitudinal axis when said implant is moved from the first position to the second position.

7. The implant of claim 1, wherein at least a portion of at least one of said side walls of at least one of said upper and tower members rotates along an arc of an axis that is parallel to the mid-longitudinal axis of said implant when said implant is moved from the first position to the second position.

8. The implant of claim 1, wherein said side walls of said upper and lower members have cooperatively engaging stepped surfaces.

9. The implant of claim 8, wherein said cooperatively engaging stepped surfaces of said cooperatively engaging side walls have interdigitating projections and recesses.

10. The implant of claim 9, wherein said side walls having said projections have two projections.

11. The implant of claim 10, wherein said side waits having said recesses have three recesses.

12. The implant of claim 9, wherein said side waits having recesses have more recesses than said cooperatively engaging side walls having projections have projections to permit said implant to move from the first position to the second position when said projections are moved from engagement with a first set of said recesses to a second set of said recesses.

13. The implant of claim 9, wherein during movement of said implant from the first position to the second position said side walls having recesses have at least one recess that narrows during movement of said side wall having recesses.

14. The implant of claim 13, wherein said side wall having recesses moves into alignment and engagement with said projections of said wall having projections to increase the height of said implant during movement of implant from the first position to the second position.

15. The implant of claim 1, wherein said side walls are aligned parallel with the mid-longitudinal axis of said implant.

16. The implant of claim 1, wherein said side walls are adapted to maintain said portions of said upper and lower members at an angled orientation relative to one another when said implant is in the second position.

17. The implant of claim 1, wherein said side walls are adapted to maintain said portions of said upper and lower members at a parallel orientation relative to one another when said implant is in the second position.

18. The implant of claim 1, wherein one of said upper and lower members has an interior wall, which is unexposed, extending therefrom toward the other of said upper and lower members when said implant is in an initial insertion position, and when said implant is in a final position said implant has a shape such that each of said portions of said upper and lower members are separated by at least a portion of said interior wall, which now has an exposed side.

19. The implant of claim 1, wherein said upper and lower members are configured to cooperate with one another so as to stop said upper and lower members from being moved apart from one another more than a predetermined distance.

20. The implant of claim 1, wherein said implant has a side surface when in a final position that is contoured to cooperate with another implant.

21. The implant of claim 1, wherein said implant is adapted to cooperatively engage a tool used to move said implant from an initial position to a final position to increase the height of said implant, said tool not being a part of said implant and being removed from engagement with said implant after moving said implant into the final position.

22. The implant of claim 1, wherein at least one of said side walls is a form of Nitonal.

23. The implant of claim 1, wherein said articulation allows for expansion.

24. The implant of claim 1, wherein said articulation allows for limited expansion.

25. The implant of claim 1, wherein said articulation is formed by said upper and lower members interdigitating so as to cooperatively engage.

26. The implant of claim 1, wherein said articulation is configured such that to permit articulation and disarticulation engagement occurs when said upper and lower members are substantially perpendicular to one another.

27. The implant of claim 1, wherein said articulation is configured to remain engaged within a range of movement of said upper and lower members resulting from positioning said implant in the second position.

28. The implant of claim 1, further comprising at least a portion of a bone-engaging projection formed on the exterior of each of said opposed portions of said upper and lower members for engaging the adjacent vertebral bodies and to facilitate securing said implant into the spine.

29. The implant of claim 28, wherein said bone-engaging projection is at least a portion of a helical thread to facilitate securing said implant into the spine by at least in part rotating said implant about the longitudinal axis of said implant.

30. The implant of claim 28, wherein said bone-engaging projection is adapted for linear insertion.

31. The implant of claim 1, further comprising at least a portion of a bone-engaging projection adapted for linear insertion formed on the exterior of each of said portions of said upper and lower members for penetrably engaging the adjacent vertebral bodies and to facilitate securing said implant into the spine.

32. The implant of claim 31, wherein said bone-engaging projection is selected from one of a ratchet, a surface roughening, and a knurling.

33. The implant of claim 1, wherein said portions of said upper and lower members are at least in part arcuate and adapted for placement toward and at least in part within one of the adjacent vertebral bodies.

34. The implant of claim 33, wherein said arcuate portions of said upper and lower members in the first position are parallel to one another over a substantial portion of the length of said implant and form at least a portion of a cylinder along the length of said implant.

35. The implant of claim 33, wherein said arcuate portions of said upper and lower members in the first position are angled to one another over a substantial portion of the length of said implant and form at least a portion of a frusto-conical shape along the length of said implant.

36. The implant of claim 33, wherein said arcuate portions of said upper and lower members in the first position are angled to one another over a substantial portion of the length of said implant and form at least a portion of the shape of a cylinder split along a horizontal plane through its mid-longitudinal axis with said upper member and said lower member being angled to each other along the length of said implant.

37. The implant of claim 33, further comprising a second interbody spinal fusion implant comprising:
    an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;
    a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting the growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends; and
    at least a portion of a bone-engaging projection formed on the exterior of each of said opposed arcuate portions of said upper and lower members for penetrably engaging the adjacent vertebral bodies and to facilitate securing said implant into the spine, said first and second implants when in side-to-side contact having a combined width substantially less than the combined heights as measured from the upper to the lower bone-engaging surfaces of said first and second implants.

38. The implant of claim 1, wherein said portions of said upper and lower members are non-arcuate along a substantial portion of the length of said implant.

39. The implant of claim 1, wherein said implant is substantially parallelepiped.

40. The implant of claim 1, further comprising at least one blocker adapted to cooperatively engage and hold at least a portion of said upper and lower members apart so as to maintain the increased height of said implant and resist the collapse of said implant to the collapsed implant height when said implant is in a final deployed position.

41. The implant of claim 40, wherein said blocker pivotally attaches to one of said upper and lower members and is adapted to pivot into cooperative engagement with another of said one of said upper and lower members, said blocker being adapted to hold at least a portion of said upper and lower members apart so as to maintain the increased height of said implant and resist the collapse of said implant to the collapsed implant height when said implant is in a final deployed position.

42. The implant of claim 40, wherein said implant having a width and said blocker having a width less than the width of said implant.

43. The implant of claim 40, wherein said blocker is a portion of one of said ends of said upper and lower members.

44. The implant of claim 40, wherein said blocker is located at least in part between said upper and lower members.

45. The implant of claim 40, wherein said blocker is located proximate at least one of said ends of said upper and lower members.

46. The implant of claim 40, wherein said blocker is adapted to cooperatively engage a tool used to move said blocker from an initial position to a final position to increase the height of said implant, said tool not being a part of said implant and being removed from said implant after moving said blocker into the final position.

47. The implant of claim 40, wherein each of said upper and lower members have a track configured to permit said blocker to seat therein.

48. The implant of claim 40, wherein said blocker moves said portions of said upper and lower members from a parallel orientation to an angled orientation relative to one another.

49. The implant of claim 40, wherein said blocker moves said portions of said upper and lower members from a first angled orientation to a second angled orientation relative to one another.

50. The implant of claim 40, wherein said articulation is at one of said proximal end and said distal end of said upper and lower members opposite said blocker.

51. The implant of claim 40, further comprising a second blocker located between said upper and lower members for holding at least a portion of the upper and lower members apart where said second expander is located.

52. The implant of claim 40, wherein said blocker is an expander adapted to expand said implant from a first collapsed height to a second expanded height when moved from a first to a second position.

53. The implant of claim 52, wherein said expander rotates in a plane generally perpendicular to the mid-longitudinal axis of said implant to increase the height of said implant.

54. The implant of claim 52, wherein said expander has a fixed shape during movement from an initial insertion position to a final deployed position within said implant.

55. The implant of claim 52, further comprising a second expander located between said upper and lower members for moving at least a portion of the upper and lower members away from one another to increase the maximum height of said implant where said second expander is located.

56. The implant of claim 55, wherein said second expander rotates to increase the height of said implant.

57. The implant of claim 55, wherein said second expander has a first height corresponding to the height of said second expander when said implant is initially inserted into the spine, said second expander having a second height corresponding to the height of said second expander when said second expander is moved into a final deployed position to increase the height of said second implant, said second height being greater than said first height.

58. The implant of claim 40, wherein said blocker is an expander having an external thread, each of said upper and lower members having a threaded converging portion adapted to cooperate with said external thread of said expander to expand said implant from a first collapsed height to a second expanded height when said expander is rotated from a first to a second position.

59. The implant of claim 1, further comprising a hollow defined between said upper and lower members in communication with said openings in each of said upper and lower members, said hollow being adapted to receive fusion-promoting substances.

60. The implant of claim 59, wherein said hollow has a width that is unobstructed by any mechanism expanding said implant.

61. The implant of claim 1, wherein said implant has a constant width in both the first position and the second position.

62. The implant of claim 1, wherein said implant has an interior, at least one of said upper and lower members has a screw hole passing therethrough adapted to receive a screw passing from said interior of said implant into one of the adjacent vertebral bodies.

63. The implant of claim 62, wherein each of said upper and lower members has at least one screw hole passing therethrough adapted to receive a screw passing from said interior of said implant into the adjacent vertebral body in contact with each of said upper and lower members respectively.

64. The implant of claim 62, further comprising at least one screw adapted to pass from said interior of said implant through said screw hole and into the adjacent vertebral body to anchor said implant to the adjacent vertebral body.

65. The implant of claim 1, further comprising a cap for closing one of said proximal end and said distal end of said upper and lower members, said cap having an exterior surface and an interior surface.

66. The implant of claim 65, wherein said interior surface of said cap has spaced slots about its circumference to facilitate a snap fit of said cap into said implant.

67. The implant of claim 1, wherein said implant is made of an artificial material that is harder than bone.

68. The implant of claim 1, wherein said implant comprises bone.

69. The implant of claim 68, wherein said bone includes cortical bone.

70. The implant of claim 1, in combination with a bone growth promoting material.

71. The implant of claim 70, wherein said bone growth promoting material is selected from one of bone morphogenetic protein, hydroxyapatite, and genes coding for the production of bone.

72. The implant of claim 1, wherein said implant is treated with a bone growth promoting substance.

73. The implant of claim 1, wherein said implant is a source of osteogenesis.

74. The implant of claim 1, wherein said implant is at least in part bioabsorbable.

75. The implant of claim 1, wherein said implant comprises a material selected from one of plastic and ceramic.

76. The implant of claim 1, wherein said implant is formed of a material that intrinsically participates in the growth of bone from adjacent vertebral body to adjacent vertebral body through said implant.

77. The implant of claim 1, in combination with a chemical substance to inhibit scar formation.

78. An interbody spinal fusion implant for insertion at least in part across at least a surgically corrected height of a disc space between two adjacent vertebral bodies of a spine, said implant comprising:
a mid-longitudinal axis;
an upper member having a portion adapted for placement toward and into contact with one of the adjacent vertebral bodies, said upper member having at least one opening adapted to communicate with one of the adjacent vertebral bodies, said upper member having a proximal end and a distal end, and a length between said proximal and distal ends;
a lower member having a portion adapted for placement toward and into contact with the other of the adjacent vertebral bodies, said lower member having at least one opening adapted to communicate with the other of the adjacent vertebral bodies, said openings of said upper and lower members being in communication with one another and being adapted to permit growth of bone from adjacent vertebral body to adjacent vertebral body through said implant and being sufficiently sized and located to allow for interbody spinal fusion through said implant, said lower member having a proximal end and a distal end corresponding to said proximal end and said distal end of said upper member, respectively, and a length between said proximal and distal ends, said upper and lower members articulating about a pivot axis transverse to the mid longitudinal axis and adjacent one of said proximal ends and said distal ends of said upper and lower members and allowing for expansion of said implant, said upper and lower members having a first position relative to one another allowing for a collapsed implant height and a second position relative to one another allowing for an increased height;
a plane parallel to the mid-longitudinal axis and passing through the pivot axis of said upper and lower members; and
each of said upper and lower members having side walls, each of said side walls having a length, an interior surface, and an exterior surface, said side walls being adapted to cooperatively engage one another along at least a portion of the length of said side walls to hold at least a portion of said upper and lower members apart so as to maintain the increased height of said implant and resist the collapse of said implant to the collapsed implant height when said implant is in a final deployed position, one of said interior surfaces of one of said upper and lower members contacting one of said exterior surfaces of the other of said upper and lower members, said interior and exterior surfaces contacting one another forming a generally coplanar transition between said upper and lower members, wherein at least one of said sidewalls moves in the plane in one of a direction away from and toward the mid-longitudinal axis when said implant is moved from the first position to the second position.

79. The implant of claim 78, wherein the coplanar transition is at least in part curved.

80. The implant of claim 78, wherein said interior surfaces of said side walls form the generally coplanar transition.

81. The implant of claim 80, wherein the generally coplanar transition is formed when said implant is in the final deployed position.

82. The implant of claim 78, wherein said exterior surfaces of said side walls form the coplanar transition.

83. The implant of claim 82, wherein the coplanar transition is formed when said implant is in the first position.

84. The implant of claim 82, wherein the coplanar transition is formed when said implant is in the final deployed position.

85. The implant of claim 78, wherein the coplanar transition is formed when said implant is in the first position.

86. The implant of claim 78, wherein said side walls of at least one of said upper and lower members flex when said implant is moved from the first position to the second position.

87. The implant of claim 78, wherein said side walls of both of said upper and lower members flex when said implant is moved from the first position to the second position.

88. The implant of claim 78, wherein at least one of said side walls of at least one of said upper and lower members spring from a position closer to the mid-longitudinal axis of said implant to a position further away from the mid-longitudinal axis when said implant is moved from the first position to the second position.

89. The implant of claim 78, wherein at least one of said side walls of at least one of said upper and lower members spring from a position further from the mid-longitudinal axis of said implant to a position closer to the mid-longitudinal axis when said implant is moved from the first position to the second position.

90. The implant of claim 78, wherein at least a portion of at least one of said side walls of at least one of said upper and lower members rotates along an arc of an axis that is parallel to the mid-longitudinal axis of said implant when said implant is moved from the first position to the second position.

91. The implant of claim 78, wherein said side walls of said upper and lower members have cooperatively engaging stepped surfaces.

92. The implant of claim 91, wherein said cooperatively engaging stepped surfaces of said cooperatively engaging side walls have interdigitating projections and recesses.

93. The implant of claim 92, wherein said side walls having said projections have two projections.

94. The implant of claim 93, wherein said side walls having said recesses have three recesses.

95. The implant of claim 92, wherein said side walls having recesses have more recesses than said cooperatively engaging side walls having projections have projections to permit said implant to move from the first position to the second position when said projections are moved from engagement with a first set of said recesses to a second set of said recesses.

96. The implant of claim 92, wherein during movement of said implant from the first position to the second position said side walls having recesses have at least one recess that narrows during movement of said side wall having recesses.

97. The implant of claim 96, wherein said side wall having recesses moves into alignment and engagement with said projections of said wall having projections to increase the height of said implant during movement of said implant from the first position to the second position.

98. The implant of claim 78, wherein said side walls are aligned parallel with the mid-longitudinal axis of said implant.

99. The implant of claim 78, wherein said side walls are adapted to maintain said portions of said upper and lower members at an angled orientation relative to one another when said implant is in the second position.

100. The implant of claim 78, wherein said side walls are adapted to maintain said portions of said upper and lower members at a parallel orientation relative to one another when said implant is in the second position.

101. The implant of claim 78, wherein said upper and lower members are configured to cooperate with one another so as to stop said upper and lower members from being moved apart from one another more than a predetermined distance.

102. The implant of claim 78, wherein said implant has a side surface when in a final position that is contoured to cooperate with another implant.

103. The implant of claim 78, wherein said implant is adapted to cooperatively engage a tool used to move said implant from an initial position to a final position to increase the height of said implant, said tool not being a part of said implant and being removed from engagement with said implant after moving said implant into the final position.

104. The implant of claim 78, wherein at least one of said side walls is a form of Nitonal.

105. The implant of claim 78, wherein said articulation allows for expansion.

106. The implant of claim 78, wherein said articulation allows for limited expansion.

107. The implant of claim 78, wherein said articulation is formed by said upper and lower members interdigitating so as to cooperatively engage.

108. The implant of claim 78, wherein said articulation is configured such that to permit articulation and disarticulation engagement occurs when said upper and lower members are substantially perpendicular to one another.

109. The implant of claim 78, wherein said articulation is configured to remain engaged within a range of movement of said upper and lower members resulting from positioning said implant in the second position.

110. The implant of claim 78, further comprising at least a portion of a bone-engaging projection formed on the exterior of each of said opposed portions of said upper and lower members for engaging the adjacent vertebral bodies and to facilitate securing said implant into the spine.

111. The implant of claim 110, wherein said bone-engaging projection is at least a portion of a helical thread to facilitate securing said implant into the spine by at least in part rotating said implant about the longitudinal axis of said implant.

112. The implant of claim 110, wherein said bone-engaging projection is adapted for linear insertion.

113. The implant of claim 78, further comprising at least a portion of a bone-engaging projection adapted for linear insertion formed on the exterior of each of said portions of said upper and lower members for penetrably engaging the adjacent vertebral bodies and to facilitate securing said implant into the spine.

114. The implant of claim 113, wherein said bone-engaging projection is selected from one of a ratchet, a surface roughening, and a knurling.

115. The implant of claim 78, wherein said portions of said upper and lower members are at least in part arcuate and adapted for placement toward and at least in part within one of the adjacent vertebral bodies.

116. The implant of claim 115, wherein said arcuate portions of said upper and lower members in the first position are parallel to one another over a substantial portion of the length of said implant and form at least a portion of a cylinder along the length of said implant.

117. The implant of claim 115, wherein said arcuate portions of said upper and lower members in the first position are angled to one another over a substantial portion of the length of said implant and form at least a portion of a frusto-conical shape along the length of said implant.

118. The implant of claim 115, wherein said arcuate portions of said upper and lower members in the first position are angled to one another over a substantial portion of the length of said implant and form at least a portion of the shape of a cylinder split along a horizontal plane through its mid-longitudinal axis with said upper member and said lower member being angled to each other along the length of said implant.

119. The implant of claim 115, further comprising a second interbody spinal fusion implant comprising:
   an upper member having a portion being at least in part arcuate adapted for placement toward and at least in part within one of the adjacent vertebral bodies, said upper member having at least one opening adapted to communicate with one of the adjacent vertebral bodies, said upper member having a proximal end and a distal end;
   a lower member having a portion being at least in part arcuate adapted for placement toward and at least in part within the other of the adjacent vertebral bodies, said lower member having at least one opening adapted to communicate with the other of the adjacent vertebral bodies, said openings of said upper and lower members being in communication with one another and adapted for permitting for the growth of bone from adjacent vertebral body to adjacent vertebral body through said implant and being sufficiently sized and located to allow for interbody spinal fusion through said implant, said lower member having a proximal a proximal end and a distal end corresponding to said proximal end and said distal end of said upper member, respectively, and a length between said proximal and distal ends; and
   at least a portion of a bone-engaging projection formed on the exterior of each of said opposed arcuate portions of said upper and lower members for penetrably engaging the adjacent vertebral bodies and to facilitate securing said implant into the spine, said first and second implants when in side-to-side contact having a combined width substantially less than the combined heights as measured from the upper to the lower bone-engaging surfaces of said first and second implants.

120. The implant of claim 78, wherein said portions of said upper and lower members are non-arcuate along a substantial portion of the length of said implant.

121. The implant of claim 78, wherein said implant is substantially parallelepiped.

122. The implant of claim 78, further comprising at least one blocker adapted to cooperatively engage and hold at least a portion of said upper and lower members apart so as to maintain the increased height of said implant and resist the collapse of said implant to the collapsed implant height when said implant is in a final deployed position.

123. The implant of claim 122, wherein said blocker pivotally attaches to one of said upper and lower members and is adapted to pivot into cooperative engagement with another of said one of said upper and lower members, said blocker being adapted to hold at least a portion of said upper and lower members apart so as to maintain the increased height of said implant and resist the collapse of said implant to the collapsed implant height when said implant is in a final deployed position.

124. The implant of claim 122, wherein said implant having a width and said blocker having a width less than the width of said implant.

125. The implant of claim 122, wherein said blocker is a portion of one of said ends of said upper and lower members.

126. The implant of claim 122, wherein said blocker is located at least in part between said upper and lower members.

127. The implant of claim 122, wherein said blocker is located proximate at least one of said ends of said upper and lower members.

128. The implant of claim 122, wherein said blocker is adapted to cooperatively engage a tool used to move said blocker from an initial position to a final position to increase the height of said implant, said tool not being a part of said implant and being removed from said implant after moving said blocker into the final position.

129. The implant of claim 122, wherein each of said upper and lower members have a track configured to permit said blocker to seat therein.

130. The implant of claim 122, wherein said blocker moves said portions of said upper and lower members from a parallel orientation to an angled orientation relative to one another.

131. The implant of claim 122, wherein said blocker moves said portions of said upper and lower members from a first angled orientation to a second angled orientation relative to one another.

132. The implant of claim 122, wherein said articulation is at one of said proximal end and said distal end of said upper and lower members opposite said blocker.

133. The implant of claim 122, further comprising a second blocker located between said upper and lower members for holding at least a portion of the upper and lower members apart where said second expander is located.

134. The implant of claim 122, wherein said blocker is an expander adapted to expand said implant from a first collapsed height to a second expanded height when moved from a first to a second position.

135. The implant of claim 134, wherein said expander rotates in a plane generally perpendicular to the mid-longitudinal axis of said implant to increase the height of said implant.

136. The implant of claim 134, wherein said expander has a fixed shape during movement from an initial insertion position to a final deployed position within said implant.

137. The implant of claim 134, further comprising a second expander located between said upper and lower members for moving at least a portion of the upper and lower members away from one another to increase the maximum height of said implant where said second expander is located.

138. The implant of claim 137, wherein said second expander rotates to increase the height of said implant.

139. The implant of claim 137, wherein said second expander has a first height corresponding to the height of said second expander when said implant is initially inserted into the spine, said second expander having a second height corresponding to the height of said second expander when said second expander is moved into a final deployed position to increase the height of said implant, said second height being greater than said first height.

140. The implant of claim 122, wherein said blocker is an expander having an external thread, each of said upper and lower members having a threaded converging portion adapted to cooperate with said external thread of said expander to expand said implant from a first collapsed height to a second expanded height when said expander is rotated from a first to a second position.

141. The implant of claim 78, further comprising a hollow defined between said upper and lower members in communication with said openings in each of said upper and lower members, said hollow being adapted to receive fusion-promoting substances.

142. The implant of claim 141, wherein said hollow has a width that is unobstructed by any mechanism expanding said implant.

143. The implant of claim 78, wherein said implant has a constant width in both the first position and the second position.

144. The implant of claim 78, wherein said implant has an interior, at least one of said upper and lower members has a screw hole passing therethrough adapted to receive a screw passing from said interior of said implant into one of the adjacent vertebral bodies.

145. The implant of claim 144, wherein each of said upper and lower members has at least one screw hole passing therethrough adapted to receive a screw passing from said interior of said implant into the adjacent vertebral body in contact with each of said upper and lower members respectively.

146. The implant of claim 144, further comprising at least one screw adapted to pass from said interior of said implant through said screw hole and into the adjacent vertebral body to anchor said implant to the adjacent vertebral body.

147. The implant of claim 78, further comprising a cap for closing one of said proximal end and said distal end of said upper and lower members, said cap having an exterior surface and an interior surface.

148. The implant of claim 147, wherein said interior surface of said cap has spaced slots about its circumference to facilitate a snap fit of said cap into said implant.

149. The implant of claim 78, wherein said implant is made of an artificial material that is harder than bone.

150. The implant of claim 78, wherein said implant comprises bone.

151. The implant of claim 68, wherein said bone includes cortical bone.

152. The implant of claim 78, in combination with a bone growth promoting material.

153. The implant of claim 152, wherein said bane growth promoting material is selected from one of bone morphogenetic protein, hydroxyapatite, and genes coding for the production of bone.

154. The implant of claim 78, wherein said implant is treated with a bone growth promoting substance.

155. The implant of claim 78, wherein said, implant is a source of osteogenesis.

156. The implant of claim 78, wherein said implant is at least in part bioabsorbable.

157. The implant of claim 78, wherein said implant comprises a material selected from one of plastic and ceramic.

158. The implant of claim 78, wherein said implant is formed of a material that intrinsically participates in the growth of bane from adjacent vertebral body to adjacent vertebral body through said implant.

159. The implant of claim 78, in combination with a chemical substance to inhibit scar formation.

\* \* \* \* \*

UNITED STATES PATENT AND TRADEMARK OFFICE
CERTIFICATE OF CORRECTION

PATENT NO.       : 7,608,107 B2                                      Page 1 of 1
APPLICATION NO.  : 10/973974
DATED            : October 27, 2009
INVENTOR(S)      : Gary Karlin Michelson It is certified that error appears in the above-identified patent and that said Letters Patent is hereby corrected as shown below:

Title Page 1, Item (57) Abstract:
Line 10: change "alone" to -- along --.

Column 33:
Line 44: change "tower" to -- lower --; and
Lines 56 and 58: change "waits" to -- walls --.

Column 34:
Line 4: after "movement of" insert -- said --.

Column 41:
Line 32: delete "a proximal" (second occurrence).

Column 44:
Line 5: change "claim 68" to -- claim 150 --;
Line 9: change "bane" to -- bone --;
Line 15: change "said, implant" to -- said implant --; and
Line 23: change "bane" to -- bone --.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,608,107 B2 Page 1 of 1
APPLICATION NO. : 10/973974
DATED : October 27, 2009
INVENTOR(S) : Gary Karlin Michelson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 639 days.

Signed and Sealed this

Twelfth Day of October, 2010

David J. Kappos
*Director of the United States Patent and Trademark Office*